United States Patent
D'Amour et al.

(10) Patent No.: US 10,550,367 B2
(45) Date of Patent: *Feb. 4, 2020

(54) METHODS OF MAKING HUMAN PRIMITIVE ECTODERM CELLS

(71) Applicant: ViaCyte, Inc., San Diego, CA (US)

(72) Inventors: Kevin Allen D'Amour, San Diego, CA (US); Alan D. Agulnick, San Diego, CA (US); Susan Eliazer, Moraga, CA (US); Evert Kroon, San Diego, CA (US); Emmanuel E. Baetge, Encinitas, CA (US)

(73) Assignee: ViaCyte, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,999

(22) Filed: Oct. 2, 2018

(65) Prior Publication Data

US 2019/0032008 A1    Jan. 31, 2019

Related U.S. Application Data

(63) Continuation of application No. 15/654,624, filed on Jul. 19, 2017, now Pat. No. 10,179,902, which is a continuation of application No. 13/190,390, filed on Jul. 25, 2011, now Pat. No. 9,732,318, which is a continuation of application No. 11/474,211, filed on Jun. 23, 2006, now Pat. No. 7,985,585, which is a continuation of application No. PCT/US2005/024161, filed on Jul. 8, 2005, which is a continuation-in-part of application No. 11/021,618, filed on Dec. 23, 2004, now Pat. No. 7,510,876.

(60) Provisional application No. 60/693,364, filed on Jun. 23, 2005, provisional application No. 60/587,942, filed on Jul. 14, 2004, provisional application No. 60/586,566, filed on Jul. 9, 2004, provisional application No. 60/532,004, filed on Dec. 23, 2003.

(51) Int. Cl.
*C12N 5/0735* (2010.01)
*C12N 5/073* (2010.01)

(52) U.S. Cl.
CPC ......... *C12N 5/0606* (2013.01); *C12N 5/0603* (2013.01); *C12N 2500/90* (2013.01); *C12N 2501/115* (2013.01); *C12N 2501/155* (2013.01); *C12N 2501/16* (2013.01); *C12N 2506/02* (2013.01)

(58) Field of Classification Search
CPC ................................................... C12N 5/0606
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,816,567 A | 3/1989 | Cabilly et al. |
| 5,453,357 A | 9/1995 | Hogan |
| 5,670,372 A | 9/1997 | Hogan |
| 5,690,926 A | 11/1997 | Hogan |
| 5,817,637 A | 10/1998 | Weiner et al. |
| 5,830,876 A | 11/1998 | Weiner et al. |
| 5,843,780 A | 12/1998 | Thomson |
| 5,866,366 A | 2/1999 | Kallender |
| 5,869,620 A | 2/1999 | Whitlow et al. |
| 6,015,671 A | 1/2000 | Field |
| 6,090,592 A | 7/2000 | Adams et al. |
| 6,090,622 A | 7/2000 | Gearhart et al. |
| 6,117,635 A | 9/2000 | Nazarenko et al. |
| 6,117,986 A | 9/2000 | Nardone et al. |
| 6,165,993 A | 12/2000 | Herrmann et al. |
| 6,200,806 B1 | 3/2001 | Thomson |
| 6,251,671 B1 | 6/2001 | Hogan et al. |
| 6,261,281 B1 | 7/2001 | Mathiesen et al. |
| 6,458,589 B1 | 10/2002 | Rambhatla et al. |
| 6,506,574 B1 | 1/2003 | Rambhatla et al. |
| 6,872,389 B1 | 3/2005 | Faris |
| 6,921,811 B2 | 7/2005 | Zamora et al. |
| 7,033,831 B2 | 4/2006 | Fisk et al. |
| 7,153,684 B1 | 12/2006 | Hogan |
| 7,256,042 B2 | 8/2007 | Rambhatla et al. |
| 7,326,572 B2 | 2/2008 | Fisk et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 9,732,318 B2 | 8/2017 | D'Amour et al. |
| 2002/0072117 A1 | 6/2002 | Xu et al. |
| 2002/0090723 A1 | 7/2002 | Carpenter et al. |
| 2002/0160511 A1 | 10/2002 | Rambhatla et al. |

(Continued)

FOREIGN PATENT DOCUMENTS

| | | |
|---|---|---|
| CA | 2684022 | 9/2014 |
| EP | 0543942 A1 | 6/1993 |

(Continued)

OTHER PUBLICATIONS

Millonig, et al, "Molecular Analysis of the Distal Enhancer of the Mouse Alpha-Fetoprotein Gene" (1995) Mol. Cell Biol. 15: 3848-3856.

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

This disclosure relates to compositions comprising human preprimitive streak cells and/or human mesendoderm cells as well as methods for their production. Additionally, disclosed herein are methods of identifying factors useful in the further differentiation of preprimitive streak and mesendoderm cell types.

18 Claims, 16 Drawing Sheets

(56) References Cited

U.S. PATENT DOCUMENTS

| | | |
|---|---|---|
| 2003/0138948 A1 | 7/2003 | Fisk et al. |
| 2003/0138949 A1 | 7/2003 | Bhushan et al. |
| 2003/0175956 A1 | 9/2003 | Bodnar et al. |
| 2003/0190748 A1 | 10/2003 | Thomson |
| 2003/0224411 A1 | 12/2003 | Stanton et al. |
| 2004/0127406 A1 | 7/2004 | Presnell et al. |
| 2004/0229350 A1 | 11/2004 | Strelchenko et al. |
| 2005/0079159 A1 | 4/2005 | Shastri et al. |
| 2005/0158853 A1 | 7/2005 | D'Amour et al. |
| 2006/0003446 A1 | 1/2006 | Keller et al. |
| 2006/0019387 A1 | 1/2006 | Faris |
| 2006/0040385 A1 | 2/2006 | Itskovitz-Eldor et al. |
| 2006/0040387 A1 | 2/2006 | Fisk et al. |
| 2006/0128018 A1 | 6/2006 | Zwaka et al. |
| 2006/0148081 A1 | 7/2006 | Kelly et al. |
| 2006/0276420 A1 | 12/2006 | Keller et al. |
| 2007/0154984 A1 | 7/2007 | D'Amour et al. |
| 2007/0281355 A1 | 12/2007 | Dalton et al. |
| 2009/0253202 A1 | 10/2009 | D'Amour et al. |

FOREIGN PATENT DOCUMENTS

| | | |
|---|---|---|
| EP | 1298201 A1 | 4/2003 |
| EP | 1627912 A1 | 2/2006 |
| JP | 2004504834 | 2/2004 |
| JP | 2007516728 A | 6/2007 |
| WO | 1998018943 A1 | 5/1998 |
| WO | 1998030679 A1 | 7/1998 |
| WO | 1998043679 A1 | 10/1998 |
| WO | 1999013915 A1 | 3/1999 |
| WO | 2000029442 A1 | 5/2000 |
| WO | 2001051616 A2 | 7/2001 |
| WO | 2002010347 A2 | 2/2002 |
| WO | 2002034880 A2 | 5/2002 |
| WO | 2002059278 A2 | 8/2002 |
| WO | 2003046141 A2 | 6/2003 |
| WO | 2003050249 A2 | 6/2003 |
| WO | 2003100026 A2 | 12/2003 |
| WO | 2004073633 A2 | 9/2004 |
| WO | 2004098490 A2 | 11/2004 |
| WO | 2005017131 A2 | 2/2005 |
| WO | WO2005017131 | 2/2005 |
| WO | 2005033294 A2 | 4/2005 |
| WO | 2005045001 A2 | 5/2005 |
| WO | 2005063971 A2 | 7/2005 |
| WO | 2005097977 A2 | 10/2005 |
| WO | 2005097980 A2 | 10/2005 |
| WO | 2005116073 A2 | 12/2005 |
| WO | 2006016999 A1 | 2/2006 |
| WO | 2006017134 A2 | 2/2006 |
| WO | 2006020919 A2 | 2/2006 |
| WO | 2006034873 A1 | 4/2006 |
| WO | 2006083782 A2 | 8/2006 |
| WO | 2007002210 A2 | 1/2007 |
| WO | 2007047509 A2 | 4/2007 |
| WO | 2007088372 A2 | 8/2007 |
| WO | 2009154606 A1 | 12/2009 |

OTHER PUBLICATIONS

Milne, et al. "Generation of Insulin-Expressing Cells from Mouse Embryonic Stem Cells" (2005) Biochemical and Biophysical Research Communications 328:399-403.

Miyazono et al., "Divergence and convergenence of TGF-beta/BMP signaling", J Cell Physiol (2001) 187:265-276.

Mizusawa at al., "Differentiation Phenotypes of Pancreatic Islet Beta- and Alpha-Cells are Closely Related with Homeotic Genes and a Group of Deferentially Expressed Genes." Gene: An Int. Journal on Genes and Genomes. 331:53-63. (2004).

Mohamed, et al., "B-Catenin Signaling Marks the Prospective Site of Primitive Streak Formation in the Mouse Embryo" Dev. Dynamics 231:416-424 (2004).

Molotkov, A., et al., "Retinoic Acid Generated by Raldh2 in Mesoderm is Required for Mouse Dorsal Endodermal Pancreas Development", Development Dynamics, vol. 232, pp. 950-957, 2005.

Moriya, et al."In Vitro Pancreas Formation from Xenopus Ectoderm Treated with Activin and Retinoic Acid" Develop. Growth Differ. (2000) 42: 593-602.

Munoz-Sanjuan et al., Neural Induction, The Default Model and Embryonic Stem Cells., Nature Reviews, Neuroscience, vol. 3, Apr. 2002 271-280.

Nagai, et al. "The Expression of the Mouse Zic1 , Zic2, and Zic3 Gene Suggests an Essential Role for Zic Genes in Body Pattern Formation" Dev Biol (1997) 182: 299-313.

Nagasawa et al., "Defects of B-cell lymphopoiesis and bone-marrow myelopoiesis in mice lacking the CXC chemokine PSF/SDF-1", Nature (1996) 382:635-638.

Nakagawa, et al., "Recruitment and Activation of Rac1 by the Formation of E-cadherin-mediated Cell-cell Adhesion Sites" J. Cell Science (2001) 114(10): 1829-1838.

Nieto, "The Snail Superfamily of Zinc-Finger Transcription Factors," Nat Rev Mol Cell Biol 3:155-166,2002.

Nieto, et al., "Cloning and Development Expression of Sna, a Murine Homologue of the *Drosophila* snail Gene" Development (1992) 116: 227-237.

Niimi, et al. "SOX7 and SOX17 Regulate the Parietal Endoderm-Specific Enhancer Activity of Mouse Laminin Alpha1 Gene." (2004) J. Biol. Chem. 279 (36): 38055-38061.

Niswander, et al., "Fgf-4 Expression During Gastrulation, Myogenesis, Limb and Tooth Development in the Mouse," Development 114:755-768,1992.

Niwa "Molecular mechanism to maintain stem cell renewal of ES cells", (2001) Cell Struct Funct 26:137-148.

Offield et al., "PDX-1 is Required for Pancreatic Outgrowth and Differentiation of the Rostral Duodenum" Development (1996) 122: 983-995.

Ogura, et al., "Behavioral abnormalities of Zic1 and Zic2 mutant mice: implications as models for human neurological disorders" Behav Genet (2001) 31: 317-324.

O'Hare, et al., "Conditional Immortilization of Freshly Isolated Human Mammary Fibroblast and Endothelial Cells" Proc. Nat. Acad. Sci. (2001) 98: 646-651.

Ohlsson et al., "Embryonic stem cells express growth hormone receptors: regulation by retenoic acid," Endocrinology (1993) 133(6):2897-2903.

Ormestad et al., "Differences in the Embryonic Expression Patterns of Mouse Foxf1 and -2 Match Their Distinct Mutant Phenotypes" Developmental Dynamics (2004) 229: 328-333.

Pauklin et al., Activin/Nodal signaling in stem cells, The Company of Biologists, Development; 2015, 142, 607-619.

Pearce, et al., "Mml, a Mouse Mix-like Gene Expressed in the Primitive Streak," Mech Dev 87:189-192,1999.

Pera, et al., "Regulation of Human Embryonic Stem Cell Differentiation by BMP-2 and its Antagonist Noggin" J Cell Sci (2004) 117: 1269-1280.

Perea-Gomez et al., "Initiation of Gastrulation in the Mouse Embryo is Preceded by an Apparent Shift in the Orientation of the Anterior-Posterior Axis" Curr Biol (2004) 14: 197-207.

Pesce, et al., "Oct-4: Gatekeeper in the Beginnings of Mammalian Development," Stem Cells 19:271-278,2001.

Petropoulos, H, "B-Catenin is Essential and Sufficient for Skeletal Myogenesis in P19 Cells" J. Biol. Chem. vol. 277, No. 18, p. 15393-15399 (2002).

Pevny, et al., "A Role for SOX1 in Neural Determination" Development (1998) 125: 1967-1978.

Phillips at al., "Differentiation of Embryonic Stem Cells for Pharmacological Studies on Adipose Cells." Pharmacological Research. 47:263-268. (2003).

Pownall et al. (2010, FGF Signalling in Vertebrate Development, Morgan & Claypool Life Sciences, 1 pg. printout).

Price et al., "Serum-free media for neural cell cultures," Protocols for Neural Cell Culture, 3rd Ed., Federoff and Richardson (Eds.) Humana Press, Totowa, New Jersey, Chapter 19: 255-264. (1989).

(56) References Cited

OTHER PUBLICATIONS

Rajagopal, et al. "Insulin Staining of ES Cell Progeny from Insulin Uptake" (2003) Science 299:363.
Rambhatla et al. "Generation of Hepatocyte-Like Cells From Human Embryonic Stem Cells." Cell Transplantation (2003), vol. 12, No. 1, p. 1-11.
Ramiya et al. "Reversal of insulin-dependent diabetes using islets generated in vitro from pancreatic stem cells," Nature Medicine (2000) 6:278-282.
Reijo et al. (2009, Differentiation, vol. 78, pp. 18-23).
Reijo et al., Gene expression profiles of human inner cell mass cells and embryonic stem cells, Differentiation, (2009) vol. 78, pp. 18-23.
Reubinoff et al., "Embryonic stem cell lines from human blastocysts: somatic differentiation in vitro", (2000) Nat Biotechnol 18:399-404.
Reue, "mRNA quantitation techniques: considerations for experimental design and application," The Journal of Nutrition, (1998) 128(11):2038-2044.
Robb, L. & Tam, P.P. Gastrula organiser and embryonic patterning in the mouse. Semin Cell Dev Biol 15, 543-554 (2004).
Robertson, "Teratocarcinomas and embryonic stem cells: A practical approach," IRL Press 1987.
Roche et al. "Ectodermal commitment of insulin-producing cells derived from mouse embryonic stem cells" Faseb J (2005) 19: 1341-3.
Rodaway et al., "Induction of the mesendoderm in the zebrafish germ ring by yolk cell-derived TGF-beta family signals and discrimination of mesoderm and endoderm by FGF", (1999) Development 126:3067-3078.
Rodaway et al., "Mesendoderm, an ancient germ layer?", (2001) Cell 105:169-172.
Rohr et al., "Zebrafish zic1 expression in brain and somites is affected by BMP and hedgehog signaling", Mech Dev, (1999) 85:147-159.
Rossant, J. & Tam, P.P. Emerging asymmetry and embryonic patterning in early mouse development. Dev Cell 7, 155-164 (2004).
Sander, et al., "The Beta Cell Transcription Factors and Development of the Pancreas," J Mol Med. 75:327-40,1997.
Sasaki et al., "Differential expression of multiple fork head related genes during gastrulation and axial pattern formation in the mouse embryo", Development, (1993) 118:47-59.
Schier et al., "Nodal signalling in vertebrate development," Nature, (2000) 403(6768):385-9.
Schier, A. F. (2003). Nodal signaling in vertebrae development Annu Rev Cell Dev Biol 19, 589-621.
Schmolke et al. (1998). Identification of hepatitis G virus particles in human serum by E2-specific monoclonal antibodies generated by DNA immunization. J. Virol. 72: 4541-4545.
Tyagi et al. "Molecular beacons: probes that fluoresce upon hybridization," Nat. Biotechnol., (1996) 14(3):303-8.
U.S. Appl. Nos. 60/587,942, 60/586,566 and60/532,004.
Ulivieri et al. (1996). Generation of a monoclonal antibody to a defined portion of the Heliobacter pylori vacuolating cytotoxin by DNA immunization. J. Biotechnol. 51: 191-194.
Urbach et al. "Modeling Lesch-Nyhan Disease by Gene Targeting in Human Embryonic Stem Cells" (2004) Stem Cells 22:635-641.
Valdimarsdottir et al., "Functions of the TFGb superfamily in human embryonic stem cells," APMIS (2005) 113(11-12):773-89.
Vale et al. (1986, Nature, vol. 321, pp. 776-779).
Vallier et al. "Activin/Nodal and FGF Pathways Cooperate to Maintain Pluripotency of Human Embryonic Stem Cells" (2005) J Cell Sci. 118: 4495-509.
Vallier et al. "Nodal Inhibits Differentiation of Human Embryonic Stem Cells Along the Neuroectodermal Default Pathway" (2004) Developmental Biology 275, 403-421.
Vandescompele, et al., "Accurate Normalization of Real-Time Quantitative RT-PCR Data by Geometric Averaging of Multiple Internal Control Genes" Genome Biol (2002) 3(7):1-12.
Varlet et al., "Nodal exprssion in the primitive endoderm is required for specification of the anterior axis during mouse gastrulation", Development, (2003) 124:1033-1044.
Vincent et al., "Cell fate decisions within the mouse organizer are governed by graded nodal signals", Genes Dev, (2003) 17:1646-1662.
Vogel, "Stem Cells are Coaxed to Produce Insulin," Science. 292:615-616,2001.
Wang et al., "Self-renewal of human embryonic stem cells requires insulin-like growth factor-1 receptor and ERBB2 receptor signaling," Blood (2007) 110:4110-4119.
Wei et al. "Transcriptome Profiling of Human and Murine ESCs Identifies Divergent Paths Required to Maintain the Stem Cell State"(2005) Stem Cells 23:166-185.
Weiler-Guettler, et al., "Developmentally Regulated Gene Expression of Thrombomodulin in Postimplantation Mouse Embryos" Development (1996) 122: 2271-2281.
Weiler-Guettler, et al., "Thrombomoduiatin gene regulation by cAMP and retinoic acid in F9 embryonal carcinoma cells," PNAS 89:2155-9,1992.
Weinstein, D.C. et al. The winged-helix transcription factor HNF-3 beta is required for notochord development in the mouse embryo. Cell 78, 575-588 (1994).
Wells, et al., "Vertebrate endoderm development," Annu Rev Cell Dev Biol.:393-410,1999.
Wells, J. M. and Melton, D. A. "Early Mouse Endoderm is Patterned by Soluble Factors From Adjacent Germ Layers" Development (2000) 127: 1563-1572.
Wilding et al., "The Role of pdx1 and HNF6 in Proliferation and Differentiation of Endocrine Precedures" Diabetes Metab Res Rev. (2004) 20(2): 114-23.
Wiles and Johansson, "Embryonic Stem Cell Development in a Chemically Defined Medium," Experimental Cell Research (1999) 247:241-248.
Willert, et al., Wnt Proteins are lipid-modified and can act as stem cell growth factors, Nature, 423, 448-452, 2003.
Willison, "The mouse Brachyury gene and mesoderm formation", Trends Genet, (1990) 6:104-105.
Wilson et al., "Streptozotocin interactions with pancreatic beta cells and the induction of insulin-dependent dependent diabetes," Current Topics Microbiol. Immunol. (1990) 158:27-54.
Wu et al., "The ligation amplification reaction (LAR)—amplification of specific DNA sequences using sequential rounds of template-dependent ligation.," Genomics, (1989): 4(4):560-9.
Xu et al., "Characterization and Enrichment of Cardiomyocytes Derived From Human Embryonic Stem Cells." Cellular Biology. 91:501-508. (2002).
Xu et al., "Feeder-free growth of undifferentiated human embryonic stem cells," Nat. Biotechnol. (2001) 19 (10):971.
Xu, et al. "BMP4 Initiates Human Embryonic Stem Cell Differentiation to Trophoblast." Nature Biotechnology (Dec. 2002), vol. 20, pp. 1261-1264.
Yamaguchi, et al., "flk-1, an flt-related Receptor Tyrosine Kinase is an Early Marker for Endothelial Cell Precursors" Development (1993) 118: 489-498.
Yamaguchi, et al., "T (Brachyury) is a Direct Target of Wnt3a During Paraxial Mesoderm Specification" Genes Dev (1999)13: 3185-3190.
Yang, D.H. et al. Disabled-2 is essential for endodermal cell positioning and structure formation during mouse embryogenesis. Dev Biol 251, 27-44 (2002).
Yantiss, et al. "Prevalence and Prognostic significance of acinar cell differentiation in pancreatic endocrine tumors", American Journal of Surgical Pathology, vol. 26, No. 7, Jul. 2002 pp. 893-901.
Yasunaga Masahiro et al., "Induction and monitoring of definitive and visceral endoderm differentiation of mouse ES cells." Nature Biotechnology. Dec. 2005, vol. 23, No. 12, pp. 1542-1550.
Ying et al., "BMP induction of Id proteins suppresses differentiation and sustains embryonic stem cell self-renewal in collaboration with STAT3," Cell (2003) 115:281-292.
Yu et al., "Human induced pluripotent stem cells free of vector and transgene sequences", (2009), Science, 324(5928):797-801.
Yusuf et al. Expression of chemokine receptor CXCR4 during chick embryo development. Anat Embryol (Berl). 210(1): 35-41, 2005.

(56) References Cited

OTHER PUBLICATIONS

Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao, G. Q. (2003). Consequences of knocking out BMP signaling in the mouse. Genesis 35, 43-56.
Zhou et al., "Nodal is a novel TGF-beta-like gene expressed in the mouse node during gastrulation", Nature, (1993) 361:543-547.
Zwaka, et al. "Homologous Recombination in Human Embryonic Stem Cells" Nature Biotechnology (2003) 21: 319-321.
Schoenwolf et al., "Gastrulation and early mesodermal patterning in vertebrates", Methods Mol Biol, (2000) 135:113-125.
Schuldiner et al. (2000). Effects of Eight Growth Factors on the Differentiation of Cell Derived from Human Embryonic Stem Cells. Proc. Natl. Sci., vol. 97, 11307-11312.
Schwartz et al. "Defined Conditions for Development of Functional Hepatic Cells from Human Embryonic Stem Cells" Stem Cells and Development (2005) 14(6): 643-655.
Segev et al., "Differentiation of Human Embryonic Stem Cells into Insulin-Producing Clusters", Stem Cells, (2004) 22:265-274.
Shalaby, et al., "Failure of Blood-Island Formation and Vasculogenesis in Flk-1-deficient Mice" Nature (1995) 376: 62-66.
Shamblott et al., "Human embryonic germ cell derivatives express a broad range of developmentally distinct markers and proliferate exensively in vitro," Proc. Natl. Acad. Sci. USA (2001) 98(1):113-8.
Shamblott, et al., "Derivation of Pluripotent Stern Cells From Cultured Human Primordial Germ Cells" Proc Nat Acad Sci USA (1998) 95: 13726-13731.
Shapiro et al., "Could fewer islet cells be transplanted in type 1 diabetes? Insulin independence should be dominant force in islet transplantation", BMJ (2001) 322:861.
Shapiro et al., "Islet transplantation in seven patients with type 1 diabetes mellitus using a glucocorticoid-free immunosuppressive regimen", N. Engl J Med, (2000) 343:230-238.
Shapiro et al., "Pancreatic islet transplantation in the treatment of diabetes mellitus", Best Pract Res Clin Endocrinol Metab (2001) 15:241-264.
Shi et al., "Inducing embryonic stem cells to differentiate into pancreatic beta cells by a novel three-step approach with activin A and all-trans retinoic acid," Stem Cells (2005) 23:656-662.
Shiozawa et al., "Cloning and characterization of Xenopus laevis xSox 7 xDNA", Biochim Biophys Acta (1996) 1309:73-76.
Shirahashi et al., "Differentiation of Human and Mouse Embryonic Stem Cells Along a Hepatocyte Lineage" Cell Transplantation (2004) 13:197-211.
Shiraki, "TFG-.beta. Signaling Potentiates Differentiation of Embryonic Stem Cells to Pdx-1 Expressing Endodermal Cells", Genes to Cells, (2005) 21, 405-412.
Shook, D. & Keller, R. Mechanisms, mechanics and function of epithelial-mesenchymal transitions in early development. Mech Dev 120, 1351-1383 (2003).
Sinner, D., Rankin, S., Lee, M. & Zorn, A.M. Sox17 and beta-catenin cooperate to regulate the transcription of endodermal genes. Development 131, 3069-3080 (2004).
Skoudy, A., et al. "Transforming Growth Factor (TGF) beta, Fibroblast Growth Factor (FGF) and Retinoid Signaling Pathways Promote Pancreatic Exocrine Gene Expression in Mouse Embryonic Stem Cells." The Biochemical Journal. May 1, 2004, vol. 379, No. Pt 3, pp. 749-756.
Smith, "Brachybury and the T-box genes," Curr. Opin. Genet. Dev., (1997) &;474-480.
Sooknanan et al., "NASBA: a detection and amplification system uniquely suited for RNA," Nature Biotechnology, (1995) 13:563-564.
Smith, et al., "Upstream and downstream from Brachyury, a gene required for vertebrae mesoderm formation," Cold Spring Harb Symp Quant Biol. 62:337-46,1997.
Soon-Shiong, "Treatment of Type I Diabetes using Encapsulated Islets," Adv Drug Deliv Rev. 35:259-270,1999.

Soda et al Insulin-secreting cells derived from embryonic stem cells normalize glycemia in streptozotocin-induced diabetic mice Diabetes Feb. 2000;49(2):157-62.
Stafford et al., "A conserved role for retold signaling in verterbrate pancreas development", Dev Genes Evol., vol. 214, pp. 432-441, 2004.
Stafford, D. and Prince, V. (2002). Retinoic Acid Signaling is Required for a Critical Early Step in Zebrafish Pancreatic Development, Current Biology, vol. 12, 1215-1220, Jul. 23, 2002.
Stafford, D. and Prince, V., "The Role of Retinoid Signaling in Pancreas Differentiation" Pancreatic Development, Proliferation and Stem Cells, Meeting Abstract, Oct. 18-19, 2001, National Institute of Health.
Stainier, "A Glimpse into the Molecular Entrails of Endoderm Formation," Genes Dev 16:893-907,2002.
Stemmler, et al., "Analysis of Regulatory Elements of E-Cadherin with Reporter Gene Constructs in Transgenic Mouse Embryos" Developmental Dynamics (2003) 227: 238-245.
Stoffers, D.A., et al., "Pancreatic agenesis attributable to a single nucleotide deletion in the human IPF1 gene coding sequence", Nature Genetics, vol. 15, pp. 106-110, 1997.
Stoffers, et al., "Early-onset Type-II Diabetes Mellitus (MODY4) Linked to IPF1" Nature Genetics (1997) 17: 138-139.
Sun, et al., "Targeted Disruption of Fgf8 Causes Failure of Cell Migration in the Gastrulating Mouse Embryo" Genes Dev (1999) 13: 1834-1846.
Sun, X. et al. Conditional inactivation of Fgf4 reveals complexity of signalling during limb bud development. Nat Genet 25, 83-86 (2000).
Suzuki, et al., "Cloned Cells Develop Renal Cortical Collecting Tubules" Nephron. (1994) 68: 118-124.
Tada, et al. "Characterization of Mesendoderm: A Diverging Point of the Definitive Endoderm and Mesoderm in Embryonic Stem Cell Differentiation Culture." (2005) Development 132: 4363-4374.
Takahashi et al., "Induction of pluripotent stem cells from adult human fibroblasts by defined factors", Cell (2007), 131(5):861-872.
Takash et al., "SOX7 transcription factor: sequence, chromosomal localization, expression, transactivation and interference with Wnt signaling", Nucleic Acids Res, (2001) 29:4274-4283.
Tam et al. Early endoderm development in vertebrates: lineage differentation and morphogenetic function. Curr Opin Genet Dev. 13(4): 393-400, 2003.
Tam et al., "Gene function in mouse embryogenesis: get set fir gastrulation," Nat. Rev. Genet. (2007) 8(5):368-81.
Tam, P.P. & Behringer, R.R. "Mouse gastrulation: the formation of a mammalian body plan", Mechanisms of Development, 68(1-2): 3-25, 1997.
Taniguchi et al., "Isolation and characterization of a mouse SRY-related cDNA, mSox7", Biochim Biophys Act, (1999) 1445:225-231.
Technau, "Brachyury, the blastopore and the evolution of the mesoderm", Bioessays, (2001) 23:788-794.
Terskikh et al., ""Peptabody": a new type of high avidity binding protein," Proc. Natl Acad. Sci. USA, (1997) 94(5):1663-8.
Thelwell et al., "Mode of action and application of Scorpion primers to mutation detection," Nucleic Acids Res., (2000) 28(19):3752-61.
Thisse et al., "Antivin, a novel and divergent member of the TGF-superfamily, negatively regulates mesoderm induction," Development (1999) 126(2):229-40.
Thomas, et al., "The Murine Gene, Traube, Is Essential for the Growth of Preimplantation Embryos" Dev Biol (2000) 227: 324-34 . . . .
Thomson et al. "Embryonic Stem Cell Lines Derived from Human Blastocysts." Science ( Nov. 1998); 282 (5391): pp. 1145-1147.
Tiedemann et al., "Pluripotent cells (stem cells) and Their Determination and Differentiation in Early Vertebrate Embryogenesis." Develop. Growth Differ. 43:469-502, (2001).
Tomita Tatsuo, "New Markers for Pancreatic Islets and Islet Cell Tumors", Pathology International, vol. 52, No. 7, Jul. 2002, pp. 425-432.
Tremblay KD et al.,Formation of the definitive endoderm in mouse is a Smad2-dependent process.Development. Jul. 2000;127(14):3079-90.Abstract, 1-25.

(56) References Cited

OTHER PUBLICATIONS

Trueba et al. PAX8, TITF1, and FOXE1 gene expression patterns during human development: new insights into human thyroid development and thyroid dysgenesis-associated malformations. J Clin Endocrinol Metab. Jan. 2005; 90(1):455-62, 2005.
Turnpenny, L., et al., "Evaluating Human Embryonic Germ Cells: Concord and Conflict as Pluripotent Stem Cells," Stem Cells, 2006:24:212-220.
Jonsson, J., et al., "Insulin-promoter-factor 1 is required for pancreas development in mice", Nature, vol. 371. pp. 606-609, (1994).
Kahan, B.W. et al. "Pancreatic Precursors and Differentiated Islet Cell Types from Murine Embryonic Stem Cells: An in Vitro Model to Study Islet Differentiation." Diabetes. Aug. 2003, vol. 52, No. 8, pp. 2016-2024.
Kalinchenko, et al., "The Forkhead Box F1 Transcription Factor is Expressed in Brain and Head Mesenchyme During Mouse Embryonic Development," Gene Expr Patterns 3:153-158,2003.
Kanai-Azuma, M., Kanai, Y., Gad, J.M., Tajima, Y., Taya, C., Kurohmaru, M., Sanai, Y., Yonekawa, H., Yazaki, K., Tam, P.P., and Hayashi, Y. (2002). Depletion of definitive gut endoderm in Sox17-null mutant mice. Development 129, 2367-2379.
Katoh, "Expression of human SOX7 in normal tissues and tumors", Int J Mol Med, (2001) 9:363-368.
Kawahira, et al., "Hedgehog Signaling Regulates Expansion of Pancreatic Epithelial Cells" Developmental Biology (2005) 280: 111-121.
Kawaji, et al. "Exploration of Novel Motifs Derived from Mouse cDNA Sequences" Genome Research (2002) 12: 367-378.
Keller GM, "In vitro differentiation of embryonic stem cells," Curr Op Cell Biol (1995) 7:862-869.
Khoo, et al., "Growth and Differentiation of Embryoid Bodies Derived from Human Embryonic Stem Cells: Effect of Glucose and Basic Fibroblast Growth Factor", Biology of Reproduction (2005) 73: 1147-1156.
Kieffer, T.J., and J.F. Habener, "The Glucagon-Like Peptides" Endocrinology Reviews (1999) 20(6): 876-913.
Kikuchi et al., "Casanova encodes a novel Sox-related protein necessary and sufficient for early endoderm formation in zebrafish", Genes Dev, (2001) 15:1493-1505.
Kilpatrick et al. (1998). Gene gun delivered DNA-based immunizations mediate rapid production of murine monoclonal antibodies to the Flt-3 receptor. Hybridoma 17: 569-576.
Kim et al., "Chemokines: signal lamps for trafficking of T and B cells for development and effector function", J Leukoc Biol, (1999) 65:6-15.
Kim et al., Pancreas development is promoted by cyclopamine, a Hedgehog signaling inhibitor, Proc. Natl. Acad. Sci. USA vol. 95, pp. 13036-13041, Oct. 1998.
Kimelamn et al. (2000, Current Opinion & Development, vol. 10, pp. 350-356).
Kimelman, D., and Giffin, K. J. (2000). Vertebrae mesendoderm induction and patterning, Curr Opin Genet Dev 10, 350-356.
Kimmel et al., "Preparation of cDNA and the generation of cDNA libraries: overview," Methods Enzymol., (1987) 152:307-16.
Kinder, et al., "The Organizer of the Mouse Gastrula is Composed of a Dynamic Population of Progenitor Cells for the Axial Mesoderm" Development (2001) 128: 3623-3634.
Kohler et al., "Continuous cultures of fused cells secreting antibody of predefined specificity," Nature, (1975) 256(5517) 495-7.
Krasemann et al. (1999). Generation of monoclonal antibodies against proteins with an unconventional nucleic acid-based immunization strategy. J. Biotechnol. 73: 119-129.
Kroon et al., "Pancreateic endoderm derived from human embryonic stem cells generates glucose-responsive insultin-secreting cells in vivo", Nat. Biotechnol. (2008) 26(4):443-52.
Kubo, et al., "Development of definitive endoderm from embryonic stem cells in culture" Development (2004)131: 1651-1662.
Kumar et al., "Nodal signaling uses activin and transforming growth factor-beta receptor-regulated Smads", J Biol Chem, (2001) 276: 656-661.
Kuo et al., "Roles of histone acetyltransferases and deacetylases in gene regulation", BioEssays, (1998) 20:615-626.
Kwoh et al., "Transcription-based amplification system and detection of amplified human immunodeficiency virus type 1 with a bead-based sandwich hybridization format," Proc. Natl. Acad. Sci. USA, (1989) 86(4):1173-7.
Labosky et al., "Embryonic germ cell lines and their derivation from mouse primordial germ cells", Ciba Found Symp, (1994) 182:157-168; discussion 168-178.
Labosky, et al., "Mouse Embryonic Germ (EG) Cell Lines: Transmission Through the Germline and Differences in the Methylation Imprint of Insulin-Like Growth Factor 2 Receptor (Igf2r) Gene Compared With Embryonic Stem (ES) Cell Lines" Development (1994) 120: 3197-3204.
Landegren et al., "A ligase-mediated gene detection technique," Science, (1988) 241(4869):1077-80.
Latif et al., "A Simple Method of Staining Fresh and Cultured Islets," Transplantation (1998) 45(4): 827-830.
Lawson, et al., "Bmp4 is Required for the Generation of Primordial Germ Cells in the Mouse Embryo" Genes Dev (1999) 13: 424-436.
Levenberg, et al., Differentiation of human embryonic stem cells on three-dimensional polymer scaffolds, PNAS, Oct. 28, 2003, vol. 100, No. 22, 12741-12746.
Li, et al., "Selective agenesis of the dorsal pancreas in mice lacking homeobox gene Hlxb9" Nature Genetics (1999) 23: 67-70.
Hickert et al., "Formation of multiple hearts in mice following deletion of beta-catenin in the embryonic endoderm", Dev Cell (2002) 3:171-181.
Liu, et al., "Requirement for Wnt3 in Vertebrate Axis Formation" Nat Genet (1999) 22: 361-365.
Loebel et al., "A gut feeling," Nat. Biotechnol. (2005) 23(12):1491-2.
Loebel et al., "Lineage choice and differentiation in mouse embryos and embryonic stem cells," Developmental Biology 264 pp. 1-14 Dec. 2003.
Lomeli et al., "Quantitative assays based on the use of replicatable hybridization probes," Clin. Chem., (1989) 35(9):1826-31.
Lowe et al., "Genetic dissection of nodal function in patterning the mouse embryo," Development, (2001) 128:1831-1843.
Lu, C. C., Brennan, J., and Robertson, E. J. (2001). From fertilization to gastrulation: axis formation in the mouse embryo. Curr Opin Genet Dev 11, 384-392.
Lumelsky, et al., "Differentiation of Embryonic Stem Cells to Insulin-Secreting Structures Similar to Pancreatic Islets" Science (2001) 292: 1389-1394.
Ma et al., "The chemokine receptor CXCR4 is required for the retention of B lineage and granulocytic precursors within the bone marrow microenvironment, Immunity", (1999) 10:463-471.
Mark et al., "Function of retinoid nuclear receptors: lessons from genetic and pharmacological dissections of the retinoic acid signaling pathway during mouse embryogenesis," Annu. Rev. Pharmacol. Toxicol. (2006) 46:451-80.
Martin, et al., "Dorsal Pancreas Agenesis in Retinoic Acid-Deficient Raldh2 Mutant Mice" Developmental Biology (2005) 284: 399-411.
Maruoka, et al., "Comparison of the Expression of Three Highly Related Genes, Fgf8, Fgf17 and Fgf18, in the Mouse Embryo" Mech Dev (1998) 74: 175-177.
Matsubara, Kousaku, et al. "Acute lymphoblastic leukemia with coexpression of CD56 and CD57: Case reports", Pediatric Hematology and Oncology, vol. 21, No. 7, Oct. 2004, pp. 677-682.
Matsuda T, et al. "STAT3 Activation is Sufficient to Maintain an Undifferentiated State of Mouase Embryonic Stem Cells" (Aug. 2, 1999) EMBO J, 18(15):4261-9.
McGrath et al, "Expression of Homeobox Genes, including and insulin Promoting Factor, in the Murine York Sac at the Time of Hematopoietic Initiation" (1997) Mol Reprod Dev 48:(2) pp. 145-153.
McGrath et al., "Embryonic expression and function of the chemokine SDF-1 and its receptor, CXCR4", Dev Biol. (1999) 213:442-456.
McLean et al. "Activin A Efficiently Specifies Definitive Endoderm from Human Embryonic Stem Cells Only When Phosphtidylinositol 3-Kinase Siognaling is Suppressed" (2007) Stem Cells 25: 29-38.

(56) References Cited

OTHER PUBLICATIONS

Micallef Suzanne, et al. "Retinoic Acid induces Pdx1-positive Endoderm in Differentiating mouse embryonic stem cells." Diabetes. Feb. 2005, vol. 54, No. 2, pp. 301-305.
Abe et al., "Endoderm-Specific Gene Expression in Embryonic Stem Cells Differentiated to Embryoid Bodies." Experimental Cell Research. (1996) 229(1): 27-34.
Activin A, Product Information from Sigma-Aldrich (2 pages).
Alexander et al., "Casanova plays an early and essential role in endoderm formation in zebrafish," Dev Biol, (1999) 215:343-357.
Alexander, J., and Stainier, D. Y., "A Molecular Pathway Leading to Endoderm Formation in Zebrafish" Curr Biol (1999) 9:1147-1157.
Ang et al., "HNF-3beta is essential for node and notochord formation in mouse development," Cell, (1994) 78:561-574.
Ang et al., "The Formation and Maintenance of the Definitive Endoderm Lineage in the Mouse: Involvement of HNF3/forkhead Proteins." Development, 119:1301-1315. (1993).
Aoki, et al. "Regulation of Nodal Signalling and Mesendoderm Formation by TARAM-A, A Tgfbeta-Related Type I Receptor" Dev Biol (2002) 241: 273-288.
Arnold et al., "Brachyury is a target gene of the Wnt/beta-catenin signaling pathway," Mech. Dev., (2000) 91:249-258.
Assady et al. "Insulin production by human embryonic stem cells" (2001) Diabetes 50(8): 1691-1697.
Bachiller et al., "The organizer factors chordin and noggin are required for mouse forebrain development," Nature, (2000) 403:658-661.
Bain et al., "Embryonic Stem Cells Express Neuronal Properties in Vitro." Developmental Biology, 168:342-357 (1995).
Barbacci, et al. "Variant Hepatocyte Nuclear Factor 1 is Required for Visceral Endoderm Specification" (1999) Development 126:4795-4805.
Barringer et al., "Blunt-end and single-strand ligations by *Escherichia coli* ligase: influence on an in vitro amplification schemem," Gene, (1990) 89(1):117-22.
Barry et al. "Production of monoclonal antibodies by genetic immunization." Biotechniques 16 : 616-620. (1994).
Batlle, E. et al. The transcription factor snail is a repressor of E-cadherin gene expression in epithelial tumour cells. Nat Cell Biol 2, 84-89 (2000).
Beck, et al., "Extra-embryonic proteases regulate Nodal signaling during gastrulation," Nat Cell Biol 4:981-985,2002.
Beddington et al., "Brachyury—a gene affecting mouse gastrulation and easly organogenesis," Dev Suppl, (1992) 157-165.
Bendell et al., "IGF and FGF cooperatively establish regulatory stem cell niche of pluripotent human cells in vitro," Nature (2007) 448:1015-1021.
Bhatia, Mickie, Embryonic Stem Cells Come of Age, J Exp Med, 206: 2056-7 Sep. 28, 2009.
Blum et al., "Gastrulation in the mouse: the role of the homebox gene goosecoid," Cell, (1992) 69:1097-1106.
Bongso et al., "Isolation and culture of inner cell mass cells from human blastocysts," Hum Reprod (1994) 9:2110-2117.
Bordonaro et al., "Cell type—a promoter-dependent modulation of the Wnt signaling pathway by sodium butyrate," Int. J. Cancer (2002) 97(1):42-51.
Bost et al., "Retinoic Acid Activation of the ERK Pathway is Required for Embryonic Stem Cell Commitment into the Adipocyte Lineage." Biochem. J. 361:621-627. (2002).
Brennan et al., "Nodal signalling in the epiblast patterns the early mouse embryo," Nature, (2001) 411:965-969.
Brunt, "Amplifying genes: PCR and its alternatives," Biotechnology, (1990) 8(4):291-4.
Candia et al., "Differential localization of mox-1 and mox-2 proteins indicates distinct roles during development," , Int.J. Dev. Biol. (1996), 40:1179-1184.
Candia, A.F. & Wright, C.V. Differential localization of Mox-1 and Mox-2 proteins indicates distinct roles during development. Int J Dev Biol 40, 1179-1184 (1996).

Carpenter, et al. "Enrichment of Neurons and Neural Precursors From Human Embryonic Stem Cells" Experimental Neurology (2001) 172: 383-397.
Cereghini, et al. "Expression Patterns of vHNF1 and HNF1 Homeoproteins in Early Postimplantation Embryos Suggest Distinct and Sequential Developmental Roles" (1992) Development 116:783-797.
Chang, H., Brown, C. W., and Matzuk, M. M. (2002). Genetic analysis of the mammalian transforming growth factor-beta superfamily. Endocr Rev 23, 787-823.
Chen at al.,"Retinoic acid signaling is essential for pancreas development and promotes endocrine at the expense of exocrine cell differentiation in Xenopus", Developmental Biology 271,144-160, 2004.
Chen et al., "Suppression of ES cell differentiation by retinol (vitamin A) via the overexpression of Nanog," Differentiation (2007) 75(8):682-93.
Chen, et al., Two Modes by which Lefty Proteins Inhibit Nodal Signaling; Current Biology, vol. 14, 618-624, Apr. 6, 2004.
Chin et al., "Induced pluripotent stem cells and embyronic stem cells are distinguished by gene expression signatures," Cell Stem Cell (2009) 5(1):111-23.
Ciani et al., "WNTs in the vertebrate nervous system: from patterning to neuronal connectivity," Nat. Rev. Neurosci. (2005) 6(5):351-62.
Ciruna et al., "Chimeric analysis of fibroblast growth factor receptor-1 (Fgfr1) Function: a role for FGFR1 in morphogenetic movement through the primitive streak," Development, (1997) 124:2829-2841.
Ciruna et al., "FGF signaling regulates mesoderm cell fate specification and morphogenetic movement at the primitive streak," Development, (1997) 124:2829-2841.
Clackson et al., "Making antibody fragments using phage display libraries," Nature, (1991) 352(6336):624-8.
Collombat et al., "Specifying pancreatic endocrine cell fates," Mech. Dev. (2006) 123(7):501-12.
Conley et al. "BMPs Regulate Differentiation of a Putative Visceral Endoderm Layer Within Human Embryonic Stem-Cell-Derived Embryoid Bodies" (2007) Biochem Cell Biol 85: 121-132.
Conlon, et al., "A primary requirement for nodal in the formation and maintenance of the primitive streak in the mouse" Development (1994) 120: 1919-1928.
Costaglia et al. (1998) Genetic immunization against the human thyrotropin receptor causes thyroiditis and allows production of monoclonal antibodies recognizing the native receptor. J. Immunol. 160:1458-1465.
Czyz et al. "Embryonic Stem Cell Differentiation: The Role of Extracellular Factors" (2001)Differentiation 68(4-5):167-174.
Daheron et al. "LIF/STAT3 Signaling Fails to Maintain Self-Renewal of Human Embryonic Stem Cells" Stem Cells (2004) 22: 770-778.
D'Amour et al. "Production of pancreatic hormone-expressing endocrine cells from human embryonic stem cells" (Nov. 1, 2006) Nature Biotechnology 24, 1392-1401.
D'Amour et al., "Efficient differentiation of human embryonic stem cells to definitive endoderm.", Nature Biotechnology. 23:1534-41 (2005).
Dang et al. "Controlled, scalable embryonic stem cell differentiation culture," Stem Cells, (2004) 22:275-282.
Dani et al., "Differentiation of Embryonic Stem Cells into Adipocytes in Vitro." Journal of Cell Science. 110:1279-1285 (1997).
Database UniProt, "1-acyl-sn-glycerol-3-phosphate acyltransferase gmma (EC 2.3.1.51) (1-AGP acyltransferase 3) (1-AGPAT 3) (Lyspohosphatidic acid acyltransfearse gamma) (LPAAT-gamma) (1-acylglycerol-3-phosphate 0-acyltransfearse 3)" retrieved from EBI accession No. UNIPROT: Q9NRZ7 on Oct. 1, 2000.
De Caestecker, "The transforming growth factor-beta superfamily of receptors," Cytokine Growth Factor (2004) Rev 15:1-11.
De Felice, et al., "TTF-1 Phosphorylation is Required for Peripheral Lung Morphogenesis, Perinatal Survival, and Tissue-Specific Gene Expression" J. Biological Chemistry (2003) 278(37): 35574-35583.
Dottori, et al., "Neural Differentiation of Human Embryonic Stem Cell" Methods Mol Biol. (2008) 438: 19-30.

(56) References Cited

OTHER PUBLICATIONS

Dougan et al., "The role of the zebrafish nodal-related genes squint and Cyclops in patterning of mesendoderm", Development (2003) 130:1837-1851.
Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.
Dudas et al., "The homeobox transcription factor Prox1 is highly consented in embryonic hepatoblasts and in adult and transformed hepatocytes, but is absent from bile duct epithelium," Ant. Embryol. (Berl) (2004).
Edlund, H., "Factors Controlling Pancreatic Cell Differentiation and Function," Diabetologia (2001) 44(9): 1071-1079.
Elghanian et al., "Selective Colorimetric Detection of Polynucleotides Based on the Distance-Dependent Optical Properties of Gold Nanoparticles ," Science, (1997) 277(5329):1078-1081.
Elms et al., "Overlapping and distinct expression domain of Zic2 and Zic3 during mouse gastrulation," Gene Expression Patterns, (2004) 4:505-511.
Extended European Search Report dated Jun. 19, 2013 for European Patent Application No. EP10013206.7, 8 pages.
Falasca, et al., "Retinoic Acid Treatment Induces Apoptosis or Expression of a More Differentiated Phenotype on Different Fractions of Cultured Fetal Rat Hepatocytes" Hepatology (1998) 28(3): 727-737.
Fehling et al., "Development and Disease: Tracking Mesoderm Induction and its Specification to the Hemangioblast during Embryonic Stem Cell Differentiation." Development. 130:4217-4227. (2003).
Feldman et al., "Zebrafish organizer development and germ-layer formation require nodal-related signals", Nature (1998) 395:181-185.
Feng et al "HIV-1 entry cofactor functonal cDNA cloning of a seven-ransmembrane G protein-coupled receptor", Science (1996) 272:872-877.
Freund, et al. "Insulin Redirect Differentiation from Cardiogenic Mesoderm and Endoderm to Neuroectoderm in Differentiating Human Embryonic Stem Cells", Stem Cells, 2008, vol. 26(3), 724-733.
Futaki et al., "Molecular basis of constitutive production of basement membrane components: Gene expression profiles of engelbreth-holm-swarm tumor and F9 embryonal carcinoma cells", J Biol. Chem., (2003) 50691-701.
Gardner, "Stem cells and regenerative medicine: principles, prospects and problems," C.R. Biol. (2007) 330(6-7):465-73.
Goumans et al., "Mouse Embryonic Stem Cells with Aberrant Transforming Growth Factor B signaling Exhibit Impaired Differentiation in Vitro and in Vivo." Differentiation. 63:103-113. (1998).
Grapin-Botton, "Endoderm development: from patterning to organogenesis," Trends Genet. 16:124-30,2000.
Guatelli et al., "Isothermal, in vitro amplification of nucleic acids by a multienzyme reaction modeled after retroviral replication," Proc. Natl. Acad. Sci. USA, (1990) 87(5):1874-8.
Gupta et al., "Pharmacological evidence for complex and multiple site interaction of CXCR4 with SDF-1alpha: implications for development of selective CXCR4 antagonists", Immunol. Lett., (2001), 78(1):29-34.
Haegel, et al., "Lack of .beta.-catenin Affects Mouse Development at Gastrulation" Development (1995) 121: 3529-3537.
Hallonet, et al., "Maintenance of the Specification of the Anterior Definitive Endoderm and Forebrain Depends on the Axial Mesendoderm: A Study Using HNF3.beta./Foxa2 Conditional Mutants" Dev Biol (2002) 243: 20-33.
Hamazaki et al. "Hepatic Maturation in Differentiating Embryonic Stem Cells in Vitro." Febs Letter, Elsevier Science Publishers, Amsterdam, NL, vol. 497, No. 1: 15-19, 2001.
Hansson, et al. "Artifactual Insulin Release from Differentiated Embryonic Stem Cells" (2004) Diabetes 53:2603-2609.

Hards, T. M., and Childs, G. (2002). Global gene expression patterns during differentiation of F9 embryonal carcinoma cells into parietal endoderm. Funct Integr Geneomics 2, 105-119.
Harrision, et al., "Pancreas Dorsal Lobe Agenesis and Abnormal Islets of Langerhans in HIxb9-deficient Mice," Nature Genetics 23:71-75,1999.
Hart et al., 2004, Developmental Dynamics, vol. 230, pp. 187-198.
Haumaitre, et al. "Functions of HNF1 Family Members in Differentiation of the Visceral Endoderm Cell Lineage" (2003) J. Biol. Chem. 278 (42): 40933-40942.
Henry, et al., "Mixer, a Homeobox Gene Required for Endoderm Development" Science (1998) 281: 91-96.
Herrmann, B.G., Labeit, S., Poustka, A., King, T.R. & Lehrach, H. Cloning of the T gene required in mesoderm formation in the mouse. Nature 343, 617-622 (1990).
Hogan, "Bone morphogenetic proteins in development", Curr Opin Genet Dev, (1996) 6:432-438.
Holland et al. Experimental control of pancreatic development and maintenance. Proc Natl Acad Sci U S A 2002; 99(19): 12 236-12 241.
Hori, et al., "Differentiation of Insulin-Producing Cells From Human Neural Progenitor Cells" PLoS Med. (2005) 2(4): e103.
Houard, et al. "HNF-6-Independent Differentiation of Mouse Embryonic Stem Cells into Insulin-Producing Cells" Diabetologia (2003) 46: 378-385.
Houde et al., "Intestinal epithelial cell differentiation involves activation of p38 mitogen-activated protein kinase that regulates the homeobox transcription factor CDX2," J. Biol. Chem. (2005) 276(24):21885-94.
Howe, C.C., Overton, G.C., Sawicki, J., Solter, D., Stein, P., and Strickland, S. (1988). Expression of SPARC/osteonectin transcript in murine embryos and gonads. Differentiation 37, 20-25.
Hudson, C., Clements, D., Friday, R. V., Stott, D., and Woodland, H. R. (1997). Xsox17alpha and -beta mediate endoderm formation in Xenopus. Cell 91, 397-405.
Huelsken, et al., "Requirement for .beta.-Catenin in Anterior-Posterior Axis Formation in Mice" J Cell Biol (2000) 148: 567-578.
Hug, et al., "tbx6, a Brachyury-Related Gene Expressed by Ventral Mesendodermal Precursors in the Zebrafish Embryo" Development Biology, 183:61-73 (1997).
Humphrey et al. "Maintenance of Pluripotency in Human Embryonic Stem Cells Is STAT3 Independent" (2004) Stem Cells 22, 522-30.
Imada, et al. "Fetomodulin: Marker Surface Protein of Fetal Development Which Is Modulatable by Cyclic AMP" Dev Biol (1987)122: 483-491.
International Preliminary Report on Patentability from PCT/US2005/024161 dated Jan. 9, 2007.
International Search Report from PCT/US2005/024161 dated Aug. 31, 2006.
Invitation to Pay Additional Fees from PCT/US2005/024161 dated Mar. 13, 2006.
Ireland KA., Visualizing Human Biology, 3rd Ed., Wiley and Sons Inc., 2008,3 pages total.
Itskovitz-Eldor, et al., Differentiation of Human Embryonic Stem Cells into Embryoid Bodies Comprising the Three Embryonic Germ Layers, Molecular Medicine, 6, 88-95, 2000.
Jain, et al., "Glucose Control and Long-Term Survival in Breeding/Worcester Rats After Intraperitoneal Implantation of Hydrophilic Macrobeads containing Porcine Islets without Immunosuppression" Transplantation (1999) 68(11): 1693-1700.
Jaramillo, Maria et al., "Potential for Pancreatic Maturation of Differentiating Human Embryonic Stem Cells is Sensitive to the Specific Pathway of Definitive Endoderm Commitment," PLOS ONE, vol. 9, Issue 4, Apr. 2014, pp. 1-14.
Johannesson et al., "FGF4 and retionic acid direct differentiation of hESCs into PDX-1 expressing foregut endoderm in a time and concentration-dependent manner," PLoS One (2009) 4(3):e4794.
Jones et al. "Differences Between Human and Mouse Alpha-Fetoprotein Expression During Early Development" (2001) J. Anat. 198: 555-9.

METHODS OF MAKING HUMAN PRIMITIVE ECTODERM CELLS

CROSS REFERENCE TO RELATED APPLICATIONS

This is a continuation of U.S. patent application Ser. No. 15/654,624, filed Jul. 19, 2017, which is a continuation of U.S. patent application Ser. No. 13/190,390, filed on Jul. 25, 2011, now U.S. Pat. No. 9,732,318, issued on Aug. 15, 2017, which is a continuation of U.S. patent application Ser. No. 11/474,211, filed on Jun. 23, 2006, now U.S. Pat. No. 7,985,585, issued on Jul. 26, 2011, which is a continuation of PCT Application No. PCT/US2005/024161, filed Jul. 8, 2005. PCT Application No. PCT/US2005/024161 claims the benefit of U.S. Provisional Application No. 60/693,364, filed Jun. 23, 2005, U.S. Provisional Application No. 60/587,942, filed Jul. 14, 2004, and U.S. Provisional Application No. 60/586,566, filed Jul. 9, 2004. U.S. application Ser. No. 11/474,211 is also a continuation-in-part of U.S. application Ser. No. 11/021,618, filed Dec. 23, 2004, now U.S. Pat. No. 7,510,876, issued on Mar. 31, 2009, which claims the benefit of U.S. Provisional Application No. 60/587,942, filed Jul. 14, 2004, U.S. Provisional Application No. 60/586,566, filed Jul. 9, 2004, and U.S. Provisional Application No. 60/532,004, filed Dec. 23, 2003. U.S. patent application Ser. No. 11/474,211 also claims the benefit of U.S. Provisional Application No. 60/693,364, filed Jun. 23, 2005. The prior applications are incorporated herein by reference in their entirety.

FIELD

The present invention relates to the fields of medicine and cell biology. In particular, the present invention relates to compositions comprising preprimitive streak and/or mesendoderm cells as well as methods of making, isolating and using such cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases for the treatment of diabetes. However, presently it is not known how to generate an insulin-producing β-cell from hESCs. As such, current cell therapy treatments for diabetes mellitus, which utilize islet cells from donor pancreases, are limited by the scarcity of high quality islet cells needed for transplant. Cell therapy for a single Type I diabetic patient requires a transplant of approximately $8 \times 10^8$ pancreatic islet cells. (Shapiro et al., 2000; Shapiro et al., 2001a; Shapiro et al., 2001b). As such, at least two healthy donor organs are required to obtain sufficient islet cells for a successful transplant. Human embryonic stem cells offer a source of starting material from which to develop substantial quantities of high quality differentiated cells for human cell therapies.

Two properties that make hESCs uniquely suited to cell therapy applications are pluripotence and the ability to maintain these cells in culture for prolonged periods. Pluripotency is defined by the ability of hESCs to differentiate to derivatives of all 3 primary germ layers (endoderm, mesoderm, ectoderm) which, in turn, form all somatic cell types of the mature organism in addition to extraembryonic tissues (e.g. placenta) and germ cells. Although pluripotency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies. Additionally, success in evaluating production of any given cell type depends critically on defining appropriate markers. Achieving efficient, directed differentiation is of great importance for therapeutic application of hESCs.

As such, in addition to achieving efficient directed differentiation of hESCs, it would be beneficial to identify markers which can be used to identify and/or segregate cells at their earliest stages of differentiation away from hESCs. Additionally, it would be beneficial to identify factors which promote the differentiation of these early precursor cells derived from hESCs to cell types useful for cell therapies.

SUMMARY

Embodiments of the present invention relate to cell cultures comprising human cells. In such cell cultures, at least about 5% of the human cells are preprimitive streak cells, wherein the preprimitive streak cells are multipotent cells that can differentiate into mesendoderm cells. In other embodiments, at least about 10% to at least about 90% of the human cells in culture are preprimitive streak cells. In certain embodiments described herein, human feeder cells are also present in the cell cultures. In such embodiments, from at least about 5% to at least about 75% of human cells other than feeder cells are preprimitive streak cells. In some embodiments, the preprimitive streak cells express a marker, such as FGF8 and/or nuclear-localized β-catenin. In certain embodiments, the expression of one or both of these markers is greater than the expression of brachyury, FGF4, SNAI1, SOX17, FOXA2, SOX7 and/or SOX1. In still other embodiments described herein, the cell cultures are substantially free of visceral endodermal cells, parietal endodermal cells, primitive endodermal cells, definitive endodermal cells, ectodermal cells and/or mesodermal cells.

With respect to certain embodiments described herein, the preprimitive streak cell cultures comprise pluripotent human cells, such as human embryonic stem cells (hESCs). In such embodiments, from at least about 2 to at least about 10 preprimitive streak cells are present for about every 1 hESC in the cell cultures. In some embodiments the hESCs are derived from a morula, embryonic inner cell mass (ICM) or embryonic gonadal ridges. In some embodiments, the cell cultures containing human preprimitive streak cells comprise a medium comprising from less than about 2% (v/v) to from less than about 0.2% (v/v) serum. In preferred embodiments, such cell cultures comprise a medium that lacks serum or serum replacement. In other embodiments, the cell cultures containing human preprimitive streak cells comprise a growth factor of the Nodal/Activin subgroup of the TGFβ superfamily. In preferred embodiments, the growth factor is activin A.

Additional embodiments described herein relate to cell cultures comprising mesendoderm cells, wherein the mesendoderm cells are multipotent cells that can differentiate into mesoderm or definitive endoderm cells. In such embodiments, the cell cultures comprise human cells, wherein at least about 5% of the human cells are mesendoderm cells. In other embodiments, at least about 10% to at least about 90% of the human cells in culture are mesendoderm cells. In certain embodiments described herein, human feeder cells are also present in the cell cultures. In such embodiments, from at least about 5% to at least about 75% of human cells other than feeder cells are mesendoderm cells. In some embodiments, the mesendoderm cells express a marker, such as brachyury, FGF4 and/or SNAI1. In certain embodiments, the expression of one or more of these markers is greater than the expression of OCT4, SOX17, CXCR4, FOXA2, SOX7 and/or SOX1. In still other embodiments described herein, the cell cultures are substantially free of visceral endodermal cells, parietal endodermal cells, primitive endodermal cells, definitive endodermal cells, ectodermal cells and/or mesodermal cells.

With respect to certain embodiments described herein, the mesendoderm cell cultures comprise pluripotent human cells, such as human embryonic stem cells (hESCs). In such embodiments, from at least about 2 to at least about 10 mesendoderm cells are present for about every 1 hESC in the cell cultures. In some embodiments the hESCs are derived from a morula, embryonic inner cell mass (ICM) or embryonic gonadal ridges. In some embodiments, the cell cultures containing human mesendoderm cells comprise a medium comprising from less than about 2% (v/v) to from less than about 0.2% (v/v) serum. In preferred embodiments, such cell cultures comprise a medium that lacks serum or serum replacement. In other embodiments, the cell cultures containing human mesendoderm cells comprise a growth factor of the Nodal/Activin subgroup of the TGFβ superfamily. In preferred embodiments, the growth factor is activin A.

Further embodiments described herein relate to cell populations comprising cells wherein at least about 90% of the cells are human preprimitive streak cells. In these embodiments, the preprimitive streak cells are multipotent cells that can differentiate into mesendoderm cells. In other embodiments, at least about 95% to at least about 98% of the human cells in the population are preprimitive streak cells. In some embodiments, preprimitive streak cells express a marker, such as FGF8 and/or nuclear-localized β-catenin. In certain embodiments, the expression of one or both of these markers is greater than the expression of brachyury, FGF4, SNAI1, SOX17, FOXA2, SOX7 and/or SOX1. In still other embodiments described herein, the cell populations are substantially free of visceral endodermal cells, parietal endodermal cells, primitive endodermal cells, definitive endodermal cells, ectodermal cells and/or mesodermal cells.

Still other embodiments described herein relate to cell populations comprising cells wherein at least about 90% of the cells are human mesendoderm cells. In these embodiments, the mesendoderm cells are multipotent cells that can differentiate into mesoderm cells and/or definitive endoderm cells. In other embodiments, at least about 95% to at least about 98% of the human cells in the population are mesendoderm cells. In some embodiments, mesendoderm cells express a marker, such as brachyury, FGF4 and/or SNAI1. In certain embodiments, the expression of one or both of these markers is greater than the expression of OCT4, SOX17, CXCR4, FOXA2, SOX7 and/or SOX1. In still other embodiments described herein, the cell populations are substantially free of visceral endodermal cells, parietal endodermal cells, primitive endodermal cells, definitive endodermal cells, ectodermal cells and/or mesodermal cells.

Additional embodiments described herein relate to methods of producing preprimitive streak cells. In such methods, a cell population comprising pluripotent human cells, such as hESCs, is obtained. Pluripotent human cells within the cell population are differentiated in a medium comprising less than about 2% serum and at least one growth factor of the TGFβ superfamily, wherein the growth factor is present in the medium in an amount sufficient to promote differentiation of at least a portion of said pluripotent cells to preprimitive streak cells which are multipotent and can differentiate into mesendoderm cells. Some embodiments include a further step that comprises allowing sufficient time for preprimitive streak cells to form, wherein said sufficient time for preprimitive streak cells to form has been determined by detecting the presence of preprimitive streak cells in said cell population. In some embodiments, sufficient time is at least about 6 hours. In other embodiments, detecting the presence of preprimitive streak cells in the cell population comprises detecting the expression of at least one marker selected from the group consisting of FGF8 and nuclear-localized β-catenin and at least one marker from the group consisting of brachyury, FGF4, SNAI1, SOX17, FOXA2, SOX7 and SOX1 in cells of the cell population, wherein the expression of a marker selected from the group consisting of FGF8 and nuclear-localized β-catenin is greater than the expression of a marker selected from the group consisting of brachyury, FGF4, SNAI1, SOX17, FOXA2, SOX7 and SOX1 in said preprimitive streak cells. In such embodiments, marker detection can be by quantitative polymerase chain reaction (Q-PCR), immunocytochemistry or other comparable method.

With respect to certain methods described herein, from at least about 5% to at least about 90% of the human cells in culture differentiate into preprimitive streak cells. In some embodiments of the methods described herein, the growth factor present in the medium is a growth factor of the Nodal/Activin subgroup of the TGFβ superfamily. In preferred embodiments, the growth factor is activin A. In other preferred embodiments, the growth factor is present in the medium at a concentration ranging from at least about 10 ng/ml to at least about 1000 ng/ml. In certain embodiments, the growth factor is withdrawn after about 6 hours, 12 hours or 18 hours. In additional embodiments, the medium comprises from less than about 1% (v/v) to less than about 0.2% (v/v) serum. In other embodiments, the medium is low serum RPMI. In still other embodiments, the cell population is differentiated in the absence of serum or serum replacement.

Other methods described herein are methods of producing mesendoderm cells. In such methods, a cell population comprising pluripotent human cells, such as hESCs, is obtained. Pluripotent human cells within the cell population are differentiated in a medium comprising less than about 2% serum and at least one growth factor of the TGFβ superfamily, wherein the growth factor is present in the medium in an amount sufficient to promote differentiation of at least a portion of said pluripotent cells to mesendoderm cells which are multipotent and can differentiate into mesoderm cells and/or definitive endoderm cells. Some embodiments include a further step that comprises allowing sufficient time for mesendoderm cells to form, wherein said sufficient time for mesendoderm cells to form has been determined by detecting the presence of mesendoderm cells in said cell population. In some embodiments, sufficient time is at least about 24 hours. In other embodiments, detecting the presence of mesendoderm in the cell population comprises detecting the expression of at least one marker selected from the group consisting of brachyury, FGF4 and/or SNAI1 and at least one marker from the group consisting of OCT4, SOX17, CXCR4, FOXA2, SOX7 and/or SOX1 in cells of the cell population, wherein the expression of a marker selected from the group consisting of brachyury, FGF4 and/or SNAI1 is greater than the expression of a marker selected from the group consisting of OCT4, SOX17, CXCR4, FOXA2, SOX7 and/or SOX1 in said mesendoderm cells. In such embodiments, marker detection can be by quantitative polymerase chain reaction (Q-PCR), immunocytochemistry or other comparable method.

With respect to certain methods described herein, from at least about 5% to at least about 90% of the human cells in culture differentiate into mesendoderm cells. In some embodiments of the methods described herein, the growth factor present in the medium is a growth factor of the Nodal/Activin subgroup of the TGFβ superfamily. In preferred embodiments, the growth factor is activin A. In other preferred embodiments, the growth factor is present in the medium at a concentration ranging from at least about 10 ng/ml to at least about 1000 ng/ml. In certain embodiments, the growth factor is withdrawn after about 24 hours, 36 hours or 48 hours. In additional embodiments, the medium comprises from less than about 1% (v/v) to less than about 0.2% (v/v) serum. In other embodiments, the medium is low serum RPMI. In still other embodiments, the cell population is differentiated in the absence of serum or serum replacement.

Still other embodiments described herein relate to methods for producing a cell population that is enriched in preprimitive streak cells. Such methods comprise the steps of (a) obtaining a population of pluripotent cells, such as hESCs, wherein at least a one cell of the pluripotent cell population comprises a copy of a nucleic acid sequence encoding green fluorescent protein (GFP) or a biologically active fragment thereof under the control of the FGF8 promoter, (b) differentiating the pluripotent cells so as to produce preprimitive streak cells which are multipotent cells that can differentiate into mesendoderm cells, and (c) separating the preprimitive streak cells from cells that do not express GFP. In some embodiments, the cell population comprises at least about 95% to at least about 98% preprimitive streak cells. In some embodiments, the differentiating step of the methods described herein comprises providing a pluripotent cell population with at least one growth factor of the TGFβ superfamily, such as activin A. Preferred concentrations of activin A range from at least about 50 ng/ml to at least about 500 ng/ml. In additional embodiments, the cell population is differentiated in a medium comprising from less than about 1% (v/v) to less than about 0.1% (v/v) serum. In other embodiments, the medium is low serum RPMI. In still other embodiments, the cell population is differentiated in the absence of serum or serum replacement.

Other embodiments described herein relate to methods for producing a cell population that is enriched in mesendoderm cells. Such methods comprise the steps of (a) obtaining a populations of pluripotent cells, such as hESCs, wherein at least a one cell of the pluripotent cell population comprises a copy of a nucleic acid sequence encoding green fluorescent protein (GFP) or a biologically active fragment thereof under the control of the brachyury, FGF4 or SNAI1 promoter, (b) differentiating the pluripotent cells so as to produce mesendoderm cells which are multipotent cells that can differentiate into mesoderm cells and/or definitive endoderm cells, and (c) separating the mesendoderm cells from cells that do not express GFP. In some embodiments, the cell population comprises at least about 95% to at least about 98% mesendoderm cells. In some embodiments, the differentiating step of the methods described herein comprises providing a pluripotent cell population with at least one growth factor of the TGFβ superfamily, such as activin A. Preferred concentrations of activin A range from at least about 50 ng/ml to at least about 500 ng/ml. In additional embodiments, the cell population is differentiated in a medium comprising from less than about 1% (v/v) to less than about 0.1% (v/v) serum. In other embodiments, the medium is low serum RPMI. In still other embodiments, the cell population is differentiated in the absence of serum or serum replacement.

Some embodiments described herein are screening methods for identifying a differentiation factor capable of promoting the differentiation of preprimitive streak cells in a cell population comprising human cells. Such methods comprise the steps of (a) obtaining a cell population comprising human preprimitive streak cells, (b) providing a candidate differentiation factor to the cell population, (c) determining expression of a marker in the cell population at a first time point, determining expression of the same marker in the cell population at a second time point, wherein the second time point is subsequent to the first time point and wherein the second time point is subsequent to providing the population with the candidate differentiation factor, (d) and determining if expression of the marker in the cell population at the second time point is increased or decreased as compared to the expression of the marker in the cell population at the first time point, wherein an increase or decrease in expression of the marker in the cell population indicates that the candidate differentiation factor is capable of promoting the differentiation of the preprimitive streak cells. In certain embodiments, the first time point is prior to or at approximately the same time as providing the candidate differentiation factor. In other embodiments, the first time point is subsequent to providing the candidate differentiation factor. In some embodiments of the screening methods described herein, the human preprimitive streak cells differentiate into cells, such as mesendoderm cells, mesoderm cells and/or definitive endoderm cells, in response to the candidate differentiation factor. In some embodiments, mesendoderm is indicated by the expression of markers, such as brachyury, FGF4 and/or SNAI1. In other embodiments, mesoderm is indicated by the expression of markers, such as FOXF1, FLK1, BMP4, MOX1 and SDF1. In still other embodiments, definitive endoderm is indicated by the expression of markers, such as CXCR4 and/or SOX17.

With respect to the screening methods described herein, certain embodiments relate to providing a candidate differentiation factor, such as at least one growth factor from the TGFβ superfamily, such as activin A. In other embodiments, the candidate differentiation factor is a small molecule or a polypeptide. In still other embodiments, the candidate differentiation factor is not a factor of the TGFβ superfamily. In still other embodiments, the candidate differentiation factor is a factor that is not known to cause the differentiation of preprimitive streak cells.

Other embodiments described herein are screening methods for identifying a differentiation factor capable of promoting the differentiation of mesendoderm cells in a cell population comprising human cells. Such methods comprise the steps of (a) obtaining a cell population comprising human mesendoderm cells, (b) providing a candidate differentiation factor to the cell population, (c) determining expression of a marker in the cell population at a first time point, determining expression of the same marker in the cell population at a second time point, wherein the second time point is subsequent to the first time point and wherein the second time point is subsequent to providing the population with the candidate differentiation factor, (d) and determining if expression of the marker in the cell population at the second time point is increased or decreased as compared to the expression of the marker in the cell population at the first time point, wherein an increase or decrease in expression of the marker in the cell population indicates that the candidate differentiation factor is capable of promoting the differentiation of the mesendoderm cells. In certain embodiments, the first time point is prior to or at approximately the same time as providing the candidate differentiation factor. In other embodiments, the first time point is subsequent to providing the candidate differentiation factor. In some embodiments of the screening methods described herein, the human mesendoderm cells differentiate into cells, such as mesoderm cells and/or definitive endoderm cells, in response to the candidate differentiation factor. In some embodiments, mesoderm is indicated by the expression of markers, such as FOXF1, FLK1, BMP4, MOX1 and SDF1. In other embodiments, definitive endoderm is indicated by the expression of markers, such as CXCR4 and/or SOX17.

With respect to the screening methods described herein, certain embodiments relate to providing a candidate differentiation factor, such as at least one growth factor from the TGFβ superfamily, such as activin A. In other embodiments, the candidate differentiation factor is a small molecule or a polypeptide. In still other embodiments, the candidate differentiation factor is not a factor of the TGFβ superfamily. In still other embodiments, the candidate differentiation factor is a factor that is not known to cause the differentiation of mesendoderm cells.

Additional embodiments relate to a method of increasing the expression of the FGF8 gene product in a human embryonic stem cell (hESC) in vitro. The method comprises obtaining an hESC in a medium comprising less than about 2% (v/v) serum and contacting the hESC with a differentiation factor in an amount sufficient to increase expression of the FGF8 gene product. In some embodiments, the differentiation factor is at least one growth factor from the TGFβ superfamily, such as activin A. In some embodiments, the medium does not comprise serum replacement.

Still other embodiments relate to a method of increasing the expression of a gene product selected from the group consisting of brachyury, FGF4 and SNAI1 in a human embryonic stem cell (hESC) in vitro. The method comprises obtaining an hESC in a medium comprising less than about 2% (v/v) serum and contacting the hESC with a differentiation factor in an amount sufficient to increase expression of a gene product selected from the group consisting of brachyury, FGF4 and SNAI1. In some embodiments, the differentiation factor is at least one growth factor from the TGFβ superfamily, such as activin A. In some embodiments, the medium does not comprise serum replacement.

Some embodiments described herein relate to a cell culture comprising human embryonic stem cells (hESCs) and a medium comprising less than about 2% (v/v) serum, wherein the hESCs begin differentiating at a reference time point such that expression of FGF8 mRNA is substantially upregulated as compared to baseline FGF8 mRNA expression in the hESCs by about 6 hours from the reference time point. In some embodiments, the expression of β-catenin polypeptide begins to become localized to the cell nucleus by about 17 hours from the reference time point. In other embodiments, the expression of brachyury, FGF4 and/or SNAI1 mRNA is substantially upregulated by about 24 hours from the reference time point. In still other embodiments, the expression of E-cadherin mRNA begins to be downregulated by about 12 hours from the reference time point. Additionally, in some embodiments, the expression of SOX17 mRNA is substantially upregulated by about 48 hours from the reference time point and/or the expression of FOXA2 mRNA is substantially upregulated by about 96 hours from the reference time point. In certain embodiments of the cell cultures described herein, the medium comprises from less than about 1% (v/v) to less than about 0.2% (v/v) serum. In other embodiments, the medium comprises about 0% (v/v) serum. In still other embodiments, the medium does not comprise serum replacement.

Additional embodiments described herein relate to cells culture comprising human embryonic stem cells, a differentiation factor of the TGFβ superfamily and a medium comprising less than about 2% (v/v) serum, wherein a first set of marker genes is upregulated or downregulated prior to, or at about the same time as, the upregulation or peak expression of a second set and/or a third set of marker genes. In some embodiments the medium does not include serum or serum replacement.

Still other embodiments relate to methods of differentiating cells in a cell culture by contacting a cell culture comprising human embryonic stem cells with a medium comprising less that about 2% serum, providing the hESCs with a differentiation factor of the TGFβ superfamily, and permitting differentiation of the hESCs to occur. In some embodiments, such methods produce cells having a first set of marker genes that is upregulated or downregulated prior to, or at about the same time as, the upregulation or peak expression of a second set and/or a third set of marker genes. In some embodiments the medium does not include serum or serum replacement.

In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. A cell culture comprising human cells wherein at least about 5% of said human cells are preprimitive streak cells, said preprimitive streak cells being multipotent cells that can differentiate into mesendoderm cells.

2. The cell culture of paragraph 1, wherein at least about 10% of said human cells are preprimitive streak cells.

3. The cell culture of paragraph 1, wherein at least about 20% of said human cells are preprimitive streak cells.

4. The cell culture of paragraph 1, wherein at least about 30% of said human cells are preprimitive streak cells.

5. The cell culture of paragraph 1, wherein at least about 40% of said human cells are preprimitive streak cells.

6. The cell culture of paragraph 1, wherein at least about 50% of said human cells are preprimitive streak cells.

7. The cell culture of paragraph 1, wherein at least about 60% of said human cells are preprimitive streak cells.

8. The cell culture of paragraph 1, wherein at least about 70% of said human cells are preprimitive streak cells.

9. The cell culture of paragraph 1, wherein at least about 80% of said human cells are preprimitive streak cells.

10. The cell culture of paragraph 1, wherein at least about 90% of said human cells are preprimitive streak cells.

11. The cell culture of paragraph 1, wherein human feeder cells are present in said culture, and wherein at least about 5% of human cells other than said human feeder cells are preprimitive streak cells.

12. The cell culture of paragraph 1, wherein human feeder cells are present in said culture, and wherein at least about 25% of human cells other than said human feeder cells are preprimitive streak cells.

13. The cell culture of paragraph 1, wherein human feeder cells are present in said culture, and wherein at least about 50% of human cells other than said human feeder cells are preprimitive streak cells.

14. The cell culture of paragraph 1, wherein human feeder cells are present in said culture, and wherein at least about 75% of human cells other than said human feeder cells are preprimitive streak cells.

15. The cell culture of paragraph 1, wherein said primitive streak cells express a marker selected from the group consisting of FGF8 and nuclear-localized β-catenin.

16. The cell culture of paragraph 15, wherein the expression of a marker selected from the group consisting of FGF8 and nuclear-localized β-catenin is greater than the expression of a marker selected from the group consisting of brachyury, FGF4, SNAI1, SOX17, FOXA2, SOX7 and SOX1 in said preprimitive streak cells.

17. The cell culture of paragraph 15, wherein said preprimitive streak cells do not substantially express a marker selected from the group consisting of brachyury, FGF4, SNAI1, SOX17, FOXA2, SOX7 and SOX1.

18. The cell culture of paragraph 1, wherein said preprimitive streak cells express FGF8 and nuclear-localized β-catenin.

19. The cell culture of paragraph 18, wherein the expression of FGF8 and nuclear-localized β-catenin is greater than the expression of brachyury, FGF4, SNAI1, SOX17, FOXA2, SOX7 and SOX1 in said preprimitive streak cells.

20. The cell culture of paragraph 18, wherein said preprimitive streak cells do not substantially express brachyury, FGF4, SNAI1, SOX17, FOXA2, SOX7 and SOX1.

21. The cell culture of paragraph 1, wherein said cell culture is substantially free of cells selected from the group consisting of visceral endodermal cells, parietal endodermal cells, primitive endodermal cells, definitive endodermal cells, ectodermal cells and mesodermal cells.

22. The cell culture of paragraph 1 further comprising human embryonic stem cells (hESCs).

23. The cell culture of paragraph 22, wherein at least about 2 preprimitive streak cells are present for about every 1 hESC in said cell culture.

24. The cell culture of paragraph 22, wherein at least about 10 preprimitive streak cells are present for about every 1 hESC in said cell culture.

25. The cell culture of paragraph 22, wherein said hESC is derived from a tissue selected from the group consisting of the morula, the inner cell mass (ICM) of an embryo and the gonadal ridges of an embryo.

26. The cell culture of paragraph 1 further comprising a medium that comprises less than about 2% (v/v) serum.

27. The cell culture of paragraph 1 further comprising a medium that comprises less than about 1% (v/v) serum.

28. The cell culture of paragraph 1 further comprising a medium that comprises less than about 0.5% (v/v) serum.

29. The cell culture of paragraph 1 further comprising a medium that comprises less than about 0.2% (v/v) serum.

30. The cell culture of paragraph 1 further comprising a medium that lacks serum or lacks serum replacement.

31. The cell culture of paragraph 1 further comprising a growth factor of the Nodal/Activin subgroup of the TGFβ superfamily 32. The cell culture of paragraph 31, wherein said growth factor of the Nodal/Activin subgroup of the TGFβ superfamily comprises activin A.

33. A cell culture comprising human cells wherein at least about 5% of said human cells are mesendoderm cells, said mesendoderm cells being multipotent cells that can differentiate into mesoderm cells or definitive endoderm cells.

34. The cell culture of paragraph 33, wherein at least about 10% of said human cells are mesendoderm cells.

35. The cell culture of paragraph 33, wherein at least about 20% of said human cells are mesendoderm cells.

36. The cell culture of paragraph 33, wherein at least about 30% of said human cells are mesendoderm cells.

37. The cell culture of paragraph 33, wherein at least about 40% of said human cells are preprimitive streak cells.

38. The cell culture of paragraph 33, wherein at least about 50% of said human cells are mesendoderm cells.

39. The cell culture of paragraph 33, wherein at least about 60% of said human cells are mesendoderm cells.

40. The cell culture of paragraph 33, wherein at least about 70% of said human cells are mesendoderm cells.

41. The cell culture of paragraph 33, wherein at least about 80% of said human cells are mesendoderm cells.

42. The cell culture of paragraph 33, wherein at least about 90% of said human cells are mesendoderm cells.

43. The cell culture of paragraph 33, wherein human feeder cells are present in said culture, and wherein at least about 5% of human cells other than said human feeder cells are mesendoderm cells.

44. The cell culture of paragraph 33, wherein human feeder cells are present in said culture, and wherein at least about 25% of human cells other than said human feeder cells are mesendoderm cells.

45. The cell culture of paragraph 33, wherein human feeder cells are present in said culture, and wherein at least about 50% of human cells other than said human feeder cells are mesendoderm cells.

46. The cell culture of paragraph 33, wherein human feeder cells are present in said culture, and wherein at least about 75% of human cells other than said human feeder cells are mesendoderm cells.

47. The cell culture of paragraph 33, wherein said mesendoderm cells express a marker selected from the group consisting of brachyury, FGF4 and SNAI1.

48. The cell culture of paragraph 47, wherein the expression of a marker selected from the group consisting of brachyury, FGF4 and SNAI1 is greater than the expression of a marker selected from the group consisting of OCT4, SOX17, CXCR4, FOXA2, SOX7 and SOX1 in said mesendoderm cells.

49. The cell culture of paragraph 47, wherein said mesendoderm cells do not substantially express a marker selected from the group consisting of OCT4, SOX17, CXCR4, FOXA2, SOX7 and SOX1.

50. The cell culture of paragraph 33, wherein said mesendoderm cells express brachyury, FGF4 and SNAI1.

51. The cell culture of paragraph 50, wherein the expression of brachyury, FGF4 and SNAI1 is greater than the expression of OCT4, SOX17, CXCR4, FOXA2, SOX7 and SOX1 in said mesendoderm cells.

52. The cell culture of paragraph 51, wherein said mesendoderm cells do not substantially express OCT4, SOX17, CXCR4, FOXA2, SOX7 and SOX1.

53. The cell culture of paragraph 33, wherein said cell culture is substantially free of cells selected from the group consisting of visceral endodermal cells, parietal endodermal cells, primitive endodermal cells, definitive endodermal cells, ectodermal cells and mesodermal cells.

54. The cell culture of paragraph 33 further comprising human embryonic stem cells (hESCs).

55. The cell culture of paragraph 54, wherein at least about 2 mesendoderm cells are present for about every 1 hESC in said cell culture.

56. The cell culture of paragraph 54, wherein at least about 10 mesendoderm cells are present for about every 1 hESC in said cell culture.

57. The cell culture of paragraph 54, wherein said hESC is derived from a tissue selected from the group consisting of the morula, the inner cell mass (ICM) of an embryo and the gonadal ridges of an embryo.

58. The cell culture of paragraph 33 further comprising a medium that comprises less than about 2% (v/v) serum.

59. The cell culture of paragraph 33 further comprising a medium that comprises less than about 1% (v/v) serum.

60. The cell culture of paragraph 33 further comprising a medium that comprises less than about 0.5% (v/v) serum.

61. The cell culture of paragraph 33 further comprising a medium that comprises less than about 0.2% (v/v) serum.

62. The cell culture of paragraph 33 further comprising a medium that lacks serum or lacks serum replacement.

63. The cell culture of paragraph 33 further comprising a growth factor of the Nodal/Activin subgroup of the TGFβ superfamily 64. The cell culture of paragraph 63, wherein said growth factor of the Nodal/Activin subgroup of the TGFβ superfamily comprises activin A.

65. A cell population comprising cells wherein at least about 90% of said cells are human preprimitive streak cells, said preprimitive streak cells being multipotent cells that can differentiate into mesendoderm cells.

66. The cell population of paragraph 65, wherein at least about 95% of said cells are human preprimitive streak cells.

67. The cell population of paragraph 65, wherein at least about 98% of said cells are human preprimitive streak cells.

68. The cell population of paragraph 65, wherein said human preprimitive streak cells express a marker selected from the group consisting of FGF8 and nuclear-localized β-catenin.

69. The cell population of paragraph 68, wherein the expression of a marker selected from the group consisting of FGF8 and nuclear-localized β-catenin is greater than the expression of a marker selected from the group consisting of brachyury, FGF4, SNAI1, SOX17, FOXA2, SOX7 and SOX1 in said human preprimitive streak cells.

70. The cell population of paragraph 68, wherein said human preprimitive streak cells do not substantially express a marker selected from the group consisting of brachyury, FGF4, SNAI1, SOX17, FOXA2, SOX7 and SOX1.

71. The cell population of paragraph 65, wherein said human preprimitive streak cells express FGF8 and nuclear-localized β-catenin.

72. The cell population of paragraph 71, wherein the expression of FGF8 and β-catenin is greater than the expression of brachyury, FGF4, SNAI1, SOX17, FOXA2, SOX7 and SOX1 in said human preprimitive streak cells.

73. The cell population of paragraph 71, wherein said human preprimitive streak cells do not substantially express brachyury, FGF4, SNAI1, SOX17, FOXA2, SOX7 and SOX1.

74. A cell population comprising cells wherein at least about 90% of said cells are human mesendoderm cells, said mesendoderm cells being multipotent cells that can differentiate into mesoderm cells or definitive endoderm cells.

75. The cell population of paragraph 74, wherein at least about 95% of said cells are human mesendoderm cells.

76. The cell population of paragraph 74, wherein at least about 98% of said cells are human mesendoderm cells.

77. The cell population of paragraph 74, wherein said human mesendoderm cells express a marker selected from the group consisting of brachyury, FGF4 and SNAI1.

78. The cell population of paragraph 77, wherein the expression of a marker selected from the group consisting of brachyury, FGF4 and SNAI1 is greater than the expression of a marker selected from the group consisting of OCT4, SOX17, CXCR4, FOXA2, SOX7 and SOX1 in said human mesendoderm cells.

79. The cell population of paragraph 77, wherein said human mesendoderm cells do not substantially express a marker selected from the group consisting of OCT4, SOX17, CXCR4, FOXA2, SOX7 and SOX1.

80. The cell population of paragraph 74, wherein said human mesendoderm cells express brachyury, FGF4 and SNAI1.

81. The cell population of paragraph 80, wherein the expression of brachyury, FGF4 and SNAI1 is greater than the expression of OCT4, SOX17, CXCR4, FOXA2, SOX7 and SOX1 in said human mesendoderm cells.

82. The cell population of paragraph 80, wherein said human mesendoderm cells do not substantially express OCT4, SOX17, CXCR4, FOXA2, SOX7 and SOX1.

83. A method of producing preprimitive streak cells, said method comprising the steps of obtaining a cell population comprising pluripotent human cells and differentiating said pluripotent human cells in a medium comprising less than about 2% serum and at least one growth factor of the TGFβ superfamily, wherein said growth factor is present in the medium in an amount sufficient to promote differentiation of at least a portion of said pluripotent cells to preprimitive streak cells, said preprimitive streak cells being multipotent cells that can differentiate into mesendoderm cells.

84. The method of paragraph 83 further comprising the step of allowing sufficient time for preprimitive streak cells to form, wherein said sufficient time for preprimitive streak cells to form has been determined by detecting the presence of preprimitive streak cells in said cell population.

85. The method of paragraph 84, wherein sufficient time is at least about 6 hours.

86. The method of paragraph 84, wherein detecting the presence of preprimitive streak cells in said cell population comprises detecting the expression of at least one marker selected from the group consisting of FGF8 and nuclear-localized β-catenin and at least one marker from the group consisting of brachyury, FGF4, SNAI1, SOX17, FOXA2, SOX7 and SOX1 in cells of said cell population, wherein the expression of a marker selected from the group consisting of FGF8 and nuclear-localized β-catenin is greater than the expression of a marker selected from the group consisting of brachyury, FGF4, SNAI1, SOX17, FOXA2, SOX7 and SOX1 in said preprimitive streak cells.

87. The method of paragraph 86, wherein the expression of at least one of said markers is determined by quantitative polymerase chain reaction (Q-PCR).

88. The method of paragraph 86, wherein the expression of at least one of said markers is determined by immunocytochemistry.

89. The method of paragraph 83, wherein at least about 5% of said pluripotent human cells differentiate into preprimitive streak cells.

90. The method of paragraph 83, wherein at least about 10% of said pluripotent human cells differentiate into preprimitive streak cells.

91. The method of paragraph 83, wherein at least about 20% of said pluripotent human cells differentiate into preprimitive streak cells.

92. The method of paragraph 83, wherein at least about 30% of said pluripotent human cells differentiate into preprimitive streak cells.

93. The method of paragraph 83, wherein at least about 40% of said pluripotent human cells differentiate into preprimitive streak cells.

94. The method of paragraph 83, wherein at least about 50% of said pluripotent human cells differentiate into preprimitive streak cells.

95. The method of paragraph 83, wherein at least about 60% of said pluripotent human cells differentiate into preprimitive streak cells.

96. The method of paragraph 83, wherein at least about 70% of said pluripotent human cells differentiate into preprimitive streak cells.

97. The method of paragraph 83, wherein at least about 80% of said pluripotent human cells differentiate into preprimitive streak cells.

98. The method of paragraph 83, wherein at least about 90% of said pluripotent human cells differentiate into preprimitive streak cells.

99. The method of paragraph 83, wherein said at least one growth factor is of the Nodal/Activin subgroup of the TGFβ superfamily 100. The method of paragraph 99, wherein said at least one growth factor of the Nodal/Activin subgroup of the TGFβ superfamily comprises activin A.

101. The method of paragraph 83, wherein said at least one growth factor is provided in a concentration of at least about 10 ng/ml.

102. The method of paragraph 83, wherein said at least one growth factor is provided in a concentration of at least about 100 ng/ml.

103. The method of paragraph 83, wherein said at least one growth factor is provided in a concentration of at least about 500 ng/ml.

104. The method of paragraph 83, wherein said at least one growth factor is provided in a concentration of at least about 1000 ng/ml.

105. The method of paragraph 83, wherein said at least one growth factor is withdrawn after about 6 hours.

106. The method of paragraph 83, wherein said at least one growth factor is withdrawn after about 12 hours.

107. The method of paragraph 83, wherein said at least one growth factor is withdrawn after about 18 hours.

108. The method of paragraph 83, wherein said cell population is differentiated in a medium comprising less than about 1% (v/v) serum.

109. The method of paragraph 83, wherein said cell population is differentiated in a medium comprising less than about 0.5% (v/v) serum.

110. The method of paragraph 83, wherein said cell population is differentiated in a medium comprising less than about 0.2% (v/v) serum.

111. The method of paragraph 83, wherein said cell population is differentiated in a medium comprising less than about 0.1% (v/v) serum.

112. The method of paragraph 83, wherein said cell population is differentiated in the absence of serum or the absence of serum replacement.

113. The method of paragraph 83, wherein said cell population is differentiated in a medium comprising about 0% (v/v) serum on about the first day after adding said at least one growth factor, about 0.2% (v/v) serum or less on about the second day after adding said at least one growth factor and about 2% (v/v) serum or less on about the third day after adding said at least one growth factor.

114. The method of paragraph 83, wherein said cell population is differentiated in low serum RPMI medium.

115. The method of paragraph 83, wherein said pluripotent human cells comprise human embryonic stem cells (hESCs).

116. The method of paragraph 115, wherein said human embryonic stem cells are derived from a tissue selected from the group consisting of the morula, the inner cell mass (ICM) of an embryo and the gonadal ridges of an embryo.

117. A preprimitive streak cell produced by the method of paragraph 83.

118. A method of producing mesendoderm cells, said method comprising the steps of obtaining a cell population comprising pluripotent human cells and differentiating said pluripotent human cells in a medium comprising less than about 2% serum and at least one growth factor of the TGFβ superfamily, wherein said growth factor is present in the medium in an amount sufficient to promote differentiation of at least a portion of said pluripotent cells to mesendoderm cells, said mesendoderm cells being multipotent cells that can differentiate into mesendoderm cells.

119. The method of paragraph 118 further comprising the step of allowing sufficient time for mesendoderm cells to form, wherein said sufficient time for mesendoderm cells to form has been determined by detecting the presence of mesendoderm cells in said cell population.

120. The method of paragraph 119, wherein sufficient time is at least about 24 hours.

121. The method of paragraph 118, wherein detecting the presence of mesendoderm cells in said cell population comprises detecting the expression of at least one marker selected from the group consisting of brachyury, FGF4 and SNAI1 and at least one marker from the group consisting of OCT4, SOX17, CXCR4, FOXA2, SOX7 and SOX1 in cells of said cell population, wherein the expression of a marker selected from the group consisting of brachyury, FGF4 and SNAI1 is greater than the expression of a marker selected from the group consisting of OCT4, SOX17, CXCR4, FOXA2, SOX7 and SOX1 in said mesendoderm cells.

122. The method of paragraph 121, wherein the expression of at least one of said markers is determined by quantitative polymerase chain reaction (Q-PCR).

123. The method of paragraph 121, wherein the expression of at least one of said markers is determined by immunocytochemistry.

124. The method of paragraph 118, wherein at least about 5% of said pluripotent human cells differentiate into mesendoderm cells.

125. The method of paragraph 118, wherein at least about 10% of said pluripotent human cells differentiate into mesendoderm cells.

126. The method of paragraph 118, wherein at least about 20% of said pluripotent human cells differentiate into mesendoderm cells.

127. The method of paragraph 118, wherein at least about 30% of said pluripotent human cells differentiate into mesendoderm cells.

128. The method of paragraph 118, wherein at least about 40% of said pluripotent human cells differentiate into mesendoderm cells.

129. The method of paragraph 118, wherein at least about 50% of said pluripotent human cells differentiate into mesendoderm cells.

130. The method of paragraph 118, wherein at least about 60% of said pluripotent human cells differentiate into mesendoderm cells.

131. The method of paragraph 118, wherein at least about 70% of said pluripotent human cells differentiate into mesendoderm cells.

132. The method of paragraph 118, wherein at least about 80% of said pluripotent human cells differentiate into mesendoderm cells.

133. The method of paragraph 118, wherein at least about 90% of said pluripotent human cells differentiate into mesendoderm cells.

134. The method of paragraph 118, wherein said at least one growth factor is of the Nodal/Activin subgroup of the TGFβ superfamily 135. The method of paragraph 134, wherein said at least one growth factor of the Nodal/Activin subgroup of the TGFβ superfamily comprises activin A.

136. The method of paragraph 118, wherein said at least one growth factor is provided in a concentration of at least about 10 ng/ml.

137. The method of paragraph 118, wherein said at least one growth factor is provided in a concentration of at least about 100 ng/ml.

138. The method of paragraph 118, wherein said at least one growth factor is provided in a concentration of at least about 500 ng/ml.

139. The method of paragraph 118, wherein said at least one growth factor is provided in a concentration of at least about 1000 ng/ml.

140. The method of paragraph 118, wherein said at least one growth factor is withdrawn after about 24 hours.

141. The method of paragraph 118, wherein said at least one growth factor is withdrawn after about 36 hours.

142. The method of paragraph 118, wherein said at least one growth factor is withdrawn after about 48 hours.

143. The method of paragraph 118, wherein said cell population is differentiated in a medium comprising less than about 1% (v/v) serum.

144. The method of paragraph 118, wherein said cell population is differentiated in a medium comprising less than about 0.5% (v/v) serum.

145. The method of paragraph 118, wherein said cell population is differentiated in a medium comprising less than about 0.2% (v/v) serum.

146. The method of paragraph 118, wherein said cell population is differentiated in a medium comprising less than about 0.1% (v/v) serum.

147. The method of paragraph 118, wherein said cell population is differentiated in the absence of serum or the absence of serum replacement.

148. The method of paragraph 118, wherein said cell population is differentiated in a medium comprising about 0% (v/v) serum on about the first day after adding said at least one growth factor, about 0.2% (v/v) serum or less on about the second day after adding said at least one growth factor and about 2% (v/v) serum or less on about the third day after adding said at least one growth factor.

149. The method of paragraph 118, wherein said cell population is differentiated in low serum RPMI medium.

150. The method of paragraph 118, wherein said pluripotent human cells comprise human embryonic stem cells (hESCs).

151. The method of paragraph 150, wherein said human embryonic stem cells are derived from a tissue selected from the group consisting of the morula, the inner cell mass (ICM) of an embryo and the gonadal ridges of an embryo.

152. A mesendoderm cell produced by the method of paragraph 118.

153. A method of producing a cell population enriched in preprimitive streak cells, said method comprising the steps of obtaining a population of pluripotent cells, wherein at least one cell of said pluripotent cell population comprises at least one copy of a nucleic acid under the control of the FGF8 promoter, said nucleic acid comprising a sequence encoding green fluorescent protein (GFP) or a biologically active fragment thereof; differentiating said pluripotent cells so as to produce preprimitive streak cells, said preprimitive streak cells being multipotent cells that can differentiate into mesendoderm cells, and separating said preprimitive streak cells from cells which do not express GFP.

154. The method of paragraph 153, wherein said enriched cell population comprises at least about 95% preprimitive streak cells.

155. The method of paragraph 153, wherein said enriched cell population comprises at least about 98% preprimitive streak cells.

156. The method of paragraph 153, wherein the differentiating step comprises providing said pluripotent cell population with at least one growth factor from the TGFβ superfamily in an amount sufficient to promote differentiation of said pluripotent cells to preprimitive streak cells.

157. The method of paragraph 156, wherein said at least one growth factor of the TGFβ superfamily is activin A.

158. The method of paragraph 157, wherein said activin A is provided in a concentration of at least about 50 ng/ml.

159. The method of paragraph 157, wherein said activin A is provided in a concentration of at least about 100 ng/ml.

160. The method of paragraph 157, wherein said activin A is provided in a concentration of at least about 500 ng/ml.

161. The method of paragraph 153, wherein said cell population is differentiated in a medium comprising less than about 1% (v/v) serum.

162. The method of paragraph 153, wherein said cell population is differentiated in a medium comprising less than about 0.5% (v/v) serum.

163. The method of paragraph 153, wherein said cell population is differentiated in a medium comprising less than about 0.2% (v/v) serum.

164. The method of paragraph 153, wherein said cell population is differentiated in a medium comprising less than about 0.1% (v/v) serum.

165. The method of paragraph 153, wherein said cell population is differentiated in the absence of serum or the absence of serum replacement.

166. The method of paragraph 153, wherein said cell population is differentiated in a medium comprising about 0% (v/v) serum on about the first day after adding said at least one growth factor, about 0.2% (v/v) serum or less on about the second day after adding said at least one growth factor and about 2% (v/v) serum or less on about the third day after adding said at least one growth factor.

167. The method of paragraph 153, wherein said cell population is differentiated in low serum RPMI medium.

168. An enriched population of preprimitive streak cells produced by the method of paragraph 153.

169. A method of producing a cell population enriched in mesendoderm cells, said method comprising the steps of obtaining a population of pluripotent cells, wherein at least one cell of said pluripotent cell population comprises at least one copy of a nucleic acid under the control of a promoter selected from the group consisting of the brachyury promoter, the FGF4 promoter and the SNAI1 promoter, said nucleic acid comprising a sequence encoding green fluorescent protein (GFP) or a biologically active fragment thereof; differentiating said pluripotent cells so as to produce mesendoderm cells, said mesendoderm cells being multipotent cells that can differentiate into mesoderm cells or definitive endoderm cells, and separating said mesendoderm cells from cells which do not express GFP.

170. The method of paragraph 169, wherein said enriched cell population comprises at least about 95% mesendoderm cells.

171. The method of paragraph 169, wherein said enriched cell population comprises at least about 98% mesendoderm cells.

172. The method of paragraph 169, wherein the differentiating step comprises providing said pluripotent cell population with at least one growth factor of the TGFβ superfamily in an amount sufficient to promote differentiation of said pluripotent cells to mesendoderm cells.

173. The method of paragraph 172, wherein said at least one growth factor of the TGFβ superfamily is activin A.

174. The method of paragraph 173, wherein said activin A is provided in a concentration of at least about 50 ng/ml.

175. The method of paragraph 173, wherein said activin A is provided in a concentration of at least about 100 ng/ml.

176. The method of paragraph 173, wherein said activin A is provided in a concentration of at least about 500 ng/ml.

177. The method of paragraph 169, wherein said cell population is differentiated in a medium comprising less than about 1% (v/v) serum.

178. The method of paragraph 169, wherein said cell population is differentiated in a medium comprising less than about 0.5% (v/v) serum.

179. The method of paragraph 169, wherein said cell population is differentiated in a medium comprising less than about 0.2% (v/v) serum.

180. The method of paragraph 169, wherein said cell population is differentiated in a medium comprising less than about 0.1% (v/v) serum.

181. The method of paragraph 169, wherein said cell population is differentiated in the absence of serum or the absence of serum replacement.

182. The method of paragraph 169, wherein said cell population is differentiated in a medium comprising about 0% (v/v) serum on about the first day after adding said at least one growth factor, about 0.2% (v/v) serum or less on about the second day after adding said at least one growth factor and about 2% (v/v) serum or less on about the third day after adding said at least one growth factor.

183. The method of paragraph 169, wherein said cell population is differentiated in low serum RPMI medium.

184. An enriched population of mesendoderm cells produced by the method of paragraph 169.

185. A method of identifying a differentiation factor capable of promoting the differentiation of preprimitive streak cells in a cell population comprising human cells, said method comprising the steps of obtaining a cell population comprising human preprimitive streak cells, providing a candidate differentiation factor to said cell population, determining expression of a marker in said cell population at a first time point, determining expression of the same marker in said cell population at a second time point, wherein said second time point is subsequent to said first time point and wherein said second time point is subsequent to providing said population with said candidate differentiation factor, and determining if expression of the marker in said cell population at said second time point is increased or decreased as compared to the expression of the marker in said cell population at said first time point, wherein an increase or decrease in expression of said marker in said cell population indicates that said candidate differentiation factor is capable of promoting the differentiation of said preprimitive streak cells.

186. The method of paragraph 185, wherein said human preprimitive streak cells comprise at least about 10% of the human cells in said cell population.

187. The method of paragraph 185, wherein human feeder cells are present in said cell population and wherein at least about 10% of the human cells other than said feeder cells are preprimitive streak cells.

188. The method of paragraph 185, wherein said human preprimitive streak cells comprise at least about 50% of the human cells in said cell population.

189. The method of paragraph 185, wherein said human feeder cells are present in said cell population and wherein at least about 50% of the human cells other than said feeder cells are preprimitive streak cells.

190. The method of paragraph 185, wherein said human preprimitive streak cells differentiate into cells selected from the group consisting of mesendoderm, mesoderm and definitive endoderm in response to said candidate differentiation factor.

191. The method of paragraph 185, wherein said human preprimitive streak cells differentiate into mesendoderm cells in response to said candidate differentiation factor.

192. The method of paragraph 191, wherein said marker is selected from the group consisting of brachyury, FGF4 and SNAI1.

193. The method of paragraph 185, wherein said human preprimitive streak cells differentiate into mesoderm cells in response to said candidate differentiation factor.

194. The method of paragraph 193, wherein said marker is selected from the group consisting of FOXF1, FLK1, BMP4, MOX1 and SDF1.

195. The method of paragraph 185, wherein said human preprimitive streak cells differentiate into definitive endoderm cells in response to said candidate differentiation factor.

196. The method of paragraph 195, wherein said marker is selected from the group consisting of CXCR4 and SOX17.

197. The method of paragraph 185, wherein said first time point is prior to providing said candidate differentiation factor to said cell population.

198. The method of paragraph 185, wherein said first time point is at approximately the same time as providing said candidate differentiation factor to said cell population.

199. The method of paragraph 185, wherein said first time point is subsequent to providing said candidate differentiation factor to said cell population.

200. The method of paragraph 185, wherein expression of said marker is increased.

201. The method of paragraph 185, wherein expression of said marker is decreased.

202. The method of paragraph 185, wherein expression of said marker is determined by quantitative polymerase chain reaction (Q-PCR).

203. The method of paragraph 185, wherein expression of said marker is determined by immunocytochemistry.

204. The method of paragraph 185, wherein said candidate differentiation factor comprises at least one growth factor of the TGFβ superfamily.

205. The method of paragraph 204, wherein said at least one growth factor of the TGFβ superfamily is activin A.

206. The method of paragraph 185, wherein said candidate differentiation factor comprises a small molecule.

207. The method of paragraph 185, wherein said candidate differentiation factor comprises a polypeptide.

208. The method of paragraph 185, wherein said candidate differentiation factor is not a growth factor of the TGFβ superfamily 209. The method of paragraph 185, wherein said candidate differentiation factor is provided to said cell population at a concentration of between about 0.1 ng/ml to about 10 mg/ml.

210. The method of paragraph 185, wherein said candidate differentiation factor is provided to said cell population at a concentration of between about 1 ng/ml to about 1 mg/ml 211. The method of paragraph 185, wherein said candidate differentiation factor is provided to said cell population at a concentration of between about 10 ng/ml to about 100 μg/ml.

212. The method of paragraph 185, wherein said candidate differentiation factor is provided to said cell population at a concentration of between about 100 ng/ml to about 10 μg/ml.

213. The method of paragraph 185, wherein said candidate differentiation factor is provided to said cell population at a concentration of about 1 μg/ml.

214. A method of identifying a differentiation factor capable of promoting the differentiation of mesendoderm cells in a cell population comprising human cells, said method comprising the steps of obtaining a cell population comprising human mesendoderm cells, providing a candidate differentiation factor to said cell population, determining expression of a marker in said cell population at a first time point, determining expression of the same marker in said cell population at a second time point, wherein said second time point is subsequent to said first time point and wherein said second time point is subsequent to providing said population with said candidate differentiation factor, and determining if expression of the marker in said cell population at said second time point is increased or decreased as compared to the expression of the marker in said cell population at said first time point, wherein an increase or decrease in expression of said marker in said cell population indicates that said candidate differentiation factor is capable of promoting the differentiation of said mesendoderm cells.

215. The method of paragraph 214, wherein said human mesendoderm cells comprise at least about 10% of the human cells in said cell population.

216. The method of paragraph 214, wherein human feeder cells are present in said cell population and wherein at least about 10% of the human cells other than said feeder cells are mesendoderm cells.

217. The method of paragraph 214, wherein said human mesendoderm cells comprise at least about 50% of the human cells in said cell population.

218. The method of paragraph 214, wherein said human feeder cells are present in said cell population and wherein at least about 50% of the human cells other than said feeder cells are mesendoderm cells.

219. The method of paragraph 214, wherein said human mesendoderm cells differentiate into cells selected from the group consisting of mesoderm and definitive endoderm in response to said candidate differentiation factor.

220. The method of paragraph 214, wherein said human mesendoderm cells differentiate into mesoderm cells in response to said candidate differentiation factor.

221. The method of paragraph 220, wherein said marker is selected from the group consisting of FOXF1, FLK1, BMP4, MOX1 and SDF1.

222. The method of paragraph 214, wherein said human mesendoderm cells differentiate into definitive endoderm cells in response to said candidate differentiation factor.

223. The method of paragraph 222, wherein said marker is selected from the group consisting of CXCR4 and SOX17.

224. The method of paragraph 214, wherein said first time point is prior to providing said candidate differentiation factor to said cell population.

225. The method of paragraph 214, wherein said first time point is at approximately the same time as providing said candidate differentiation factor to said cell population.

226. The method of paragraph 214, wherein said first time point is subsequent to providing said candidate differentiation factor to said cell population.

227. The method of paragraph 214, wherein expression of said marker is increased.

228. The method of paragraph 214, wherein expression of said marker is decreased.

229. The method of paragraph 214, wherein expression of said marker is determined by quantitative polymerase chain reaction (Q-PCR).

230. The method of paragraph 214, wherein expression of said marker is determined by immunocytochemistry.

231. The method of paragraph 214, wherein said candidate differentiation factor comprises at least one growth factor of the TGFβ superfamily.

232. The method of paragraph 231, wherein said at least one growth factor of the TGFβ superfamily is activin A.

233. The method of paragraph 214, wherein said candidate differentiation factor comprises a small molecule.

234. The method of paragraph 214, wherein said candidate differentiation factor comprises a polypeptide.

235. The method of paragraph 214, wherein said candidate differentiation factor is not a growth factor of the TGFβ superfamily.

236. The method of paragraph 214, wherein said candidate differentiation factor is provided to said cell population at a concentration of between about 0.1 ng/ml to about 10 mg/ml.

237. The method of paragraph 214, wherein said candidate differentiation factor is provided to said cell population at a concentration of between about 1 ng/ml to about 1 mg/ml 238. The method of paragraph 214, wherein said candidate differentiation factor is provided to said cell population at a concentration of between about 10 ng/ml to about 100 μg/ml.

239. The method of paragraph 214, wherein said candidate differentiation factor is provided to said cell population at a concentration of between about 100 ng/ml to about 10 μg/ml.

240. The method of paragraph 214, wherein said candidate differentiation factor is provided to said cell population at a concentration of about 1 μg/ml.

241. A method of increasing the expression of the FGF8 gene product in a human embryonic stem cell (hESC) in vitro, said method comprising obtaining said hESC in a medium comprising less than about 2% (v/v) serum and contacting said hESC with a differentiation factor in an amount sufficient to increase expression of the FGF8 gene product.

242. The method of paragraph 241, wherein said differentiation factor comprises at least one growth factor of the TGFβ superfamily.

243. The method of paragraph 242, wherein said differentiation factor comprises activin A.

244. The method of paragraph 241, wherein said medium lacks serum or lacks serum replacement.

245. A method of increasing the expression of a gene product selected from the group consisting of brachyury, FGF4 and SNAI1 in an human embryonic stem cell (hESC) or a preprimitive streak cell in vitro, said method comprising obtaining said hESC or preprimitive streak cell in a medium comprising less than about 2% (v/v) serum and contacting said hESC or said preprimitive streak cell with a differentiation factor in an amount sufficient to increase expression of a gene product selected from the group consisting of brachyury, FGF4 and SNAI1.

246. The method of paragraph 245, wherein said differentiation factor comprises at least one growth factor of the TGFβ superfamily.

247. The method of paragraph 246, wherein said differentiation factor comprises activin A.

248. The method of paragraph 245, wherein said medium lacks serum or lacks serum replacement.

249. A cell culture comprising human embryonic stem cells (hESCs) and a medium comprising less than about 2% (v/v) serum, wherein said hESCs begin differentiating at a reference time point such that expression of FGF8 mRNA is substantially upregulated as compared to baseline FGF8 mRNA expression in said hESCs by about 6 hours from said reference time point.

250. The cell culture of paragraph 249, wherein expression of FGF8 mRNA is downregulated after about 24 hours from said reference time point.

251. The cell culture of paragraph 250, wherein peak expression of FGF8 mRNA is reached at a time between about 6 hours and about 24 hours from said reference time point.

252. The cell culture of paragraph 249, wherein β-catenin polypeptide begins to become localized to the cell nucleus by about 17 hours from said reference time point.

253. The cell culture of paragraph 249, wherein expression of brachyury mRNA is substantially upregulated by about 24 hours from said reference time point.

254. The cell culture of paragraph 253, wherein expression of brachyury mRNA is substantially downregulated by about 48 hours from said reference time point.

255. The cell culture of paragraph 254, wherein peak expression of brachyury mRNA is reached at a time between about 12 hours and about 48 hours from said reference time point.

256. The cell culture of paragraph 255, wherein brachyury mRNA in not substantially expressed by about 72 hours from said reference time point.

257. The cell culture of paragraph 249, wherein expression of FGF4 mRNA is substantially upregulated by about 24 hours from said reference time point.

258. The cell culture of paragraph 257, wherein expression of FGF4 mRNA is substantially downregulated by about 48 hours from said reference time point.

259. The cell culture of paragraph 258, wherein peak expression of FGF4 mRNA is reached at a time between about 12 hours and about 48 hours from said reference time point.

260. The cell culture of paragraph 259, wherein FGF4 mRNA is not substantially expressed by about 72 hours from said reference time point.

261. The cell culture of paragraph 249, wherein expression of brachyury and FGF4 mRNA is substantially upregulated by about 24 hours from said reference time point.

262. The cell culture of paragraph 261, wherein expression of brachyury and FGF4 mRNA is substantially downregulated by about 48 hours from said reference time point.

263. The cell culture of paragraph 262, wherein peak expression of brachyury and FGF4 mRNA is reached at a time between about 12 hours and about 48 hours from said reference time point.

264. The cell culture of paragraph 263, wherein brachyury and FGF4 mRNA in not substantially expressed by about 72 hours from said reference time point.

265. The cell culture of paragraph 249, wherein expression of SNAI1 mRNA is substantially upregulated by about 24 hours from said reference time point.

266. The cell culture of paragraph 265, wherein expression of SNAI1 mRNA is downregulated by about 48 hours from said reference time point.

267. The cell culture of paragraph 266, wherein peak expression of SNAI1 mRNA is reached at a time between about 12 hours and about 48 hours from said reference time point.

268. The cell culture of paragraph 249, wherein expression of E-cadherin mRNA begins to be downregulated by about 12 hours from said reference time point.

269. The cell culture of paragraph 249, wherein expression of E-cadherin mRNA is substantially downregulated by about 48 hours from said reference time point.

270. The cell culture of paragraph 249, wherein expression of SOX17 mRNA is substantially upregulated by about 48 hours from said reference time point.

271. The cell culture of paragraph 249, wherein expression of FOXA2 mRNA is substantially upregulated by about 96 hours from said reference time point.

272. The cell culture of paragraph 249, wherein said medium comprises less than about 1% (v/v) serum.

273. The cell culture of paragraph 249, wherein said medium comprises less than about 0.2% (v/v) serum.

274. The cell culture of paragraph 249, wherein said medium comprises about 0% (v/v) serum.

275. The cell culture of paragraph 249, wherein said medium lacks serum or lacks serum replacement.

276. The cell culture of paragraph 249, further comprising a differentiation factor of the TGFβ superfamily 277. The cell culture of paragraph 276, wherein said differentiation factor comprises activin A.

278. The cell culture of paragraph 277, wherein said activin A is present at a concentration of about 100 ng/ml.

279. A cell culture comprising human embryonic stem cells (hESCs), a differentiation factor of the TGFβ superfamily and a medium comprising less than about 2% (v/v) serum.

280. The cell culture of paragraph 279, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

281. The cell culture of paragraph 280, wherein in cells of said cell culture, expression of a marker gene selected from the group consisting of FGF8, Nodal, HEG, HEY1, GATA2, BIK and ID1 is upregulated prior to peak expression of a marker gene selected from the group consisting of brachyury, FGF4, SNAI1, Wnt3, MIXL1, DKK4, NETO1, T, DACT1, FLJ22662, SLIT2, GAD1 and GRM4.

282. The cell culture of paragraph 281, wherein in cells of said cell culture, expression of a marker gene selected from the group consisting of HEY1, GATA2, BIK and ID1 is downregulated prior to or at about the same time as peak expression of a marker gene selected from the group consisting of brachyury, FGF4, SNAI1, Wnt3, MIXL1, DKK4, NETO1, T, DACT1, FLJ22662, SLIT2, GAD1 and GRM4.

283. The cell culture of paragraph 279, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of SOX17, FOXA2, CXCR4 and MIXL1.

284. The cell culture of paragraph 283, wherein in cells of said cell culture, expression of a marker gene selected from the group consisting of brachyury, FGF4, SNAI1, Wnt3, MIXL1, DKK4, NETO1, T, DACT1, FLJ22662, SLIT2, GAD1 and GRM4 is upregulated prior to or at about the same time as upregulation of expression of a marker gene selected from the group consisting of SOX17, FOXA2, CXCR4 and MIXL1.

285. The cell culture of paragraph 284, wherein in cells of said cell culture, peak expression of a marker gene selected from the group consisting of brachyury, FGF4, SNAI1, Wnt3, MIXL1, DKK4, NETO1, T, DACT1, FLJ22662, SLIT2, GAD1 and GRM4 is reached prior to or at about the same time as upregulation of expression of a marker gene selected from the group consisting of SOX17, FOXA2, CXCR4 and MIXL1.

286. The cell culture of paragraph 283, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

287. The cell culture of paragraph 279, wherein said medium comprises less than about 1% (v/v) serum.

288. The cell culture of paragraph 279, wherein said medium comprises less than about 0.2% (v/v) serum.

289. The cell culture of paragraph 279, wherein said medium comprises about 0% (v/v) serum.

290. The cell culture of paragraph 279, wherein said medium lacks serum or lacks serum replacement.

291. The cell culture of paragraph 279, wherein said differentiation factor of the TGFβ superfamily comprises activin A.

292. The cell culture of paragraph 291, wherein said activin A is present in the medium at a concentration of about 100 ng/ml.

293. A method of differentiating cells in a cell culture, said method comprising (a) contacting a cell culture comprising human embryonic stem cells (hESCs) with a medium comprising less that about 2% serum, (b) providing said hESCs with a differentiation factor of the TGFβ superfamily, and (c) permitting differentiation of said hESCs to occur.

294. The method of paragraph 283, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

295. The method of paragraph 294, wherein in cells of said cell culture, expression of a marker gene selected from the group consisting of FGF8, Nodal, HEG, HEY1, GATA2, BIK and ID1 is upregulated prior to peak expression of a marker gene selected from the group consisting of brachyury, FGF4, SNAI1, Wnt3, MIXL1, DKK4, NETO1, T, DACT1, FLJ22662, SLIT2, GAD1 and GRM4.

296. The method of paragraph 295, wherein in cells of said cell culture, expression of a marker gene selected from the group consisting of HEY1, GATA2, BIK and ID1 is downregulated prior to or at about the same time as peak expression of a marker gene selected from the group consisting of brachyury, FGF4, SNAI1, Wnt3, MIXL1, DKK4, NETO1, T, DACT1, FLJ22662, SLIT2, GAD1 and GRM4.

297. The method of paragraph 293, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of SOX17, FOXA2, CXCR4 and MIXL1.

298. The method of paragraph 297, wherein in cells of said cell culture, expression of a marker gene selected from the group consisting of brachyury, FGF4, SNAI1, Wnt3, MIXL1, DKK4, NETO1, T, DACT1, FLJ22662, SLIT2, GAD1 and GRM4 is upregulated prior to or at about the same time as upregulation of expression of a marker gene selected from the group consisting of SOX17, FOXA2, CXCR4 and MIXL1.

299. The method of paragraph 298, wherein in cells of said cell culture, peak expression of a marker gene selected from the group consisting of brachyury, FGF4, SNAI1, Wnt3, MIXL1, DKK4, NETO1, T, DACT1, FLJ22662, SLIT2, GAD1 and GRM4 is reached prior to or at about the same time as upregulation of expression of a marker gene selected from the group consisting of SOX17, FOXA2, CXCR4 and MIXL1.

300. The method of paragraph 297, wherein in cells of said cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

301. The method of paragraph 293, wherein said medium comprises less than about 1% (v/v) serum.

302. The method of paragraph 293, wherein said medium comprises less than about 0.2% (v/v) serum.

303. The method of paragraph 293, wherein said medium comprises about 0% (v/v) serum.

304. The method of paragraph 293, wherein said medium lacks serum or lacks serum replacement.

305. The method of paragraph 293, wherein said differentiation factor of the TGFβ superfamily comprises activin A.

306. The method of paragraph 305, wherein said activin A is present in the medium at a concentration of about 100 ng/ml.

307. A cell culture comprising human embryonic stem cells (hESCs) and a medium comprising less than about 2% (v/v) serum, wherein said hESCs begin differentiating at a reference time point such that expression of an mRNA selected from the group consisting of FZD10, FGF5 and OCT4 is substantially upregulated as compared to baseline expression of a corresponding mRNA selected from the group consisting of FZD10, FGF5 and OCT4 in said hESCs by about 2 hours from said reference time point.

308. The cell culture of paragraph 307, wherein said medium comprises less than about 1% (v/v) serum.

309. The cell culture of paragraph 307, wherein said medium comprises less than about 0.2% (v/v) serum.

310. The cell culture of paragraph 307, wherein said medium comprises about 0% (v/v) serum.

311. The cell culture of paragraph 307, wherein said medium lacks serum or lacks serum replacement.

312. The cell culture of paragraph 307 further comprising a differentiation factor of the TGFβ superfamily.

313. The cell culture of paragraph 312, wherein said differentiation factor comprises activin A.

314. The cell culture of paragraph 313, wherein said activin A is present at a concentration of about 100 ng/ml.

315. A cell culture comprising human embryonic stem cells (hESCs) and a medium comprising less than about 2% (v/v) serum, wherein said hESCs begin differentiating at a reference time point such that expression of an mRNA selected from the group consisting of GBX2, ZFP42 and SOX2 is substantially downregulated as compared to baseline expression of a corresponding mRNA selected from the group consisting of GBX2, ZFP42 and SOX2 in said hESCs by about 2 hours from said reference time point.

316. The cell culture of paragraph 315, wherein said medium comprises less than about 1% (v/v) serum.

317. The cell culture of paragraph 315, wherein said medium comprises less than about 0.2% (v/v) serum.

318. The cell culture of paragraph 315, wherein said medium comprises about 0% (v/v) serum.

319. The cell culture of paragraph 315, wherein said medium lacks serum or lacks serum replacement.

320. The cell culture of paragraph 315 further comprising a differentiation factor of the TGFβ superfamily.

321. The cell culture of paragraph 320, wherein said differentiation factor comprises activin A.

322. The cell culture of paragraph 321, wherein said activin A is present at a concentration of about 100 ng/ml.

323. A cell culture comprising human embryonic stem cells (hESCs), a differentiation factor of the TGFβ superfamily and a medium comprising less than about 2% (v/v) serum, wherein in cells of said cell culture, expression of a marker gene selected from the group consisting of FZD10, FGF5, Nanog and OCT4 is upregulated or expression of a marker gene selected from the group consisting of GBX2, ZFP42 and SOX2 is downregulated prior to upregulation of expression of a marker gene selected from the group consisting of FGF5, Nodal, HEG, HEY1, GATA2, BIK and ID1.

324. The cell culture of paragraph 323, wherein expression of a marker gene selected from the group consisting of FZD10, FGF5, Nanog and OCT4 is upregulated or expression of a marker gene selected from the group consisting of GBX2, ZFP42 and SOX2 is downregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

325. The cell culture of paragraph 323, wherein said medium comprises less than about 1% (v/v) serum.

326. The cell culture of paragraph 323, wherein said medium comprises less than about 0.2% (v/v) serum.

327. The cell culture of paragraph 323, wherein said medium comprises about 0% (v/v) serum.

328. The cell culture of paragraph 323, wherein said medium lacks serum or lacks serum replacement.

329. The cell culture of paragraph 323 further comprising a differentiation factor of the TGFβ superfamily.

330. The cell culture of paragraph 329, wherein said differentiation factor comprises activin A.

331. The cell culture of paragraph 330, wherein said activin A is present at a concentration of about 100 ng/ml.

332. A method of differentiating cells in a cell culture, said method comprising (a) contacting a cell culture comprising human embryonic stem cells (hESCs) with a medium comprising less that about 2% serum, (b) providing said hESCs with a differentiation factor of the TGFβ superfamily, and (c) permitting differentiation of said hESCs to occur, wherein in cells of said cell culture, expression of a marker gene selected from the group consisting of FZD10, FGF5, Nanog and OCT4 is upregulated or expression of a marker gene selected from the group consisting of GBX2, ZFP42 and SOX2 is downregulated prior to upregulation of expression of a marker gene selected from the group consisting of FGF5, Nodal, HEG, HEY1, GATA2, BIK and ID1.

333. The method of paragraph 332, wherein expression of a marker gene selected from the group consisting of FZD10, FGF5, Nanog and OCT4 is upregulated or expression of a marker gene selected from the group consisting of GBX2, ZFP42 and SOX2 is downregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

334. The method of paragraph 332, wherein said medium comprises less than about 1% (v/v) serum.

335. The method of paragraph 332, wherein said medium comprises less than about 0.2% (v/v) serum.

336. The method of paragraph 332, wherein said medium comprises about 0% (v/v) serum.

337. The method of paragraph 332, wherein said medium lacks serum or lacks serum replacement.

338. The method of paragraph 332 further comprising a differentiation factor of the TGFβ superfamily.

339. The method of paragraph 338, wherein said differentiation factor comprises activin A.

340. The method of paragraph 339, wherein said activin A is present at a concentration of about 100 ng/ml.

It will be appreciated that the methods and compositions described above relate to cells cultured in vitro. However, the above-described in vitro differentiated cell compositions may be used for in vivo applications.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004, U.S. patent application Ser. No. 11/115,868, entitled PDX1 EXPRESSING ENDODERM, filed Apr. 26, 2005, U.S. patent application Ser. No. 11/165,305, entitled METHODS FOR IDENTIFYING FACTORS FOR DIFFERENTIATING DEFINITIVE ENDODERM, filed Jun. 23, 2005 and U.S. Provisional Patent Application No. 60/693,364, entitled PREPRIMITIVE STREAK CELLS AND MESENDODERM CELLS, filed Jun. 23, 2005, the disclosures of which are incorporated herein by reference in their entireties.

DETAILED DESCRIPTION

Figure 1:
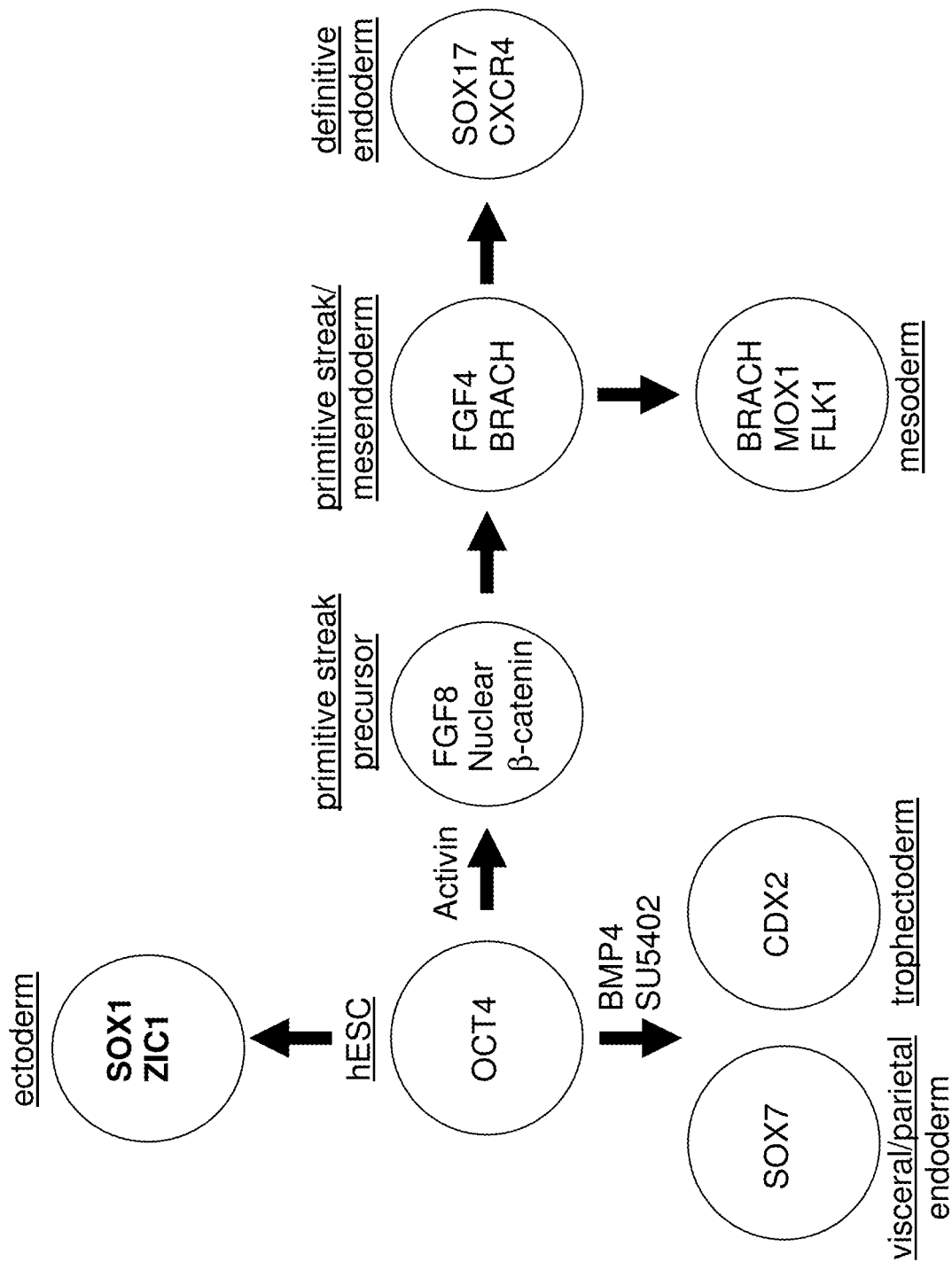
FIG. 1 is a diagram depicting the differentiation of embryonic stem cells (ESC) in the presence of activins, in the presence of a combination of BMP4 and SU5402, and in the absence of any differentiation factors. Some useful marker genes for the identification and/or detection of each cell type are also listed.
Figure 2A:
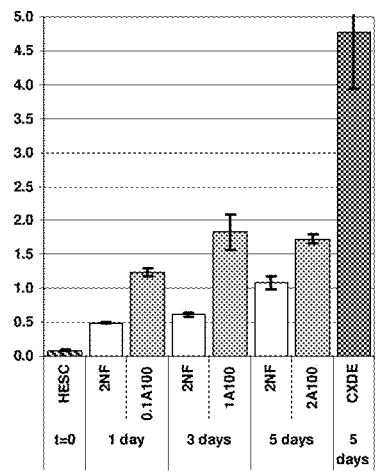
FIGS. 2A-2M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml activin A; 1A100 indicates cells treated with 1% FBS, 100 ng/ml activin A; and 2A100 indicates cells treated with 2% FBS, 100 ng/ml activin A.
Figure 2B:
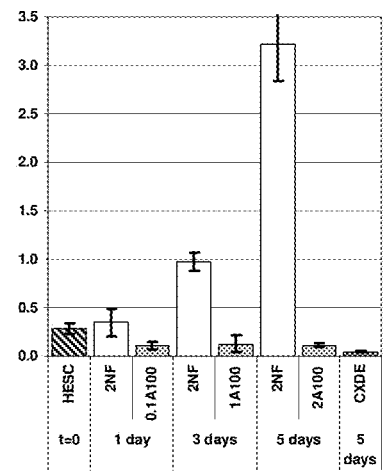
Figure 2C:
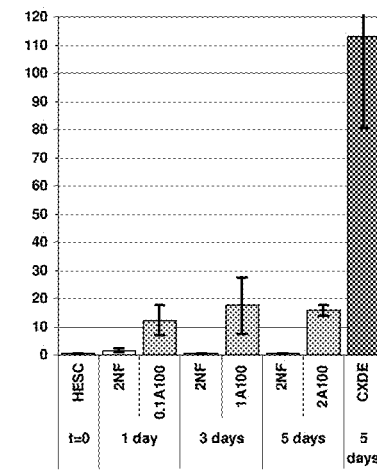
Figure 2D:
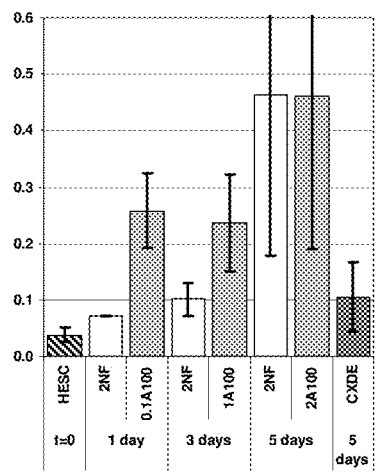
Figure 2E:
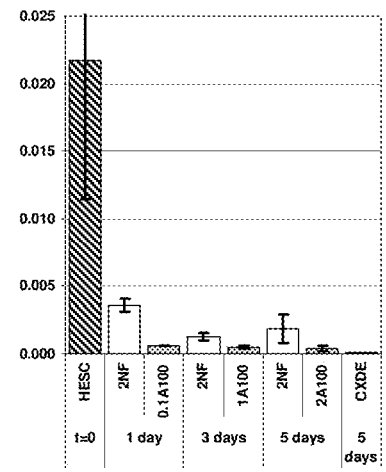
Figure 2F:
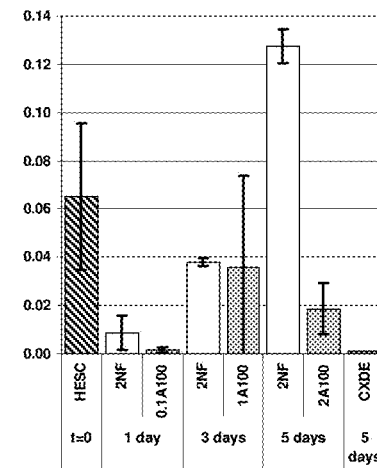
Figure 2G:
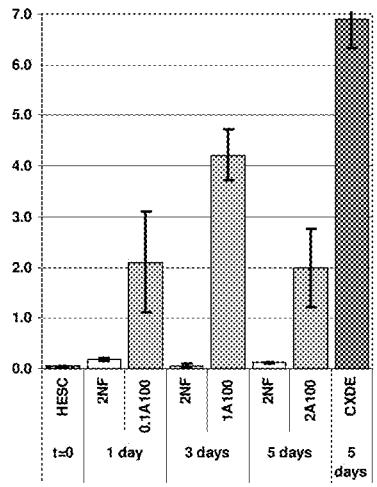
Figure 2H:
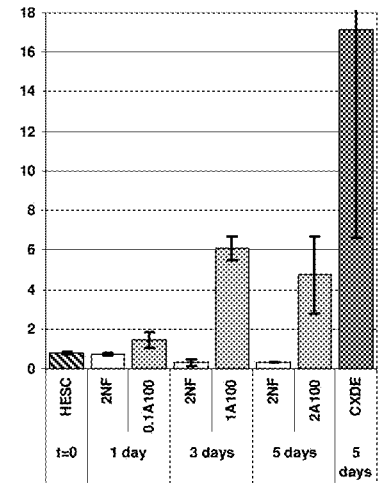
Figure 2I:
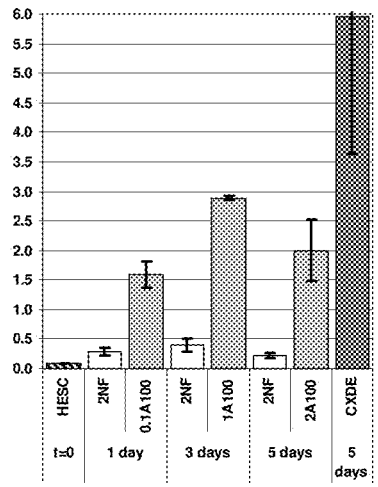
Figure 2J:
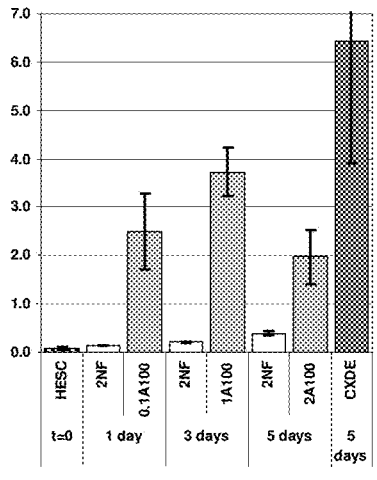
Figure 2K:
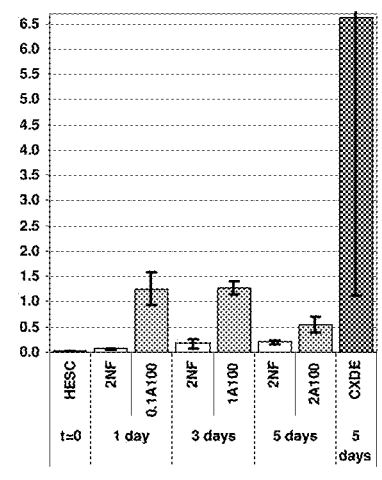
Figure 2L:
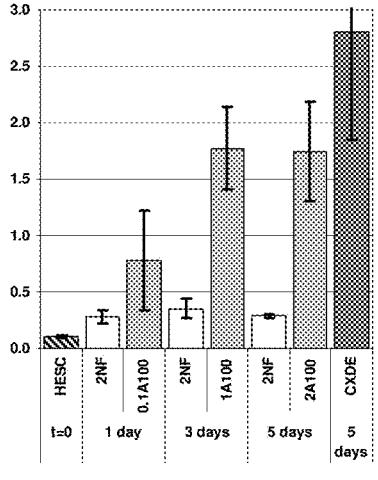
Figure 2M:
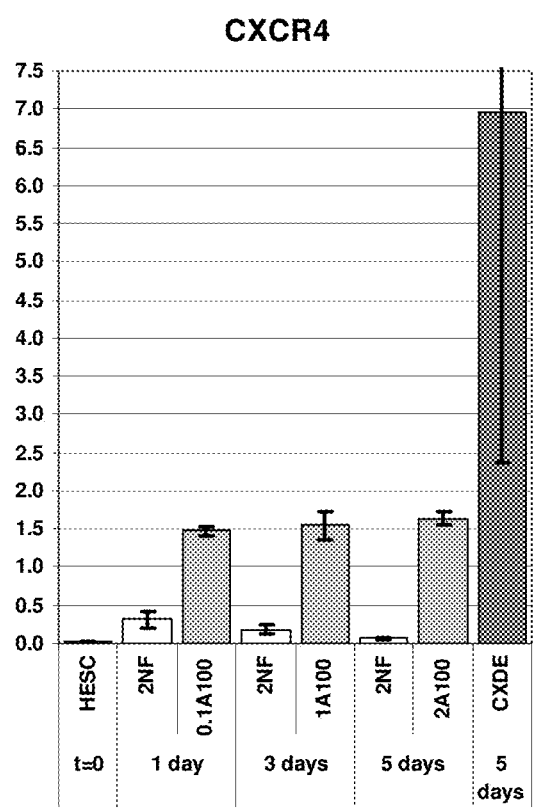

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. As the mesendoderm cells ingress through the primitive streak, they undergo an epithelial to mesenchymal transition (EMT) and become either mesoderm or definitive endoderm. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

Both primitive streak precursor cells (preprimitive streak cells) and primitive streak cells (mesendoderm cells) are early stage precursor cells the give rise to the mesoderm and the definitive endoderm. In fact, preprimitive streak cells and mesendoderm cells may be the earliest precursors in the developmental process from pluripotency to terminally differentiated cells, tissues and/or organs made from the mesoderm and definitive endoderm lineages. Until now, neither cell populations enriched in human preprimitive streak cells nor cell populations enriched in human mesendoderm cells have been obtained. Furthermore, the cells of such cell populations have not been previously characterized in vitro.

In view of the foregoing, some embodiments of the invention described herein relate to cell cultures and/or enriched cell populations comprising human preprimitive streak cells and cell cultures and/or enriched cell populations comprising human mesendoderm cells. In such embodiments, the preprimitive streak cells and the mesendoderm cells are capable of further differentiation into mesoderm cells and/or definitive endoderm cells as well as cells, tissues and/or organs derived from these lineages.

Other embodiments of the invention relate to methods for producing cell cultures and/or enriched cell populations comprising human preprimitive streak cells as well as methods for producing cell cultures and/or enriched cell populations comprising human mesendoderm cells.

Still other embodiments described herein relate to screening methods for identifying one or more differentiation factors that are useful for differentiating cells in a cell population comprising preprimitive streak cells or mesendoderm cells. Such factors are useful for promoting the differentiation of these cell types to mesoderm and/or definitive endoderm cells as well as cells, tissues and/or organs derived from either of these cell lineages.

Certain other aspects of the present invention relate to methods for increasing the expression of certain early stage cell markers. Further aspects relate to cell compositions comprising cells expressing certain markers during the course of differentiation.

Definitions

Certain terms and phrases as used throughout this application have the meanings provided as follows:

As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

As used herein, "multipotent" or "multipotent cell" refers to a cell type that can give rise to a limited number of other particular cell types.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule (for example, molecules having a molecular weight of less than 10,000 amu)

When used in connection with cell cultures and/or cell populations, the term "portion" means any non-zero amount of the cell culture or cell population, which ranges from a single cell to the entirety of the cell culture or cells population.

With respect to cells in cell cultures or in cell populations, the phrase "substantially free of" means that the specified cell type of which the cell culture or cell population is free, is present in an amount of less than about 5% of the total number of cells present in the cell culture or cell population.

With respect to cell culture medium, as used herein, "low serum RPMI" refers to a low serum containing medium, wherein the serum concentration is gradually increased over a defined time period. For example, in one embodiment, low serum RPMI comprises a concentration of about 0.2% fetal bovine serum (FBS) on the first day of cell growth, about 0.5% FBS on the second day of cell growth and about 2% FBS on the third through fifth day of cell growth. In another embodiment, low serum RPMI comprises a concentration of about 0% on day one, about 0.2% on day two and about 2% on the third and subsequent days.

As used herein, "serum replacement" refers to serum substitute comprising IGF or insulin.

Model of Early Events in the Differentiation of hESCs to Definitive Endoderm Cells FIG. 1 displays a model summarizing the early transitions of human embryonic stem cells (hESCs) in vitro. Differentiation of hESCs through a process that closely recapitulates gastrulation can be orchestrated by the application of high dose activin A in the context of low serum supplementation. The expression of FGF8 and nuclear localization of β-catenin, events that occur in the proximal epiblast prior to primitive streak formation, is evident prior to about 24 hours (preprimitive streak cells). High level expression of the primitive streak-expressed genes (brachyury and FGF4) occurs at about 24 hours. If maintained in high dose activin A, the primitive streak cells (mesendoderm cells) are efficiently converted into definitive endoderm. In contrast, in the absence of activins, these mesendoderm precursors become mesoderm. Treatment of hESCs with BMP4 and SU5402 induces gene expression associated with primitive endoderm and trophectoderm.

Preprimitive Streak Cells and Mesendoderm Cells and Processes Related Thereto

Embodiments described herein relate to novel, defined processes for the production of preprimitive streak cells and/or mesendoderm cells in culture by differentiating pluripotent cells, such as stem cells into preprimitive streak cells and/or mesendoderm cells. As described above, preprimitive streak cells are capable of differentiating into mesendoderm cells as well as cells, tissues and/or organs derived therefrom. Mesendoderm cells are capable of differentiating into mesoderm cells and/or definitive endoderm cells as well as cells, tissues and/or organs derived from either of these lineages. In some embodiments, the preprimitive steak cells are converted, through a mesendoderm intermediate, into terminally differentiated cells of either the mesoderm or definitive endoderm lineages. As will be described in further detail below, such processes can provide the basis for efficient production of a variety of human endodermal and mesodermal derived tissues. For example, such processes can provide the basis for efficient production of human endodermal derived tissues, such as pancreas, liver, lungs, stomach, intestine, thyroid, thymus, pharynx, gallbladder and urinary bladder. Importantly, production of preprimitive streak cells and/or mesendoderm cells is an early step in differentiation of a stem cell to a functional insulin-producing β-cell. As another example, preprimitive streak cell and/or mesendoderm cell differentiation can provide the basis for efficient production of human mesodermal derived tissues, such as blood cells, cardiovascular tissues, skeletal tissues as well as other structural and connective tissues. To obtain useful quantities of any of the above-described cell or tissue types, high efficiency differentiation is desirable for each of the differentiation steps that occur prior to reaching the terminally differentiated cell fate. Since differentiation of stem cells to preprimitive streak cells and/or mesendoderm cells represents very early steps towards the production of functional terminally differentiated cells of the mesoderm and definitive endoderm cell lineages (as shown in FIG. 1), high efficiency differentiation at this step is particularly desirable.

In view of the desirability of efficient differentiation of pluripotent cells to preprimitive streak cells and/or mesendoderm cells, some aspects of the differentiation processes described herein relate to in vitro methodology that results in approximately 5-90% conversion of pluripotent cells to preprimitive streak cells and/or mesendoderm cells. Typically, such methods encompass the application of culture and growth factor conditions in a defined and temporally specified fashion. Further enrichment of the cell population for preprimitive streak cells and/or mesendoderm cells can be achieved by isolation and/or purification of the preprimitive streak cells and/or mesendoderm cells from other cells in the population by sorting cells based on differential fluorescent marker expression. As such, some embodiments described herein relate to preprimitive streak cells as well as methods for producing and isolating and/or purifying such cells. Other embodiments relate to mesendoderm cells as well as methods for producing and isolating and/or purifying such cells.

In order to determine the amount of preprimitive streak cells in a cell culture or cell population, a method of distinguishing this cell type from the other cells in the culture or in the population is desirable. Accordingly, certain embodiments described herein relate to cell markers whose presence, absence and/or relative expression levels are specific for preprimitive streak cells and methods for detecting and determining the expression of such markers.

In some embodiments described herein, the presence, absence and/or level of expression of a marker is determined by quantitative PCR (Q-PCR). For example, the amount of transcript produced by certain genetic markers, such as OCT4, ECAD, FGF8, β-catenin, brachyury, FGF4, SNAI1, SOX17, CXCR4, GSC, MIXL1, FOXA2, SOX7, FOXF1, FLK1, BML4, MOX1, SDF1 and other markers described herein is determined by quantitative Q-PCR. In other embodiments, immunohistochemistry is used to detect the proteins expressed by the above-mentioned genes. In still other embodiments, immunohistochemistry/immunocytochemistry is used to detect cell compartmental localization of certain polypeptide markers, such as the nuclear localization of β-catenin. In yet other embodiments, Q-PCR and immunohistochemical techniques are both used to identify and determine the amount or relative proportions of such markers.

By using methods, such as those described above, to determine the expression of one or more appropriate markers, it is possible to identify preprimitive streak cells and/or mesendoderm cells, as well as determine the proportion of preprimitive streak cells and/or mesendoderm cells in a cell culture or cell population. For example, in some embodiments of the present invention, the preprimitive streak cells or cell populations that are produced express the FGF8 marker and/or nuclear-localized β-catenin at a level of about 2 orders of magnitude greater than non-preprimitive streak cell types or cell populations. In other embodiments, the preprimitive streak cells or cell populations that are produced express the FGF8 marker and/or nuclear-localized β-catenin at a level of more than 2 orders of magnitude greater than non-preprimitive streak cell types or cell populations. In other embodiments of the present invention, the mesendoderm cells or cell populations that are produced express the brachyury, FGF4 and/or SNAI1 markers at a level of about 2 orders of magnitude greater than non-mesendoderm cell types or cell populations. In other embodiments, the mesendoderm cells or cell populations that are produced express the brachyury, FGF4 and/or SNAI1 markers at a level of more than 2 orders of magnitude greater than non-mesendoderm cell types or cell populations.

Embodiments described herein also relate to preprimitive streak and/or mesendoderm compositions. For example, some embodiments relate to cell cultures comprising preprimitive streak cells and/or mesendoderm cells, whereas others relate to cell populations enriched in preprimitive streak cells and/or mesendoderm cells. Some preferred embodiments relate to cell cultures which comprise preprimitive streak cells and/or mesendoderm cells, wherein at least about 5-90% of the cells in culture are preprimitive streak cells and/or mesendoderm cells. An especially preferred embodiment relates to cells cultures comprising human cells, wherein at least about 5-90% of the human cells in culture are preprimitive streak cells and/or mesendoderm cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to preprimitive streak cells and/or mesendoderm cells. In other preferred embodiments, conversion of a pluripotent cell population, such as a stem cell population, to substantially pure preprimitive streak cell and/or mesendoderm cell population is contemplated.

The compositions and methods described herein have several useful features. For example, the cell cultures and cell populations comprising preprimitive streak cells and/or mesendoderm cells as well as the methods for producing such cell cultures and cell populations are useful for modeling the early stages of human development. Furthermore, the compositions and methods described herein can also serve for therapeutic intervention in disease states, such as diabetes mellitus. For example, since preprimitive streak cells and/or mesendoderm cells serve as the source for only a limited number of tissues, they can be used in the development of pure tissue or cell types.

Production of Preprimitive Streak Cells from Pluripotent Cells

In some processes for producing preprimitive streak cells, the pluripotent cells used as starting material are stem cells. In certain processes, preprimitive streak cell cultures and enriched cell populations comprising preprimitive streak cells are produced from embryonic stem cells. A preferred method for deriving preprimitive streak cells utilizes human embryonic stem cells as the starting material for preprimitive streak cell production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some processes for producing preprimitive streak cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing preprimitive streak cells permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into preprimitive streak cells. In some processes, differentiation to preprimitive streak cells is achieved by providing to the stem cell culture a differentiation factor, such as a growth factor of the TGFβ superfamily, in an amount sufficient to promote differentiation to preprimitive streak cells. Growth factors of the TGFβ superfamily which are useful for the production of preprimitive streak cells are selected from the Nodal/Activin subgroups. In some preferred differentiation processes, the growth factor is selected from the group consisting of Nodal, activin A, and activin B. In certain differentiation processes, the growth factor activin A is used.

With respect to some of the processes for the differentiation of pluripotent stem cells to preprimitive streak cells, the above-mentioned growth factors are provided to the cells so that the growth factors are present in the cultures at concentrations sufficient to promote differentiation of at least a portion of the stem cells to preprimitive streak cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to preprimitive streak cells, the above-mentioned growth factors are removed from the cell culture subsequent to their addition. For example, the growth factors can be removed within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours or within about more than 24 hours.

Cultures of preprimitive streak cells can be grown in medium containing reduced serum or no serum. Under certain culture conditions, serum concentrations can range from about 0% (v/v) to about 10% (v/v). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v) or less than about 10% (v/v). In some processes, preprimitive streak cells are grown without serum or without serum replacement. In still other processes, preprimitive streak cells are grown in the presence of B27. In such processes, the concentration of B27 supplement can range from about 0.1% (v/v) to about 20% (v/v).

Monitoring the Differentiation of Pluripotent Cells to Preprimitive Streak Cells The progression of the hESC culture to preprimitive streak cells can be monitored by determining the temporal expression of markers characteristic of preprimitive streak cells. In some processes, the expression of certain markers is determined by detecting the presence or absence of the marker. Alternatively, the expression of certain markers can be determined by measuring the level at which the marker is present in the cells of the cell culture or cell population at one or more time points subsequent to the addition of the differentiation factor. In such processes, the measurement of marker expression can be qualitative or quantitative. One method of quantitating the expression of markers that are produced by marker genes is through the use of quantitative polymerase chain reaction (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of preprimitive streak cells as well as the lack of significant expression of marker genes characteristic of hESCs and other cell types is determined. In still other processes, both the timing and amount of expression of marker genes characteristic of preprimitive streak cells at one or more time points subsequent to the addition of the differentiation factor is determined.

As described further in the Examples below, markers of preprimitive streak cells are FGF8 and β-catenin. As such, the preprimitive streak cells produced by the processes described herein express the FGF8 and β-catenin marker genes, thereby producing the FGF8 and β-catenin marker gene products. In some embodiments, the FGF8 mRNA is substantially expressed in preprimitive streak cells but not in hESCs. Substantial upregulation of the FGF8 mRNA, to near peak levels, can be observed in a differentiating hESC culture by 6 hours after contacting the hESCs with an appropriate differentiation factor, such as activin A. At this time, expression of markers indicative of other cells types, such as mesendoderm, primitive endoderm, definitive endoderm, mesoderm and ectoderm (see Table 1), is still comparatively low. In some embodiments, markers indicative of mesendoderm, primitive endoderm, definitive endoderm, mesoderm and ectoderm are not substantially expressed by 6 hours after contacting the hESCs with the differentiation factor. FGF8 mRNA expression is maintained at high levels for at least about 24 hours after contacting the hESCs with the differentiation factor but begins to decline thereafter. Additionally, by about 17 hours after contacting the hESCs with an appropriate differentiation factor, such as activin A, nuclear localization of the β-catenin polypeptide (the expression of nuclear-localized β-catenin) is observed by immunocytochemistry. In hESCs, the β-catenin polypeptide is present at the cell periphery but not in the nucleus.

It will be appreciated that FGF8 and nuclear-localized β-catenin expression is induced over a range of different levels in preprimitive streak cells depending on the differentiation conditions. As such, in some embodiments described herein, the expression of the FGF8 marker and/or the nuclear-localized β-catenin marker in preprimitive streak cells or cell populations is at least about 2-fold higher to at least about 10,000-fold higher than the expression of these markers in non-preprimitive streak cells or cell populations, during about the first 6 to 18 hours of differentiation from hESCs. In other embodiments, the expression of the FGF8 marker and/or the nuclear-localized β-catenin marker in preprimitive streak cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the FGF8 marker and/or the nuclear-localized β-catenin marker in non-preprimitive streak cells or cell populations, during about the first 6 to 18 hours of differentiation from hESCs. In some embodiments, the expression of the FGF8 marker and/or the nuclear-localized β-catenin marker in preprimitive streak cells or cell populations is infinitely higher than the expression of the FGF8 marker and/or the nuclear-localized β-catenin marker in non-preprimitive streak cells or cell populations, during about the first 6 to 18 hours of differentiation from hESCs.

Additionally, it will be appreciated that there is a range of differences between the expression level of the FGF8 marker and the expression levels of the brachyury, FGF4, SNAI1, SOX17, FOXA2, SOX7 and/or SOX1 markers in preprimitive streak cells. Similarly, there exists a range of differences between the expression level of the nuclear-localized β-catenin marker and the expression levels of the brachyury, FGF4, SNAI1, SOX17, FOXA2, SOX7 and/or SOX1 markers in preprimitive streak cells. As such, in some embodiments described herein, the expression of the FGF8 marker and/or the nuclear-localized β-catenin marker is at least about 2-fold higher to at least about 10,000-fold higher than the expression of the brachyury, FGF4, SNAI1, SOX17, FOXA2, SOX7 and/or SOX1 markers. In other embodiments, the expression of the FGF8 marker and/or the nuclear-localized β-catenin marker is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the brachyury, FGF4, SNAI1, SOX17, FOXA2, SOX7 and/or SOX1 markers. In some embodiments, the brachyury, FGF4, SNAI1, SOX17, FOXA2, SOX7 and/or SOX1 markers are not significantly expressed in preprimitive streak cells.

Enrichment, Isolation and/or Purification of Preprimitive Streak Cells

With respect to additional aspects of the processes described herein, preprimitive streak cells can be enriched, isolated and/or purified. In some embodiments, cell populations enriched for preprimitive streak cells are produced by isolating such cells from cell cultures.

In some embodiments of the processes described herein, preprimitive streak cells are fluorescently labeled then isolated from non-labeled cells by using a fluorescence activated cell sorter (FACS). In such embodiments, a nucleic acid encoding green fluorescent protein (GFP) or another nucleic acid encoding an expressible fluorescent marker gene is used to label preprimitive streak cells. For example, in some embodiments, at least one copy of a nucleic acid encoding GFP or a biologically active fragment thereof is introduced into a pluripotent cell, preferably a human embryonic stem cell, downstream of the FGF8 promoter such that the expression of the GFP gene product or biologically active fragment thereof is under control of the FGF8 promoter. In some embodiments, the entire coding region of the nucleic acid, which encodes FGF8, is replaced by a nucleic acid encoding GFP or a biologically active fragment thereof. In other embodiments, the nucleic acid encoding GFP or a biologically active fragment thereof is fused in frame with at least a portion of the nucleic acid encoding FGF8, thereby generating a fusion protein. In such embodiments, the fusion protein retains a fluorescent activity similar to GFP.

Fluorescently marked cells, such as the above-described pluripotent cells, are differentiated to preprimitive streak cells as described previously above. Because preprimitive streak cells express the fluorescent marker gene, whereas non-preprimitive streak cells do not, these two cell types can be separated. In some embodiments, cell suspensions comprising a mixture of fluorescently-labeled preprimitive streak cells and unlabeled non-preprimitive streak cells are sorted using a FACS. Preprimitive streak cells are collected separately from non-preprimitive streak cells, thereby resulting in the isolation of such cell types. If desired, the isolated cell compositions can be further purified by additional rounds of sorting using the same or different markers that are specific for preprimitive streak cells.

In addition to the procedures just described, preprimitive streak cells may also be isolated by other techniques for cell isolation. Additionally, preprimitive streak cells may also be enriched or isolated by methods of serial subculture in growth conditions which promote the selective survival or selective expansion of the preprimitive streak cells.

It will be appreciated that the above-described enrichment, isolation and purification procedures can be used with such cultures at any stage of differentiation.

Using the methods described herein, enriched, isolated and/or purified populations of preprimitive streak cells and/or tissues can be produced in vitro from hESC cultures or cell populations which have undergone differentiation for from about 1 hour to about 24 hours. In some embodiments, the cells undergo random differentiation. In a preferred embodiment, however, the cells are directed to differentiate primarily into preprimitive streak cells. Some preferred enrichment, isolation and/or purification methods relate to the in vitro production of preprimitive streak cells from human embryonic stem cells.

Using the methods described herein, cell populations or cell cultures can be enriched in preprimitive streak cell content by at least about 2- to about 1000-fold as compared to untreated or unenriched cell populations or cell cultures. In some embodiments, preprimitive streak cells can be enriched by at least about 5- to about 500-fold as compared to untreated or unenriched cell populations or cell cultures. In other embodiments, preprimitive streak cells can be enriched from at least about 10- to about 200-fold as compared to untreated or unenriched cell populations or cell cultures. In still other embodiments, preprimitive streak cells can be enriched from at least about 20- to about 100-fold as compared to untreated or unenriched cell populations or cell cultures. In yet other embodiments, preprimitive streak cells can be enriched from at least about 40- to about 80-fold as compared to untreated or unenriched cell populations or cell cultures. In certain embodiments, preprimitive streak cells can be enriched from at least about 2- to about 20-fold as compared to untreated or unenriched cell populations or cell cultures.

Compositions Comprising Preprimitive Streak Cells

Cell compositions produced by the above-described methods include cell cultures comprising preprimitive streak cells and cell populations enriched in preprimitive streak cells. For example, cell cultures which comprise preprimitive streak cells, wherein at least about 5-90% of the cells in culture are preprimitive streak cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to preprimitive streak cells. In processes in which isolation of preprimitive streak cells is employed, a substantially pure preprimitive streak cell population can be recovered.

Some embodiments described herein relate to compositions, such as cell populations and cell cultures, that comprise both pluripotent cells, such as stem cells, and preprimitive streak cells. For example, using the methods described herein, compositions comprising mixtures of hESCs and preprimitive streak cells can be produced. In some embodiments, compositions comprising at least about 5 preprimitive streak cells for about every 95 pluripotent cells are produced. In other embodiments, compositions comprising at least about 95 preprimitive streak cells for about every 5 pluripotent cells are produced. Additionally, compositions comprising other ratios of preprimitive streak cells to pluripotent cells are contemplated. For example, compositions comprising at least about 1 preprimitive streak cell for about every 1,000,000 pluripotent cells, at least about 1 preprimitive streak cell for about every 100,000 pluripotent cells, at least about 1 preprimitive streak cell for about every 10,000 pluripotent cells, at least about 1 preprimitive streak cell for about every 1000 pluripotent cells, at least about 1 preprimitive streak cell for about every 500 pluripotent cells, at least about 1 preprimitive streak cell for about every 100 pluripotent cells, at least about 1 preprimitive streak cell for about every 10 pluripotent cells, at least about 1 preprimitive streak cell for about every 5 pluripotent cells, at least about 1 preprimitive streak cell for about every 2 pluripotent cells, at least about 2 preprimitive streak cells for about every 1 pluripotent cell, at least about 5 preprimitive streak cells for about every 1 pluripotent cell, at least about 10 preprimitive streak cells for about every 1 pluripotent cell, at least about 20 preprimitive streak cells for about every 1 pluripotent cell, at least about 50 preprimitive streak cells for about every 1 pluripotent cell, at least about 100 preprimitive streak cells for about every 1 pluripotent cell, at least about 1000 preprimitive streak cells for about every 1 pluripotent cell, at least about 10,000 preprimitive streak cells for about every 1 pluripotent cell, at least about 100,000 preprimitive streak cells for about every 1 pluripotent cell and at least about 1,000,000 preprimitive streak cells for about every 1 pluripotent cell are contemplated. In some embodiments, the pluripotent cells are human pluripotent stem cells. In certain embodiments, the stem cells are derived from a morula, the inner cell mass of an embryo or the gonadal ridges of an embryo. In certain other embodiments, the pluripotent cells are derived from the gonadal or germ tissues of a multicellular structure that has developed past the embryonic stage.

Some embodiments described herein relate to cell cultures or cell populations comprising from at least about 5% preprimitive streak cells to at least about 99% preprimitive streak cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are preprimitive streak cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are preprimitive streak cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human cells, such as human preprimitive streak cells, wherein the expression of the FGF8 marker and/or the nuclear-localized β-catenin marker is greater than the expression of the brachyury, FGF4, SNAI1, SOX17, FOXA2, SOX7 and/or SOX1 markers in at least about 5% of the human cells. In other embodiments, the expression of either the FGF8 marker and/or the nuclear-localized β-catenin marker is greater than the expression of the brachyury, FGF4, SNAI1, SOX17, FOXA2, SOX7 and/or SOX1 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells, in at least about 98% of the human cells, in at least about 99% of the human cells or in greater than 99% of the human cells. In embodiments where the cell cultures or cell populations comprise human feeder cells, the above percentages are calculated without respect to the human feeder cells in the cell cultures or cell populations.

Additional embodiments described herein relate to compositions, such as cell cultures or cell populations, comprising human hESCs and human preprimitive streak cells, wherein substantial upregulation of the expression of FGF8 mRNA occurs in cells of the cell culture or cell population by about 1 hour, by about 2 hours, by about 3 hours, by about 4 hours, by about 5 hours, by about 6 hours, by about 7 hours, by about 8 hours, by about 9 hours, by about 10 hours, by about 11 hours, by about 12 hours, by about 13 hours, by about 14 hours, by about 15 hours, by about 16 hours, by about 17 hours, by about 18 hours, by about 19 hours, by about 20 hours, by about 21 hours, by about 22 hours, by about 23 hours, by about 24 hours, or by greater than about 24 hours after contacting hESCs in the culture with an appropriate differentiation factor, such as activin A. In such embodiments, substantial upregulation of the expression of FGF8 mRNA occurs in at least about 5% of the human cells, at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells, in at least about 98% of the human cells, in at least about 99% of the human cells or in greater than 99% of the human cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human hESCs and human preprimitive streak cells, wherein substantial nuclear localization of the β-catenin polypeptide (expression of nuclear localized β-catenin marker) occurs in cells of the cell culture or cell population by about 1 hour, by about 2 hours, by about 3 hours, by about 4 hours, by about 5 hours, by about 6 hours, by about 7 hours, by about 8 hours, by about 9 hours, by about 10 hours, by about 11 hours, by about 12 hours, by about 13 hours, by about 14 hours, by about 15 hours, by about 16 hours, by about 17 hours, by about 18 hours, by about 19 hours, by about 20 hours, by about 21 hours, by about 22 hours, by about 23 hours, by about 24 hours, or by greater than about 24 hours after contacting hESCs in the culture with an appropriate differentiation factor, such as activin A. In such embodiments, expression of nuclear-localized β-catenin occurs in at least about 5% of the human cells, at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells, in at least about 98% of the human cells, in at least about 99% of the human cells or in greater than 99% of the human cells. In embodiments where the cell cultures or cell populations comprise human feeder cells, the above percentages are calculated without respect to the human feeder cells in the cell cultures or cell populations.

Using the methods described herein, compositions comprising preprimitive streak cells substantially free of other cell types can be produced. In some embodiments described herein, the preprimitive streak cell populations or cell cultures produced by the methods described herein are substantially free of cells that significantly express the brachyury, FGF4, SNAI1, SOX17, FOXA2, SOX7 and/or SOX1 marker genes.

In one embodiment, a description of a preprimitive streak cell based on the expression of marker genes is, FGF8 high, nuclear-localized β-catenin high, brachyury low, FGF4 low, SNAI1 low, SOX17 low, FOXA2 low, SOX7 low and SOX1 low.

Production of Mesendoderm Cells from Pluripotent Cells

In some processes for producing mesendoderm cells, the pluripotent cells used as starting material are stem cells. In certain processes, mesendoderm cell cultures and enriched cell populations comprising mesendoderm cells are produced from embryonic stem cells. A preferred method for deriving mesendoderm cells utilizes human embryonic stem cells as the starting material for mesendoderm cell production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843, 780, 6,200,806 and 6,251,671 the disclosures of which are incorporated herein by reference in their entireties.

In some processes for producing mesendoderm cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing mesendoderm cells permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into mesendoderm cells. In some processes, differentiation to mesendoderm cells is achieved by providing to the stem cell culture a differentiation factor, such as a growth factor of the TGFβ superfamily, in an amount sufficient to promote differentiation to mesendoderm cells. Growth factors of the TGFβ superfamily which are useful for the production of mesendoderm cells are selected from the Nodal/Activin subgroups. In some preferred differentiation processes, the growth factor is selected from the group consisting of Nodal, activin A, and activin B. In certain differentiation processes, the growth factor activin A is used.

With respect to some of the processes for the differentiation of pluripotent stem cells to mesendoderm cells, the above-mentioned growth factors are provided to the cells so that the growth factors are present in the cultures at concentrations sufficient to promote differentiation of at least a portion of the stem cells to mesendoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to mesendoderm cells, the above-mentioned growth factors are removed from the cell culture subsequent to their addition. For example, the growth factors can be removed within about 18 hours, within about 19 hours, within about 20 hours, within about 21 hours, within about 22 hours, within about 23 hours, within about 24 hours, within about 25 hours, within about 26 hours, within about 27 hours, within about 28 hours, within about 29 hours, within about 30 hours, within about 31 hours, within about 32 hours, within about 33 hours, within about 34 hours, within about 35 hours, within about 36 hours, within about 37 hours, within about 38 hours, within about 39 hours, within about 40 hours, within about 41 hours, within about 42 hours, within about 43 hours, within about 44 hours, within about 45 hours, within about 46 hours, within about 47 hours, within about 48 hours or within about more than 48 hours.

Cultures of mesendoderm cells can be grown in medium containing reduced serum or no serum. Under certain culture conditions, serum concentrations can range from about 0% (v/v) to about 10% (v/v). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v) or less than about 10% (v/v). In some processes, mesendoderm cells are grown without serum or without serum replacement. In still other processes, mesendoderm cells are grown in the presence of B27. In such processes, the concentration of B27 supplement can range from about 0.1% (v/v) to about 20% (v/v).

Monitoring the Differentiation of Pluripotent Cells to Mesendoderm Cells

The progression of the hESC culture to mesendoderm cells can be monitored by determining the temporal expression of markers characteristic of mesendoderm cells. In some processes, the expression of certain markers is determined by detecting the presence or absence of the marker. Alternatively, the expression of certain markers can be determined by measuring the level at which the marker is present in the cells of the cell culture or cell population at one or more time points subsequent to the addition of the differentiation factor. In such processes, the measurement of marker expression can be qualitative or quantitative. One method of quantitating the expression of markers that are produced by marker genes is through the use of Q-PCR. Other methods which are known in the art can also be used to quantitate marker gene expression. For example, the expression of a marker gene product can be detected by using antibodies specific for the marker gene product of interest. In certain processes, the expression of marker genes characteristic of mesendoderm cells as well as the lack of significant expression of marker genes characteristic of hESCs and other cell types is determined. In still other processes, both the timing and amount of expression of marker genes characteristic of mesendoderm cells at one or more time points subsequent to the addition of the differentiation factor is determined.

As described further in the Examples below, markers of mesendoderm cells are brachyury, FGF4 and SNAI1. As such, the mesendoderm cells produced by the processes described herein express the brachyury, FGF4 and SNAI1 marker genes, thereby producing the brachyury, FGF4 and SNAI1 marker gene products. In some embodiments, the brachyury, FGF4 and/or SNAI1 mRNA is substantially expressed in mesendoderm cells but not in hESCs. Substantial upregulation of the brachyury, FGF4 and/or SNAI1 mRNA, to near peak levels, can be observed in a differentiating hESC culture by 24 hours after contacting the hESCs with an appropriate differentiation factor, such as activin A. At this time, expression of certain markers indicative of other cells types, such as primitive endoderm, definitive endoderm, mesoderm and ectoderm (see Table 1), is still comparatively low. In some embodiments, certain markers indicative of primitive endoderm, definitive endoderm, mesoderm and ectoderm are not substantially expressed by 24 hours after contacting the hESCs with the differentiation factor. In some embodiments, brachyury, FGF4 and/or SNAI1 mRNA expression begins to decline after about 24 hours subsequent to contacting the hESCs with the differentiation factor. In some embodiments, brachyury, FGF4 and/or SNAI1 mRNA expression begins to decline after about 30 hours, after about 36 hours, after about 42 hours, after about 48 hours or after more than about 48 hours subsequent to contacting the hESCs with the differentiation factor.

It will be appreciated that brachyury, FGF4 and/or SNAI1 expression is induced over a range of different levels in mesendoderm cells depending on the differentiation conditions. As such, in some embodiments described herein, the expression of the brachyury, FGF4 and/or SNAI1 marker in mesendoderm cells or cell populations is at least about 2-fold higher to at least about 10,000-fold higher than the expression of these markers in non-mesendoderm cells or cell populations, after about 24 hours of differentiation from hESCs. In other embodiments, the expression of the brachyury, FGF4 and/or SNAI1 marker in mesendoderm cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the brachyury, FGF4 and/or SNAI1 in non-mesendoderm cells or cell populations, after about 24 hours of differentiation from hESCs. In some embodiments, the expression of the brachyury, FGF4 and/or SNAI1 marker in mesendoderm cells or cell populations is infinitely higher than the expression of the brachyury, FGF4 and/or SNAI1 marker in non-mesendoderm cells or cell populations, after about 24 hours of differentiation from hESCs.

Additionally, it will be appreciated that there is a range of differences between the expression level of the brachyury, FGF4 and/or SNAI1 markers and the expression levels of the OCT4, SOX17, CXCR4, FOXA2, SOX7 and/or SOX1 markers in mesendoderm cells. As such, in some embodiments described herein, the expression of the brachyury, FGF4 and/or SNAI1 markers is at least about 2-fold higher to at least about 10,000-fold higher than the expression of the OCT4, SOX17, CXCR4, FOXA2, SOX7 and/or SOX1 markers. In other embodiments, the expression of the brachyury, FGF4 and/or SNAI1 marker is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the OCT4, SOX17, CXCR4, FOXA2, SOX7 and/or SOX1 markers. In some embodiments, the OCT4, SOX17, CXCR4, FOXA2, SOX7 and/or SOX1 markers are not significantly expressed in mesendoderm cells.

Enrichment, Isolation and/or Purification of Mesendoderm Cells

With respect to additional aspects of the processes described herein, mesendoderm cells can be enriched, isolated and/or purified. In some embodiments, cell populations enriched for mesendoderm cells are produced by isolating such cells from cell cultures.

In some embodiments of the processes described herein, mesendoderm cells are fluorescently labeled then isolated from non-labeled cells by using a FACS. In such embodiments, a nucleic acid encoding green fluorescent protein (GFP) or another nucleic acid encoding an expressible fluorescent marker gene is used to label mesendoderm cells. For example, in some embodiments, at least one copy of a nucleic acid encoding GFP or a biologically active fragment thereof is introduced into a pluripotent cell, preferably a human embryonic stem cell, downstream of the brachyury, FGF4 or SNAI1 promoter such that the expression of the GFP gene product or biologically active fragment thereof is under control of the brachyury, FGF4 or SNAI1 promoter. In some embodiments, the entire coding region of the nucleic acid, which encodes brachyury, FGF4 or SNAI1, is replaced by a nucleic acid encoding GFP or a biologically active fragment thereof. In other embodiments, the nucleic acid encoding GFP or a biologically active fragment thereof is fused in frame with at least a portion of the nucleic acid encoding brachyury, FGF4 or SNAI1, thereby generating a fusion protein. In such embodiments, the fusion protein retains a fluorescent activity similar to GFP.

Fluorescently marked cells, such as the above-described pluripotent cells, are differentiated to mesendoderm cells as described previously above. Because mesendoderm cells express the fluorescent marker gene, whereas non-mesendoderm cells do not, these two cell types can be separated. In some embodiments, cell suspensions comprising a mixture of fluorescently-labeled mesendoderm cells and unlabeled non-mesendoderm cells are sorted using a FACS. Mesendoderm cells are collected separately from non-mesendoderm cells, thereby resulting in the isolation of such cell types. If desired, the isolated cell compositions can be further purified by additional rounds of sorting using the same or different markers that are specific for mesendoderm cells.

In addition to the procedures just described, mesendoderm cells may also be isolated by other techniques for cell isolation. Additionally, mesendoderm cells may also be enriched or isolated by methods of serial subculture in growth conditions which promote the selective survival or selective expansion of the mesendoderm cells.

It will be appreciated that the above-described enrichment, isolation and purification procedures can be used with such cultures at any stage of differentiation.

Using the methods described herein, enriched, isolated and/or purified populations of mesendoderm cells and/or tissues can be produced in vitro from hESC cultures or cell populations which have undergone differentiation for from about 18 hours to about 48 hours. In some embodiments, the cells undergo random differentiation. In a preferred embodiment, however, the cells are directed to differentiate primarily into mesendoderm cells. Some preferred enrichment, isolation and/or purification methods relate to the in vitro production of mesendoderm cells from human embryonic stem cells.

Using the methods described herein, cell populations or cell cultures can be enriched in mesendoderm cell content by at least about 2- to about 1000-fold as compared to untreated or unenriched cell populations or cell cultures. In some embodiments, mesendoderm cells can be enriched by at least about 5- to about 500-fold as compared to untreated or unenriched cell populations or cell cultures. In other embodiments, mesendoderm cells can be enriched from at least about 10- to about 200-fold as compared to untreated or unenriched cell populations or cell cultures. In still other embodiments, mesendoderm cells can be enriched from at least about 20- to about 100-fold as compared to untreated or unenriched cell populations or cell cultures. In yet other embodiments, mesendoderm cells can be enriched from at least about 40- to about 80-fold as compared to untreated or unenriched cell populations or cell cultures. In certain embodiments, mesendoderm cells can be enriched from at least about 2- to about 20-fold as compared to untreated or unenriched cell populations or cell cultures.

Compositions Comprising Mesendoderm Cells

Cell compositions produced by the above-described methods include cell cultures comprising mesendoderm cells and cell populations enriched in mesendoderm cells. For example, cell cultures which comprise mesendoderm cells, wherein at least about 5-90% of the cells in culture are mesendoderm cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to mesendoderm cells. In processes in which isolation of mesendoderm cells is employed, a substantially pure mesendoderm cell population can be recovered.

Some embodiments described herein relate to compositions, such as cell populations and cell cultures, that comprise both pluripotent cells, such as stem cells, and mesendoderm cells. For example, using the methods described herein, compositions comprising mixtures of hESCs and mesendoderm cells can be produced. In some embodiments, compositions comprising at least about 5 mesendoderm cells for about every 95 pluripotent cells are produced. In other embodiments, compositions comprising at least about 95 mesendoderm cells for about every 5 pluripotent cells are produced. Additionally, compositions comprising other ratios of mesendoderm cells to pluripotent cells are contemplated. For example, compositions comprising at least about 1 mesendoderm cell for about every 1,000,000 pluripotent cells, at least about 1 mesendoderm cell for about every 100,000 pluripotent cells, at least about 1 mesendoderm cell for about every 10,000 pluripotent cells, at least about 1 mesendoderm cell for about every 1000 pluripotent cells, at least about 1 mesendoderm cell for about every 500 pluripotent cells, at least about 1 mesendoderm cell for about every 100 pluripotent cells, at least about 1 mesendoderm cell for about every 10 pluripotent cells, at least about 1 mesendoderm cell for about every 5 pluripotent cells, at least about 1 mesendoderm cell for about every 2 pluripotent cells, at least about 2 mesendoderm cells for about every 1 pluripotent cell, at least about 5 mesendoderm cells for about every 1 pluripotent cell, at least about 10 mesendoderm cells for about every 1 pluripotent cell, at least about 20 mesendoderm cells for about every 1 pluripotent cell, at least about 50 mesendoderm cells for about every 1 pluripotent cell, at least about 100 mesendoderm cells for about every 1 pluripotent cell, at least about 1000 mesendoderm cells for about every 1 pluripotent cell, at least about 10,000 mesendoderm cells for about every 1 pluripotent cell, at least about 100,000 mesendoderm cells for about every 1 pluripotent cell and at least about 1,000,000 mesendoderm cells for about every 1 pluripotent cell are contemplated. In some embodiments, the pluripotent cells are human pluripotent stem cells. In certain embodiments, the stem cells are derived from a morula, the inner cell mass of an embryo or the gonadal ridges of an embryo. In certain other embodiments, the pluripotent cells are derived from the gonadal or germ tissues of a multicellular structure that has developed past the embryonic stage.

Some embodiments described herein relate to cell cultures or cell populations comprising from at least about 5% mesendoderm cells to at least about 99% mesendoderm cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are mesendoderm cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are mesendoderm cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human cells, such as human mesendoderm cells, wherein the expression of the brachyury, FGF4 and/or SNAI1 markers is greater than the expression of the OCT4, SOX17, CXCR4, FOXA2, SOX7 and/or SOX1 markers in at least about 5% of the human cells. In other embodiments, the expression of either the brachyury, FGF4 and/or SNAI1 marker is greater than the expression of the OCT4, SOX17, CXCR4, FOXA2, SOX7 and/or SOX1 marker in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells, in at least about 98% of the human cells, in at least about 99% of the human cells or in greater than 99% of the human cells. In embodiments where the cell cultures or cell populations comprise human feeder cells, the above percentages are calculated without respect to the human feeder cells in the cell cultures or cell populations.

Additional embodiments described herein relate to compositions, such as cell cultures or cell populations, comprising human hESCs and human mesendoderm cells, wherein substantial upregulation of the expression of brachyury, FGF4 and/or SNAI1 mRNA occurs in cells of the cell culture or cell population by about 18 hours, by about 19 hours, by about 20 hours, by about 21 hours, by about 22 hours, by about 23 hours, by about 24 hours, by about 25 hours, by about 26 hours, by about 27 hours, by about 28 hours, by about 29 hours, by about 30 hours, by about 31 hours, by about 32 hours, by about 33 hours, by about 34 hours, by about 35 hours, by about 36 hours, by about 37 hours, by about 38 hours, by about 39 hours, by about 40 hours, by about 41 hours, by about 42 hours, by about 43 hours, by about 44 hours, by about 45 hours, by about 46 hours, by about 47 hours, by about 48 hours or by greater than about 48 hours after contacting hESCs in the culture with an appropriate differentiation factor, such as activin A. In such embodiments, substantial upregulation of the expression of brachyury, FGF4 and/or SNAI1 mRNA occurs in at least about 5% of the human cells, at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells, in at least about 98% of the human cells, in at least about 99% of the human cells or in greater than 99% of the human cells. In embodiments where the cell cultures or cell populations comprise human feeder cells, the above percentages are calculated without respect to the human feeder cells in the cell cultures or cell populations.

Using the methods described herein, compositions comprising mesendoderm cells substantially free of other cell types can be produced. In some embodiments described herein, the mesendoderm cell populations or cell cultures produced by the methods described herein are substantially free of cells that significantly express the OCT4, SOX17, CXCR4, FOXA2, SOX7 and/or SOX1 marker genes.

In one embodiment, a description of a mesendoderm cell based on the expression of marker genes is, brachyury high, FGF4 high, SNAI1 high, SOX17 low, CXCR4 low, FOXA2 low, SOX7 low and SOX1 low.

Production of Definitive Endoderm Cells

Processes for differentiating pluripotent cells to produce cell cultures and enriched cell populations comprising definitive endoderm is described briefly below and in detail in U.S. patent Ser. No. 11/021,618, entitled DEFINITIVE ENDODERM, filed Dec. 23, 2004, the disclosure of which is incorporated herein by reference in its entirety. In some of these processes, the pluripotent cells used as starting material are stem cells. In certain processes, definitive endoderm cell cultures and enriched cell populations comprising definitive endoderm cells are produced from embryonic stem cells. A preferred method for deriving definitive endoderm cells utilizes human embryonic stem cells as the starting material for definitive endoderm production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some processes for producing definitive endoderm cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing definitive endoderm permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin subgroups. In some preferred differentiation processes, the growth factor is selected from the group consisting of Nodal, Activin A and Activin B. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred processes, the growth factors are removed about four days after their addition.

Cultures of definitive endoderm cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or without serum replacement. In some embodiments, definitive endoderm cells are grown with serum replacement. In still other processes, definitive endoderm cells are grown in the presence of B27. In such processes, the concentration of B27 supplement can range from about 0.1% v/v to about 20% v/v.

Monitoring the Differentiation of Pluripotent Cells to Definitive Endoderm Cells The progression of the hESC culture to definitive endoderm can be monitored by determining the expression of markers characteristic of definitive endoderm. In some processes, the expression of certain markers is determined by detecting the presence or absence of the marker. Alternatively, the expression of certain markers can determined by measuring the level at which the marker is present in the cells of the cell culture or cell population. In such processes, the measurement of marker expression can be qualitative or quantitative. One method of quantitating the expression of markers that are produced by marker genes is through the use of Q-PCR. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined.

As described further in the Examples below, a reliable marker of definitive endoderm is the SOX17 gene. As such, the definitive endoderm cells produced by the processes described herein express the SOX17 marker gene, thereby producing the SOX17 gene product. Other markers of definitive endoderm are MIXL1, GATA4, HNF3b, GSC, FGF17, VWF, CALCR, FOXQ1, CMKOR1 and CRIP1. Since definitive endoderm cells express the SOX17 marker gene at a level higher than that of the SOX7 marker gene, which is characteristic of primitive and visceral endoderm, in some processes, the expression of both SOX17 and SOX7 is monitored. In other processes, the expression of the both the SOX17 marker gene and the OCT4 marker gene, which is characteristic of hESCs, is monitored. Additionally, because definitive endoderm cells express the SOX17 marker gene at a level higher than that of the AFP, SPARC or Thrombomodulin (TM) marker genes, the expression of these genes can also be monitored.

Another marker of definitive endoderm is the CXCR4 gene. The CXCR4 gene encodes a cell surface chemokine receptor whose ligand is the chemoattractant SDF-1. The principal roles of the CXCR4 receptor-bearing cells in the adult are believed to be the migration of hematopoetic cells to the bone marrow, lymphocyte trafficking and the differentiation of various B cell and macrophage blood cell lineages [Kim, C., and Broxmeyer, H. J. Leukocyte Biol. 65, 6-15 (1999)]. The CXCR4 receptor also functions as a coreceptor for the entry of HIV-1 into T-cells [Feng, Y., et al. Science, 272, 872-877 (1996)]. In an extensive series of studies carried out by [McGrath, K. E. et al. Dev. Biology 213, 442-456 (1999)], the expression of the chemokine receptor CXCR4 and its unique ligand, SDF-1 [Kim, C., and Broxmyer, H., J. Leukocyte Biol. 65, 6-15 (1999)], were delineated during early development and adult life in the mouse. The CXCR4/SDF1 interaction in development became apparent when it was demonstrated that if either gene was disrupted in transgenic mice [Nagasawa et al. Nature, 382, 635-638 (1996)], Ma, Q., et al Immunity, 10, 463-471 (1999)] it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germlayer cells and is expressed on definitive endoderm, mesoderm and extraembryonic mesoderm present at this time. In E7.2-7.8 mouse embryos, CXCR4 and alpha-fetoprotein are mutually exclusive indicating a lack of expression in visceral endoderm [McGrath, K. E. et al. Dev. Biology 213, 442-456 (1999)].

Since definitive endoderm cells produced by differentiating pluripotent cells express the CXCR4 marker gene, expression of CXCR4 can be monitored in order to track the production of definitive endoderm cells. Additionally, definitive endoderm cells produced by the methods described herein express other markers of definitive endoderm including, but not limited to, SOX17, MIXL1, GATA4, HNF3b, GSC, FGF17, VWF, CALCR, FOXQ1, CMKOR1 and CRIP1. Since definitive endoderm cells express the CXCR4 marker gene at a level higher than that of the SOX7 marker gene, the expression of both CXCR4 and SOX7 can be monitored. In other processes, expression of the both the CXCR4 marker gene and the OCT4 marker gene, is monitored. Additionally, because definitive endoderm cells express the CXCR4 marker gene at a level higher than that of the AFP, SPARC or Thrombomodulin (TM) marker genes, the expression of these genes can also be monitored.

It will be appreciated that expression of CXCR4 in endodermal cells does not preclude the expression of SOX17. As such, definitive endoderm cells produced by the processes described herein will substantially express SOX17 and CXCR4 but will not substantially express AFP, TM, SPARC or PDX1.

Enrichment, Isolation and/or Purification of Definitive Endoderm Cells

Definitive endoderm cells produced by any of the above-described processes can be enriched, isolated and/or purified by using an affinity tag that is specific for such cells. Examples of affinity tags specific for definitive endoderm cells are antibodies, ligands or other binding agents that are specific to a marker molecule, such as a polypeptide, that is present on the cell surface of definitive endoderm cells but which is not substantially present on other cell types that would be found in a cell culture produced by the methods described herein. In some processes, an antibody which binds to CXCR4 is used as an affinity tag for the enrichment, isolation or purification of definitive endoderm cells. In other processes, the chemokine SDF-1 or other molecules based on SDF-1 can also be used as affinity tags. Such molecules include, but not limited to, SDF-1 fragments, SDF-1 fusions or SDF-1 mimetics.

Methods for making antibodies and using them for cell isolation are known in the art and such methods can be implemented for use with the antibodies and definitive endoderm cells described herein. In one process, an antibody which binds to CXCR4 is attached to a magnetic bead and then allowed to bind to definitive endoderm cells in a cell culture which has been enzymatically treated to reduce intercellular and substrate adhesion. The cell/antibody/bead complexes are then exposed to a movable magnetic field which is used to separate bead-bound definitive endoderm cells from unbound cells. Once the definitive endoderm cells are physically separated from other cells in culture, the antibody binding is disrupted and the cells are replated in appropriate tissue culture medium.

Additional methods for obtaining enriched, isolated or purified definitive endoderm cell cultures or populations can also be used. For example, in some embodiments, the CXCR4 antibody is incubated with a definitive endoderm-containing cell culture that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). CXCR4-positive cells are collected separately from CXCR4-negative cells, thereby resulting in the isolation of such cell types. If desired, the isolated cell compositions can be further purified by using an alternate affinity-based method or by additional rounds of sorting using the same or different markers that are specific for definitive endoderm.

In still other processes, definitive endoderm cells are enriched, isolated and/or purified using a ligand or other molecule that binds to CXCR4. In some processes, the molecule is SDF-1 or a fragment, fusion or mimetic thereof.

In preferred processes, definitive endoderm cells are enriched, isolated and/or purified from other non-definitive endoderm cells after the stem cell cultures are induced to differentiate towards the definitive endoderm lineage. It will be appreciated that the above-described enrichment, isolation and purification procedures can be used with such cultures at any stage of differentiation.

In addition to the procedures just described, definitive endoderm cells may also be isolated by other techniques for cell isolation. Additionally, definitive endoderm cells may also be enriched or isolated by methods of serial subculture in growth conditions which promote the selective survival or selective expansion of the definitive endoderm cells.

Using the methods described herein, enriched, isolated and/or purified populations of definitive endoderm cells and or tissues can be produced in vitro from pluripotent cell cultures or cell populations, such as stem cell cultures or populations, which have undergone at least some differentiation. In some methods, the cells undergo random differentiation. In a preferred method, however, the cells are directed to differentiate primarily into definitive endoderm. Some preferred enrichment, isolation and/or purification methods relate to the in vitro production of definitive endoderm from human embryonic stem cells. Using the methods described herein, cell populations or cell cultures can be enriched in definitive endoderm content by at least about 2- to about 1000-fold as compared to untreated cell populations or cell cultures.

Compositions Comprising Definitive Endoderm Cells

Cell compositions produced by the above-described methods include cell cultures comprising definitive endoderm and cell populations enriched in definitive endoderm. For example, cell cultures which comprise definitive endoderm cells, wherein at least about 50-99% of the cells in the cell culture or the cell population are definitive endoderm cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99% or greater than about 99% conversion of pluripotent cells to definitive endoderm. In processes in which isolation of definitive endoderm cells is employed, for example, by using an affinity reagent that binds to the CXCR4 receptor, a substantially pure definitive endoderm cell population can be recovered. In embodiments where the cell cultures or cell populations comprise human feeder cells, the above percentages are calculated without respect to the human feeder cells in the cell cultures or cell populations.

Identification of Factors Capable of Promoting the Differentiation of Preprimitive Streak and/or Mesendoderm Certain screening methods described herein relate to methods for identifying at least one differentiation factor that is capable of promoting the differentiation of preprimitive streak and/or mesendoderm cells. In some embodiments of these methods, a cell population comprising preprimitive streak and/or mesendoderm cells, such as human preprimitive streak and/or mesendoderm cells, is obtained. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the definitive endoderm cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of definitive endoderm cells.

Some embodiments of the screening methods described herein utilize cell populations or cell cultures which comprise human preprimitive streak and/or mesendoderm cells. For example, the cell population can be a substantially purified population of human preprimitive streak and/or mesendoderm cells. Alternatively, the cell population can be an enriched population of human preprimitive streak and/or mesendoderm cells, wherein at least about 90%, at least about 91%, at least about 92%, at least about 93%, at least about 94%, at least about 95%, at least about 96%, at least about 97%, at least about 98%, at least about 99% or greater than at least about 99% of the human cells in the cell population are human preprimitive streak and/or mesendoderm cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are human preprimitive streak and/or mesendoderm cells. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are human preprimitive streak and/or mesendoderm cells.

In embodiments of the screening methods described herein, the cell population is contacted or otherwise provided with a candidate (test) differentiation factor. The candidate differentiation factor can comprise any molecule that may have the potential to promote the differentiation of human preprimitive streak and/or mesendoderm cells. In some embodiments described herein, the candidate differentiation factor comprises a molecule that is known to be a differentiation factor for one or more types of cells. In alternate embodiments, the candidate differentiation factor comprises a molecule that in not known to promote cell differentiation. In preferred embodiments, the candidate differentiation factor comprises molecule that is not known to promote the differentiation of human preprimitive streak and/or mesendoderm cells.

In some embodiments of the screening methods described herein, the candidate differentiation factor comprises a small molecule. In preferred embodiments, a small molecule is a molecule having a molecular mass of about 10,000 amu or less. In some embodiments the small molecule is a retinoid, such as retinoic acid.

In other embodiments described herein, the candidate differentiation factor comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors. In some preferred embodiments, the candidate differentiation factors comprises one or more growth factors selected from the group consisting of FGF10, FGF4, FGF2 and Wnt3B.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone mophogenetic protein 2, Bone mophogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin D3, Epidermal growth factor (EGF), Brain-derived neurotrophic factor, Leukemia inhibitory factor, Thyroid hormone, Basic fibroblast growth factor (bFGF), aFGF, FGF-4, FGF-6, Keratinocyte growth factor (KGF), Platelet-derived growth factor (PDGF), Platelet-derived growth factor-BB, beta nerve growth factor, activin A, Transforming growth factor beta 1 (TGF-β1), Interferon-α, Interferon-β, Interferon-γ, Tumor necrosis factor-α, Tumor necrosis factor-β, Burst promoting activity (BPA), Erythroid promoting activity (EPA), PGE2, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine tyrosine, neuropeptide tyrosine, insulin, glucagon, placental lactogen, relaxin, angiotensin II, calctriol, atrial natriuretic peptide, and melatonin. thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, β-mercaptoethanol, Retinoic acid, Butylated hydroxyanisole, 5-aza-cytidine, Amphotericin B, Ascorbic acid, Ascrorbate, isobutylxanthine, indomethacin, β-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 µg/ml. In still other embodiments, the concentration of the candidate differentiation factor in the medium surrounding the cells ranges from about 100 ng/ml to about 10 µg/ml. In preferred embodiments, the concentration of the candidate differentiation factor in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

In certain embodiments of the screening methods described herein, the cell population is provided with a candidate differentiation factor which comprises any molecule other than foregut differentiation factor. For example, in some embodiments, the cell population is provided with a candidate differentiation factor which comprises any molecule other than a retinoid, a member of the TGFβ superfamily of growth factors, FGF10 or FGF4. In some embodiments, the cell population is provided with a candidate differentiation factor which comprises any molecule other than retinoic acid.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In certain embodiments of the screening methods described herein, the marker having its expression is determined at the first and second time points is a marker that is associated with the differentiation of human preprimitive streak cells and/or mesendoderm cells to cells which are the precursors of cells which make up tissues and/or organs that are derived from the gut tube. In some embodiments, the tissues and/or organs that are derived from the gut tube comprise terminally differentiated cells. In some embodiments, the marker is indicative of pancreatic cells or pancreatic precursor cells. In preferred embodiments, the marker is pancreatic-duodenal homeobox factor-1 (PDX1). In other embodiments, the marker is homeobox A13 (HOXA13) or homeobox C6 (HOXC6). Additionally, in other embodiments, the marker is indicative of liver cells or liver precursor cells. In certain preferred embodiments, the marker is albumin, hepatocyte specific antigen (HSA) or prospero-related homeobox 1 (PROX1). In other embodiments, the marker is indicative of lung or lung precursor cells. In some preferred embodiments, the marker is thyroid transcription factor 1 (TITF1). In yet other embodiments, the marker is indicative of intestinal or intestinal precursor cells. In additional preferred embodiments, the marker is villin or caudal type homeobox transcription factor 2 (CDX2). In still other embodiments, the marker is indicative of stomach or stomach precursor cells. In additional preferred embodiments, the marker is VCAM1, VWF or CXCR4. In other embodiments, the marker is indicative of thyroid or thyroid precursor cells. In such embodiments, the marker is TITF1. In still other embodiments, the marker is indicative of thymus or thymus precursor cells.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours or at least about 240 hours.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the definitive endoderm cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

In some embodiments of the screening methods described herein, after providing the cell population with a candidate differentiation factor, the human preprimitive streak and/or mesendoderm cells differentiate into one or more cell types of the definitive endoderm lineage. In some embodiments, after providing the cell population with a candidate differentiation factor, the human preprimitive streak and/or mesendoderm cells differentiate into cells that are derived from the gut tube. Such cells include, but are not limited to, cells of the pancreas, liver, lungs, stomach, intestine, thyroid, thymus, pharynx, gallbladder and urinary bladder as well as precursors of such cells. Additionally, these cells can further develop into higher order structures such as tissues and/or organs.

In other embodiments of the screening methods described herein, after providing the cell population with a candidate differentiation factor, the human preprimitive streak and/or mesendoderm cells differentiate into one or more cell types of the mesoderm lineage. In some embodiments, after providing the cell population with a candidate differentiation factor, the human preprimitive streak and/or mesendoderm cells differentiate into cells which include, but are not limited to, blood cells, cells of the cardiovascular system, skeletal tissues and other structural and connective tissues as well as precursors of each of the aforementioned cell types. Additionally, these cells can further develop into higher order structures such as tissues and/or organs.

Methods of Increasing the Expression of the FGF8 Gene Product

Some embodiments of the methods described herein relate to a method of increasing the expression of the FGF8 gene product in a human embryonic stem cell in vitro. Such methods comprise the step of obtaining said hESC in a medium comprising less than about 2% (v/v) serum. For example, the medium can comprise serum at a concentration of about 0% (v/v), of about 0.05% (v/v), about 0.1% (v/v), about 0.2% (v/v), about 0.3% (v/v), about 0.4% (v/v), about 0.5% (v/v), about 0.6% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 1.1% (v/v), about 1.2% (v/v), about 1.3% (v/v), about 1.4% (v/v), about 1.5% (v/v), about 1.6% (v/v), about 1.7% (v/v), about 1.8% (v/v) or about 1.9% (v/v). In some embodiments, the medium does not comprise serum replacement. The hESCs are contacted with a differentiation factor in an amount sufficient to increase expression of the FGF8 gene product. In some embodiments, the differentiation factor is at least one growth factor of the TGFβ superfamily. In preferred embodiments, the growth factor of the TGFβ superfamily is activin A. The concentration of differentiation factor that is used to contact the hESCs ranges from about 1 ng/ml to about 1 mg/ml. For example, the hESCs can be contacted with a differentiation factor at a concentration of 1 ng/ml, about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

Methods of Increasing the Expression of the Brachyury, FGF4 and/or SNAI1 Gene Product Other embodiments of the methods described herein relate to a method of increasing the expression of the brachyury, FGF4 and/or SNAI1 gene product in a human embryonic stem cell in vitro. Such methods comprise the step of obtaining said hESC in a medium comprising less than about 2% (v/v) serum. For example, the medium can comprise serum at a concentration of about 0% (v/v), of about 0.05% (v/v), about 0.1% (v/v), about 0.2% (v/v), about 0.3% (v/v), about 0.4% (v/v), about 0.5% (v/v), about 0.6% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 1.1% (v/v), about 1.2% (v/v), about 1.3% (v/v), about 1.4% (v/v), about 1.5% (v/v), about 1.6% (v/v), about 1.7% (v/v), about 1.8% (v/v) or about 1.9% (v/v). In some embodiments, the medium does not comprise serum replacement. The hESCs are contacted with a differentiation factor in an amount sufficient to increase expression of the brachyury, FGF4 and/or SNAI1 gene product. In some embodiments, the differentiation factor is at least one growth factor of the TGFβ superfamily. In preferred embodiments, the growth factor of the TGFβ superfamily is activin A. The concentration of differentiation factor that is used to contact the hESCs ranges from about 1 ng/ml to about 1 mg/ml. For example, the hESCs can be contacted with a differentiation factor at a concentration of 1 ng/ml, about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000

Temporal Expression of Gene Products in Cell Cultures

Further embodiments of the present invention relate to cell cultures having certain temporal patterns of gene expression. In some embodiments, the cell culture comprise human embryonic stem cells (hESCs) and a medium comprising less than about 2% (v/v) serum. For example, the medium can comprise serum at a concentration of about 0% (v/v), of about 0.05% (v/v), about 0.1% (v/v), about 0.2% (v/v), about 0.3% (v/v), about 0.4% (v/v), about 0.5% (v/v), about 0.6% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 1.1% (v/v), about 1.2% (v/v), about 1.3% (v/v), about 1.4% (v/v), about 1.5% (v/v), about 1.6% (v/v), about 1.7% (v/v), about 1.8% (v/v) or about 1.9% (v/v). In some embodiments, the medium does not comprise serum replacement. In some embodiments, the medium is low serum RPMI.

In some embodiments described herein, hESCs in culture begin differentiating at a reference time point. The reference time point is the point at which a differentiation factor is provided to the cells. In some embodiments, the differentiation factor is at least one growth factor of the TGFβ superfamily. In preferred embodiments, the growth factor of the TGFβ superfamily is activin A. The concentration of differentiation factor that is provided to the hESCs ranges from about 1 ng/ml to about 1 mg/ml. For example, the hESCs can be contacted with a differentiation factor at a concentration of 1 ng/ml, about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

After providing the differentiation factor to the hESCs, the expression of FGF8 mRNA is substantially upregulated as compared to baseline FGF8 mRNA expression in the hESCs. Baseline FGF8 expression in hESCs is the expression of FGF8 gene product, such as mRNA, present in an hESC cell culture that is maintained in it undifferentiated state. In some embodiments, FGF8 mRNA expression is substantially upregulated by about 6 hours from the reference time point. In further embodiments described herein, expression of FGF8 mRNA is downregulated after about 24 hours from the reference time point. In other embodiments, peak expression of FGF8 mRNA is reached at a time between about 6 hours and about 24 hours from the reference time point. In other embodiments, peak expression of FGF8 may be reached at a time less than about 6 hours from the reference time point.

Other embodiments described herein relate to cell cultures exhibiting increased nuclear localization of the β-catenin polypeptide. In such embodiments, the β-catenin polypeptide begins to become localized to the cell nucleus by about 17 hours from the reference time point. In some embodiments, the β-catenin polypeptide begins to become localized to the cell nucleus by less than about 17 hours from the reference time point. In still other embodiments, the β-catenin polypeptide becomes predominantly localized to the cell nucleus by about 17 hours from the reference time point.

Still other embodiments of the cell cultures described herein relate to cell cultures having increased expression of brachyury mRNA. In such cell cultures, brachyury mRNA expression is substantially upregulated by about 24 hours from the reference time point. In some embodiments, brachyury mRNA expression is substantially upregulated prior to about 24 hours from the reference time point. In some embodiments, expression of brachyury mRNA is substantially downregulated by about 48 hours from the reference time point. In certain embodiments, peak expression of brachyury mRNA is reached at a time between about 12 hours and about 48 hours from the reference time point. In preferred embodiments, the brachyury mRNA in not substantially expressed by about 72 hours from the reference time point. In other preferred embodiments, brachyury mRNA is substantially upregulated by about 24 hours from the reference time point and is not substantially expressed by about 72 hours from the reference time point.

Still further embodiments of the cell cultures described herein relate to cell cultures having increased expression of FGF4 mRNA. In such cell cultures, FGF4 mRNA expression is substantially upregulated by about 24 hours from the reference time point. In some embodiments, FGF4 mRNA expression is substantially upregulated prior to about 24 hours from the reference time point. In some embodiments, expression of FGF4 mRNA is substantially downregulated by about 48 hours from the reference time point. In certain embodiments, peak expression of FGF4 mRNA is reached at a time between about 12 hours and about 48 hours from the reference time point. In preferred embodiments, the FGF4 mRNA in not substantially expressed by about 72 hours from the reference time point. In other preferred embodiments, FGF4 mRNA is substantially upregulated by about 24 hours from the reference time point and is not substantially expressed by about 72 hours from the reference time point.

Preferred embodiments of the cell cultures described herein relate to cell cultures having increased expression of brachyury and FGF4 mRNA. In such cell cultures, brachyury and FGF4 mRNA expression is substantially upregulated by about 24 hours from the reference time point. In some embodiments, brachyury and FGF4 mRNA expression is substantially upregulated prior to about 24 hours from the reference time point. In some embodiments, expression of brachyury and FGF4 mRNA is substantially downregulated by about 48 hours from the reference time point. In certain embodiments, peak expression of brachyury and FGF4 mRNA is reached at a time between about 12 hours and about 48 hours from the reference time point. In preferred embodiments, the brachyury and FGF4 mRNA in not substantially expressed by about 72 hours from the reference time point. In other preferred embodiments, brachyury and FGF4 mRNA is substantially upregulated by about 24 hours from the reference time point and is not substantially expressed by about 72 hours from the reference time point.

Additional embodiments of the cell cultures described herein relate to cell cultures having increased expression of SNAI1 mRNA. In such cell cultures, SNAI1 mRNA expression is substantially upregulated by about 24 hours from the reference time point. In some embodiments, SNAI1 mRNA expression is substantially upregulated prior to about 24 hours from the reference time point. In some embodiments, expression of SNAI1 mRNA is downregulated by about 48 hours from the reference time point. In certain embodiments, peak expression of SNAI1 mRNA is reached at a time between about 12 hours and about 48 hours from the reference time point.

Embodiments of the cell cultures described herein also relate to cell cultures having a specific temporal expression of the E-cadherin (ECAD) gene product. In such embodiments, expression of E-cadherin mRNA begins to be downregulated by about 12 hours from the reference time point. In other embodiments, expression of E-cadherin mRNA can be downregulated by about less than 12 hours from the reference time point. In preferred embodiments, expression of E-cadherin mRNA is substantially downregulated by about 48 hours from the reference time point.

Further embodiments described herein relate to cell cultures that express the SOX17 and/or FOXA2 marker. In some embodiments, expression of SOX17 mRNA is substantially upregulated by about 48 hours from the reference time point. In other embodiments, expression of FOXA2 mRNA is substantially upregulated by about 96 hours from the reference time point.

Some embodiments described herein relate to cell cultures that comprise cells having certain specified patterns of gene expression. In such embodiments, the cell cultures comprise hESCs, a differentiation factor, such as a differentiation factor of the TGFβ superfamily, and a medium comprising less than about 2% (v/v) serum. In alternative embodiments, the medium comprises greater than 2% (v/v) serum. In some embodiments, the medium lacks serum replacement.

In some embodiments, at the time the cell culture is provided with the differentiation factor, the cell culture comprises all or predominantly all hESCs. During the course of differentiation, at least a portion of the hESCs differentiate into other cell types as indicated by the expression of the products (mRNA and/or polypeptides) of certain marker genes.

In some embodiments of the cell cultures described herein, the expression of a first set of marker genes is upregulated prior to the upregulation of a second and/or a third set of marker genes. In some embodiments, each set of marker genes can include one or more marker genes. Upregulation of gene expression can range from slight to substantial. For example, expression of a marker gene can be upregulated by at least about 10% as compared to the expression of the same marker gene in undifferentiated hESCs. In other embodiments, expression of a marker gene can be upregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be upregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In other embodiments of the cell cultures described herein, the expression of a first set of marker genes is downregulated regulated prior to the upregulation of a second and/or a third set of marker genes. In such embodiments, the each set of marker genes can include one or more marker genes. As with upregulation of gene expression, downregulation can range from slight to substantial. For example, expression of a marker gene can be downregulated by at least about 10% as compared to the expression of the same marker gene in undifferentiated hESCs. In other embodiments, expression of a marker gene can be downregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be downregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In still other embodiments of the cell cultures described herein, the expression of a first set of marker genes is upregulated prior to or at about the same time as the peak expression of a second set and/or a third set of marker genes. In such embodiments, each set of marker genes can comprise one or more marker genes. In other embodiments, the expression of a first set of marker genes is downregulated prior to or at about the same time as the peak expression of a second set and/or a third set of marker genes. As described above, in such embodiments, each set of marker genes can comprise one or more marker genes. Furthermore, in the above-described embodiments, both upregulation and downregulation of gene expression can range from slight to substantial. For example, expression of a marker gene can be upregulated or downregulated by at least about 10% as compared to the expression of the same marker gene in undifferentiated hESCs. In other embodiments, expression of a marker gene can be upregulated or downregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be upregulated or downregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In some embodiments described herein, in at least some cells of the cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4. In other embodiments, in at least some cell of the cell culture, expression of a marker gene selected from the group consisting of FGF8, Nodal, HEG, HEY1, GATA2, BIK and ID1 is upregulated prior to peak expression of a marker gene selected from the group consisting of brachyury, FGF4, SNAI1, Wnt3, MIXL1, DKK4, NETO1, T, DACT1, FLJ22662, SLIT2, GAD1 and GRM4. In still other embodiments, in at least some cell of the cell culture, expression of a marker gene selected from the group consisting of HEY1, GATA2, BIK and ID1 is downregulated prior to or at about the same time as peak expression of a marker gene selected from the group consisting of brachyury, FGF4, SNAI1, Wnt3, MIXL1, DKK4, NETO1, T, DACT1, FLJ22662, SLIT2, GAD1 and GRM4. In further embodiments, in at least some cell of the cell culture, expression of a marker gene selected from the group consisting of FGF8, Nodal, HEG, HEY1, GATA2, BIK and ID1 is upregulated prior to upregulation of expression of a marker gene selected from the group consisting of SOX17, FOXA2, CXCR4 and MIXL1. In still other embodiments, in at least some cell of the cell culture, expression of a marker gene selected from the group consisting of brachyury, FGF4, SNAI1, Wnt3, MIXL1, DKK4, NETO1, T, DACT1, FLJ22662, SLIT2, GAD1 and GRM4 is upregulated prior to or at about the same time as upregulation of expression of a marker gene selected from the group consisting of SOX17, FOXA2, CXCR4 and MIXL1. In yet other embodiments, in at least some cell of the cell culture, peak expression of a marker gene selected from the group consisting of brachyury, FGF4, SNAI1, Wnt3, MIXL1, DKK4, NETO1, T, DACT1, FLJ22662, SLIT2, GAD1 and GRM4 is reached prior to or at about the same time as upregulation of expression of a marker gene selected from the group consisting of SOX17, FOXA2, CXCR4 and MIXL1. In additional embodiments, in at least some cell of the cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

Some of the cell cultures having one or more of the temporal gene expression patterns described above include a medium comprising less than about 2% (v/v) serum. In some embodiments, the medium does not include serum. In other embodiments, the medium lacks serum replacement. Some of the media used in the cell cultures described herein include serum at a concentration of less than about 1.9% (v/v), less than about 1.8% (v/v), less than about 1.7% (v/v), less than about 1.6% (v/v), less than about 1.5% (v/v), less than about 1.4% (v/v), less than about 1.3% (v/v), less than about 1.2% (v/v), less than about 1.1% (v/v), less than about 1% (v/v), less than about 0.9% (v/v), less than about 0.8% (v/v), less than about 0.7% (v/v), less than about 0.6% (v/v), less than about 0.5% (v/v), less than about 0.4% (v/v), less than about 0.3% (v/v), less than about 0.2% (v/v), less than about 0.1% (v/v) or less than about 0.05% (v/v).

Some of the cell cultures having one or more of the temporal gene expression patterns described above comprise at least one differentiation factor of the TGFβ superfamily. In some embodiments, the growth factor is nodal, activin A and/or activin B. In preferred embodiments, the differentiation factor is activin A. In more preferred embodiments, the activin A is present in the medium at a concentration of about 100 ng/ml.

It will be appreciated, however, that the differentiation factor of the TGFβ superfamily can be supplied to the cell culture at concentrations ranging from about 1 ng/ml to about 1 mg/ml. In some embodiments, the differentiation factor of the TGFβ superfamily is supplied to the cell culture at about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

Methods of differentiating hESCs so as to produce cells having certain temporal marker gene expression patterns are also contemplated herein. For example, some embodiments relate to a method of differentiating human embryonic stem cells (hESCs), by contacting the hESCs with a medium comprising less that about 2% serum, providing the hESCs with a differentiation factor of the TGFβ superfamily, and then permitting differentiation of the hESCs to occur.

In some embodiments of the above-described methods of differentiating hESCs, the expression of a first set of marker genes is upregulated prior to the upregulation of a second and/or a third set of marker genes. In some embodiments, each set of marker genes can include one or more marker genes. Upregulation of gene expression can range from slight to substantial. For example, expression of a marker gene can be upregulated by at least about 10% as compared to the expression of the same marker gene in undifferentiated hESCs. In other embodiments, expression of a marker gene can be upregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be upregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In other embodiments of methods of differentiating hESCs described herein, the expression of a first set of marker genes is downregulated regulated prior to the upregulation of a second and/or a third set of marker genes. In such embodiments, the each set of marker genes can include one or more marker genes. As with upregulation of gene expression, downregulation can range from slight to substantial. For example, expression of a marker gene can be downregulated by at least about 10% as compared to the expression of the same marker gene in undifferentiated hESCs. In other embodiments, expression of a marker gene can be downregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be downregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In still other embodiments of methods of differentiating hESCs described herein, the expression of a first set of marker genes is upregulated prior to or at about the same time as the peak expression of a second set and/or a third set of marker genes. In such embodiments, each set of marker genes can comprise one or more marker genes. In other embodiments, the expression of a first set of marker genes is downregulated prior to or at about the same time as the peak expression of a second set and/or a third set of marker genes. As described above, in such embodiments, each set of marker genes can comprise one or more marker genes. Furthermore, in the above-described embodiments, both upregulation and downregulation of gene expression can range from slight to substantial. For example, expression of a marker gene can be upregulated or downregulated by at least about 10% as compared to the expression of the same marker gene in undifferentiated hESCs. In other embodiments, expression of a marker gene can be upregulated or downregulated by at least about 20%, at least about 30%, at least about 40%, at least about 50%, at least about 60%, at least about 70%, at least about 80%, at least about 90% or greater than at least about 90% as compared to the expression of the same marker gene in undifferentiated hESCs. In still other embodiments, the marker gene expression can be upregulated or downregulated by at least 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold or greater than at least about 100-fold as compared to the expression of the same marker gene in undifferentiated hESCs.

In some embodiments described herein, in at least some cells of the cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4. In other embodiments, in at least some cell of the cell culture, expression of a marker gene selected from the group consisting of FGF8, Nodal, HEG, HEY1, GATA2, BIK and ID1 is upregulated prior to peak expression of a marker gene selected from the group consisting of brachyury, FGF4, SNAI1, Wnt3, MIXL1, DKK4, NETO1, T, DACT1, FLJ22662, SLIT2, GAD1 and GRM4. In still other embodiments, in at least some cell of the cell culture, expression of a marker gene selected from the group consisting of HEY1, GATA2, BIK and ID1 is downregulated prior to or at about the same time as peak expression of a marker gene selected from the group consisting of brachyury, FGF4, SNAI1, Wnt3, MIXL1, DKK4, NETO1, T, DACT1, FLJ22662, SLIT2, GAD1 and GRM4. In further embodiments, in at least some cell of the cell culture, expression of a marker gene selected from the group consisting of FGF8, Nodal, HEG, HEY1, GATA2, BIK and ID1 is upregulated prior to upregulation of expression of a marker gene selected from the group consisting of SOX17, FOXA2, CXCR4 and MIXL1. In still other embodiments, in at least some cell of the cell culture, expression of a marker gene selected from the group consisting of brachyury, FGF4, SNAI1, Wnt3, MIXL1, DKK4, NETO1, T, DACT1, FLJ22662, SLIT2, GAD1 and GRM4 is upregulated prior to or at about the same time as upregulation of expression of a marker gene selected from the group consisting of SOX17, FOXA2, CXCR4 and MIXL1. In yet other embodiments, in at least some cell of the cell culture, peak expression of a marker gene selected from the group consisting of brachyury, FGF4, SNAI1, Wnt3, MIXL1, DKK4, NETO1, T, DACT1, FLJ22662, SLIT2, GAD1 and GRM4 is reached prior to or at about the same time as upregulation of expression of a marker gene selected from the group consisting of SOX17, FOXA2, CXCR4 and MIXL1. In additional embodiments, in at least some cell of the cell culture, expression of a marker gene selected from the group consisting of FGF8, Nodal, HEG, HEY1, GATA2, BIK and ID1 is upregulated prior to upregulation of expression of a marker gene selected from the group consisting of brachyury, FGF4, SNAI1, Wnt3, MIXL1, DKK4, NETO1, T, DACT1, FLJ22662, SLIT2, GAD1 and GRM4.

In some embodiments of the differentiation methods described herein, cells of the cell culture are contacted or otherwise provided with a medium that comprises less than about 2% (v/v) serum. In some embodiment the medium does not include serum. In other embodiments, the medium lacks serum replacement. Some of the media used in the methods described herein include serum at a concentration of less than about 1.9% (v/v), less than about 1.8% (v/v), less than about 1.7% (v/v), less than about 1.6% (v/v), less than about 1.5% (v/v), less than about 1.4% (v/v), less than about 1.3% (v/v), less than about 1.2% (v/v), less than about 1.1% (v/v), less than about 1% (v/v), less than about 0.9% (v/v), less than about 0.8% (v/v), less than about 0.7% (v/v), less than about 0.6% (v/v), less than about 0.5% (v/v), less than about 0.4% (v/v), less than about 0.3% (v/v), less than about 0.2% (v/v), less than about 0.1% (v/v) or less than about 0.05% (v/v).

Some of the methods for differentiating hESCs to produce the above-described temporal patterns of gene expression include providing the cells in culture, such as hESCs, with at least one differentiation factor of the TGFβ superfamily. In some embodiments, the growth factor is nodal, activin A and/or activin B. In preferred embodiments, the differentiation factor is activin A. In more preferred embodiments, the activin A is present in the medium at a concentration of about 100 ng/ml.

It will be appreciated, however, that the differentiation factor of the TGFβ superfamily can be supplied to the cell culture at concentrations ranging from about 1 ng/ml to about 1 mg/ml. In some embodiments, the differentiation factor of the TGFβ superfamily is supplied to the cell culture at about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

Having generally described this invention, a further understanding can be obtained by reference to certain specific examples which are provided herein for purposes of illustration only, and are not intended to be limiting.

EXAMPLES

Many of the examples below describe the use of pluripotent human cells. Methods of producing pluripotent human cells are well known in the art and have been described numerous scientific publications, including U.S. Pat. Nos. 5,453,357, 5,670,372, 5,690,926, 6,090,622, 6,200,806 and 6,251,671 as well as U.S. Patent Application Publication No. 2004/0229350, the disclosures of which are incorporated herein by reference in their entireties.

Example 1

Human ES Cells

For our studies of early development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, ITS supplement). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extra-embryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Definitive Endoderm Cells

Copending and co-owned U.S. patent application Ser. No. 11/021,618, entitled DEFINITIVE ENDODERM, filed Dec. 23, 2004, describes cell cultures and enriched cell populations comprising human definitive endoderm cells. Also described therein are methods of producing definitive endoderm from hESCs by differentiation in the presence of a differentiation factor as well as methods for enriching, isolating and/or purifying these definitive endoderm cells from mixed cell cultures and/or cell populations. Further described therein are markers that are useful for the identification and/or detection of definitive endoderm cells as well as a marker useful in the purification of such cells. The disclosed of U.S. patent application Ser. No. 11/021,618, entitled DEFINITIVE ENDODERM, filed Dec. 23, 2004, is incorporated herein by reference in its entirety.

This Example, which describes useful marker for the detection and/or identification of definitive endoderm cells, it reproduced from the aforementioned copending patent application.

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/ml recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/ml of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis Immunopurification was achieved for hESCs using SSEA4 antigen (R&D Systems, cat# FAB1435P) and for definitive endoderm using CXCR4 (R&D Systems, cat# FAB170P). Cells were dissociated using trypsin/EDTA (Invitrogen, cat#25300-054), washed in phosphate buffered saline (PBS) containing 2% human serum and resuspended in 100% human serum on ice for 10 minutes to block non-specific binding. Staining was carried out for 30 minutes on ice by adding 200 µl of phycoerythrin-conjugated antibody to $5 \times 10^6$ cells in 800 µl human serum. Cells were washed twice with 8 ml of PBS buffer and resuspended in 1 ml of the same. FACS isolation was carried out by the core facility of The Scripps Research Institute using a FACS Vantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm. Genes that exhibited a robust upward change in expression level over that found in hESCs were selected as new candidate markers that are highly characteristic of definitive endoderm. Select genes were assayed by Q-PCR, as described above, to verify the gene expression changes found on the gene chip and also to investigate the expression pattern of these genes during a time course of hESC differentiation.

FIGS. 2A-2M show the gene expression results for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified hESCs. A comparison of FIGS. 2C and 2G-2M demonstrates that the six marker genes, FGF17, VWF, CALCR, FOXQ1, CMKOR1 and CRIP1, exhibited an expression pattern that is almost identical to each other and which is also identical to the pattern of expression of CXCR4 and the ratio of SOX17/SOX7. As described previously, SOX17 was expressed in both the definitive endoderm as well as in the SOX7-expressing extra-embryonic endoderm. Since SOX7 was not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are markers of definitive endoderm and that they are not significantly expressed in extra-embryonic endoderm cells.

It will be appreciated that the Q-PCR results described herein can be further confirmed by ICC.

Example 4

Temporal Sequence of Gene Expression in Definitive Endoderm Precursor Cells

To assess the dynamics of gene expression that occur during differentiation to definitive endoderm, the expression of numerous genes was monitored in differentiating cell cultures at various time points during two different four day differentiation protocols.

Specifically, hESCs were cultured in the absence of FBS for the first 24 hours, in 0.2% (v/v) FBS for the second 24 hours and in 2% (v/v) FBS on days 3 and 4, with continuous exposure to either 100 ng/ml of activin A to induce differentiation to definitive endoderm or 100 ng/ml of BMP4 and 2.5 µM of the FGFR1 inhibitor, SU5402, to induce differentiation to a mixed cell population of trophectoderm (TE) and primitive endoderm (PrE). The dynamics of gene expression in such cultures were determined by measuring gene expression at various time points during the differentiation procedure. In particular, gene expression was determined by Q-PCR at the time of addition of the differentiation factors as well as 6 hours, 12 hours, 24 hours, 48 hours, 72 hours and 96 hours after the addition of these factors. Gene expression profiles over this time course for several different marker genes are displayed in FIGS. 3A-L.

Figure 3A:
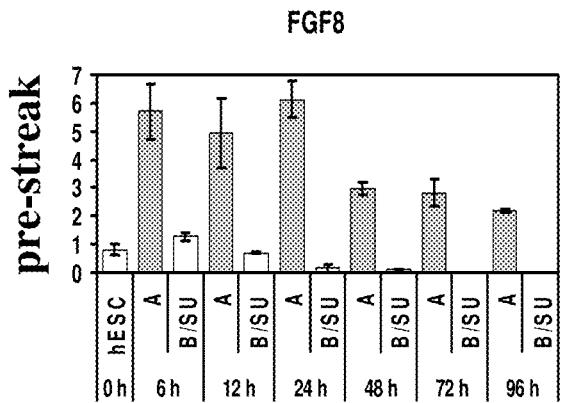
FIGS. 3A-3L are bar charts showing the expression patterns of certain marker genes expressed in (A) preprimitive streak cells, (B-D) primitive streak (mesendoderm) cells, (E-F) mesendoderm and definitive endoderm cells, (G) definitive endoderm cells, and (H-L) trophectoderm and primitive endoderm cells. Marker expression was determined by Q-PCR during the course of differentiation at 0, 6, 12, 24, 48, 72 and 96 hours after addition of 100 ng/ml activin A (indicated by "A") or a combination of 100 ng/ml of BMP4 and 2.5 µM SU5402 (indicated as "B/SU") to the cell cultures. All cells were grown in RPMI medium containing 0% (v/v) FBS on day 1 (first 24 hours), 0.2% (v/v) FBS on day 2 (24-48 hours) and 2% (v/v) FBS on days 3 and 4 (48-96 hours). The full name of each marker gene is provided in Table 1.

FIG. 3A shows that expression of FGF8 increased to near its maximum level within 6 hours after treatment with activin A. FGF8 expression remained high for about 24 hours and then began to decline thereafter. Treatment with BMP4/SU5402 caused very little change in the level of FGF8 expression. (FIG. 3A). These results demonstrate that activin A mediates a rapid transition of hESCs to FGF8 expressing cells. As FGF8 expression is one the first indicators of posterior pattern formation in the epiblast, the rapid up-regulation of FGF8 in differentiating hESCs indicates that these early stage cells have differentiated away from the hESC cell type to form a "pre-streak" (preprimitive streak) cell population.

Figure 3B:
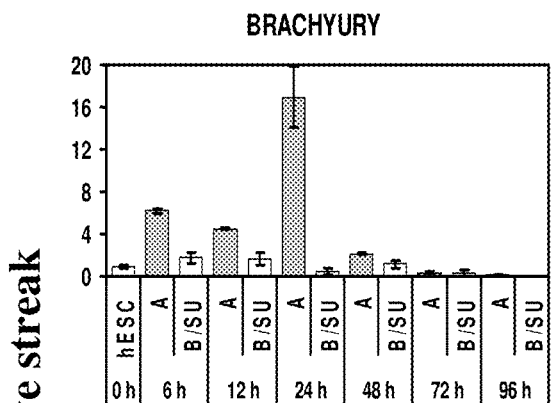
Figure 3C:
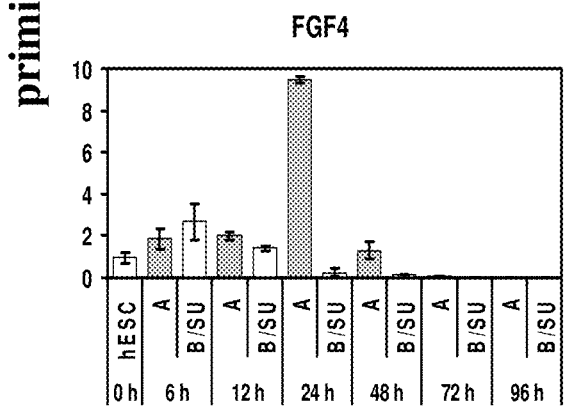
Figure 3D:
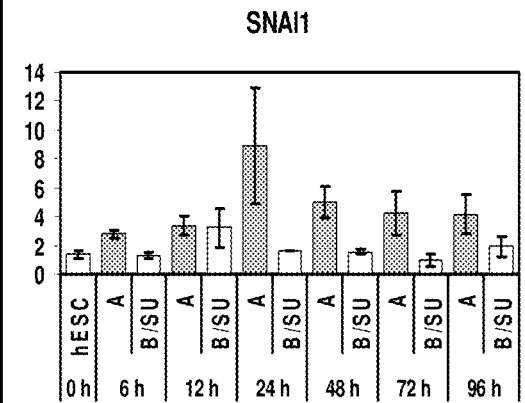
Figure 3E:
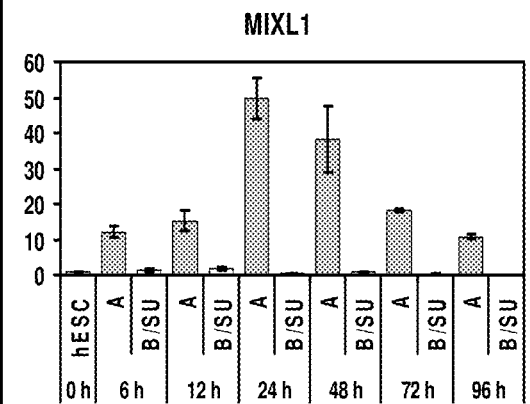
Figure 3F:
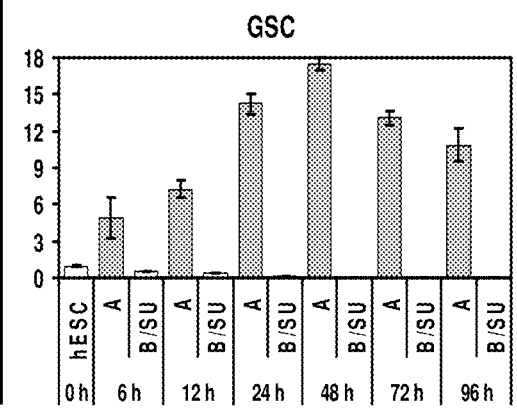

As shown in FIGS. 3B-3F, the induction of certain primitive streak (mesendoderm) markers, such as brachyury, FGF4, SNAI1 MIXL1 and GSC, began at about 6 hours after treatment with activin A. However, in contrast to FGF8 induction, expression of these markers continued to increase and reached maximal levels at about 24 hours, or in some cases 48 hours, after the addition of activin A. Little to no increased expression of any of the primitive streak markers was observed in the BMP4/SU5402 treated cultures (FIGS. 3B-F). Furthermore, the expression levels of brachyury and FGF4, which are not expressed in definitive endoderm cells, down-regulated extremely rapidly to at or below hESC levels by 48-72 hours post activin A treatment (FIGS. 3B-3C). In contrast, SNAI1 MIXL1, and GSC continued to be significantly expressed at 48-96 hours (FIGS. 3D-3F).

Figure 3G:
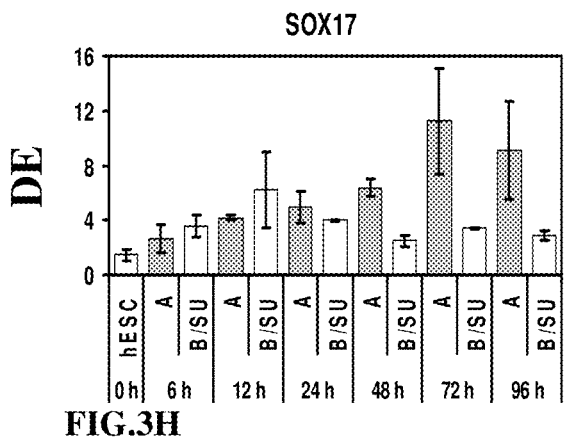
Figure 3J:
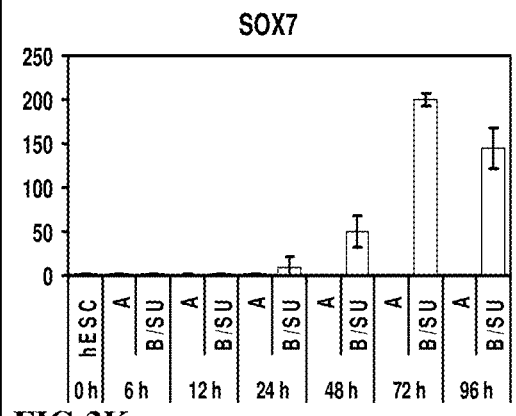
Figure 3H:
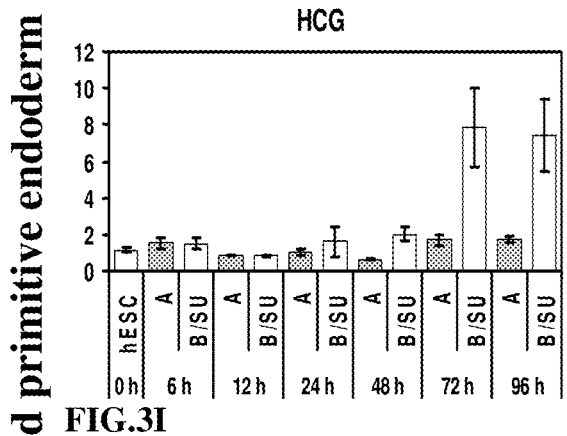
Figure 3K:
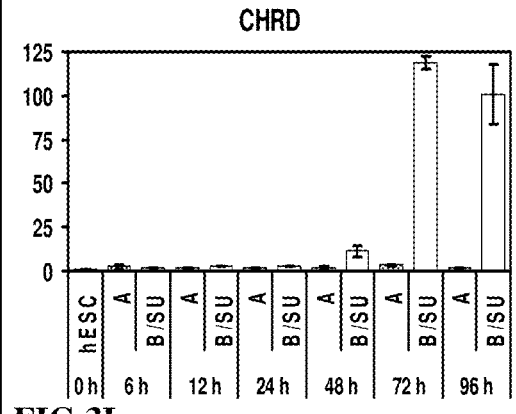
Figure 3I:
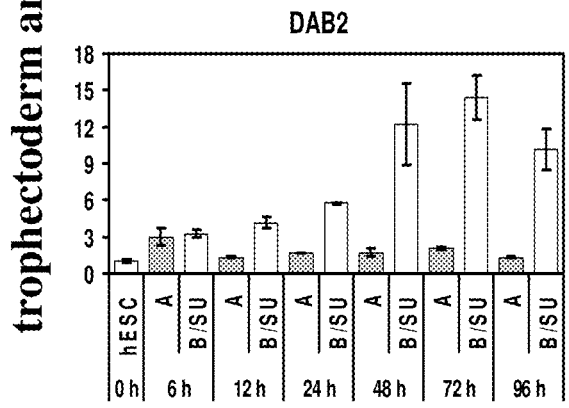
Figure 3L:
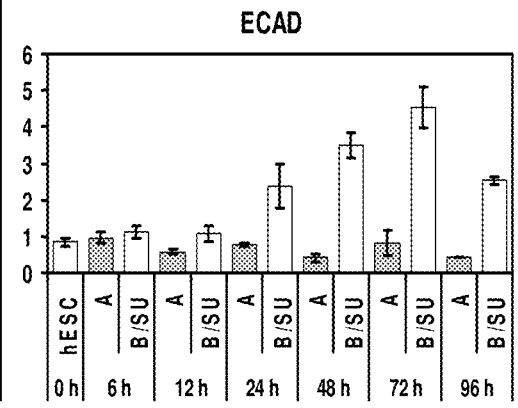

At about 72 hours after treatment with activin A, SOX17 displayed robust up-regulation, which is consistent with a transition from a primitive streak (mesendoderm) intermediate to a definitive endoderm cell fate (FIG. 3G). No such upregulation of SOX17 expression occurred in the BMP4/SU5402 treated cell cultures (FIG. 3G).

This temporal sequence of gene expression just described for the activin A-treated, in vitro cell cultures mimics events that occur in early vertebrate gastrulation, and thus, suggests that the hESCs are transitioning through similar intermediates during this differentiation process.

In addition to the foregoing sequence of events leading to definitive endoderm, FIGS. 3H-3L show that at about 24 to 48 hours, robust upregulation of trophectoderm and primitive endoderm markers, such as HCG, DAB2, SOX7, CHRD and E-cadherin (ECAD), began in cells treated with BMP4/SU5402. The upregulation of these markers continued through 72 and 96 hours. In contrast, no upregulation of HCG, DAB2, SOX7, CHRD or E-cadherin occurred in the cell cultures exposed to 100 ng/ml activin A (FIGS. 3H-L). These results indicate that hESCs have the potential to differentiate to trophectoderm and primitive endoderm under appropriate conditions, however, differentiation to these lineages did not occur to a significant degree in activin treated cultures.

Example 5

Human Embryonic Stem Cell Epithelial to Mesenchymal Transition

During vertebrate gastrulation epiblast cells undergoing epithelial to mesenchymal transition (EMT) at the primitive streak alter the expression pattern of E-cadherin protein on the cell surface. The combined actions of FGF and TGFβ signaling serve to induce the zinc-finger transcription factor SNAI1 which is a direct transcriptional repressor of E-cadherin. This Example shows that transcription of E-cadherin is repressed during the early differentiation stages of activin-exposed hESC cultures in vitro just as in the EMT that occurs in vivo during gastrulation.

Figure 4A:
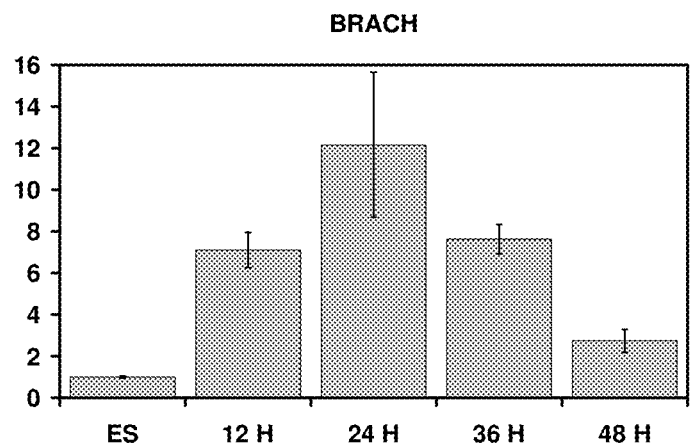
FIGS. 4A-4C are bar charts showing the mRNA expression patterns of (A) the Brachyury marker for mesendoderm (BRACH), (B) the E-cadherin marker for hESCs, and (C) the SNAI1 marker for mesendoderm during the first 48 hours of differentiation from hESCs (indicated by "ESC") in the presence of 100 ng/ml activin A and 0.1% (v/v) FBS.
Figure 4B:
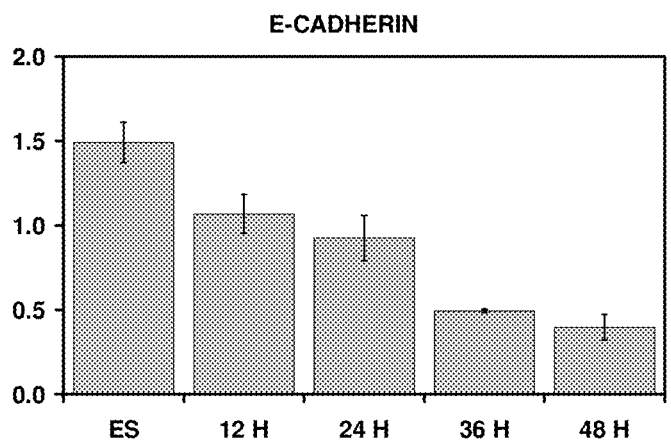
Figure 4C:
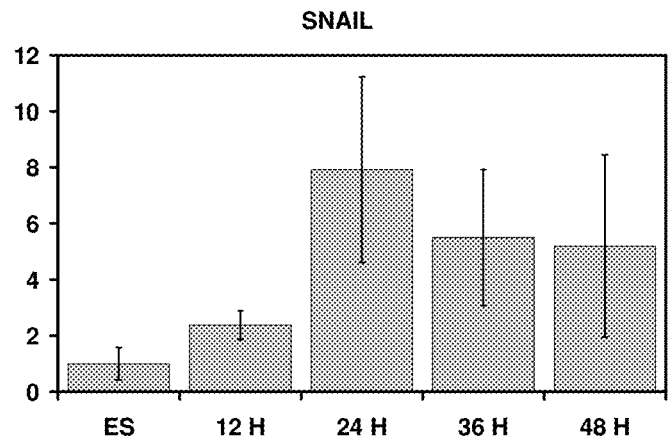

Human embryonic stem cell cultures were differentiated for two days in the presence of 100 ng/ml activin A in RMPI medium containing 0.1% (v/v) FBS. Expression of certain marker genes was determined using Q-PCR and/or immunocytochemistry. FIGS. 4A-4C show the QPCR-determined expression of brachyury, E-cadherin and SNAI1 mRNA, respectively Immunocytochemistry was used to determine the expression of brachyury, E-cadherin and activated (un-phosphorylated) B-catenin.

Figure 7:
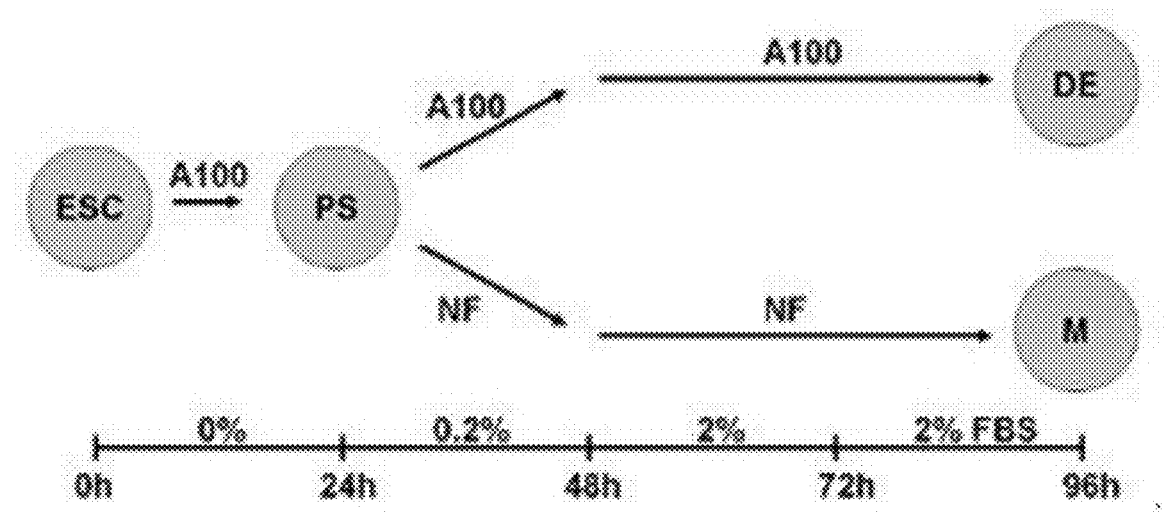
FIG. 7 is a diagram depicting the differentiation of embryonic stem cells (ESC) under low serum conditions in the presence of 100 ng/ml activin A (A100) or in its absence (NF). PS indicates primitive streak cells (mesendoderm cells); DE indicates definitive endoderm cells; and M indicates mesoderm cells.
Figure 8A:
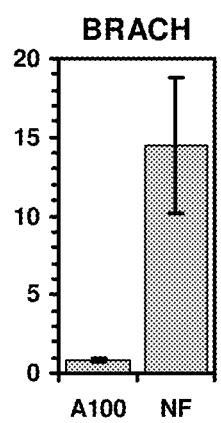
FIGS. 8A-8F are bar charts showing the expression of the mesoderm marker genes, (A) BRACH, (B) FOXF1, (C) FLK1, (D) BMP4, (E) MOX1 and (F) SDF1, in cell cultures after four days of incubation in the continued presence of 100 ng/ml activin A (A100) or after four days of incubation wherein activin A is withdrawn after the first day (NF). Marker expression was determined by Q-PCR.
Figure 8B:
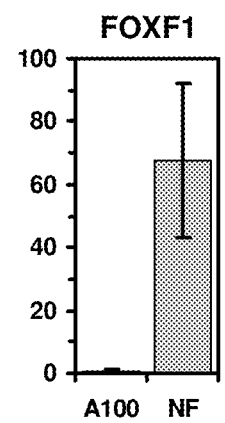
Figure 8C:
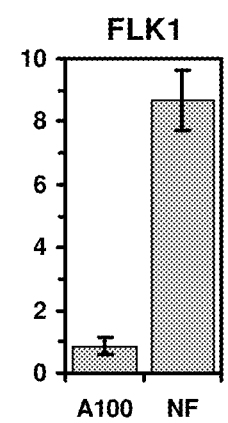
Figure 8D:
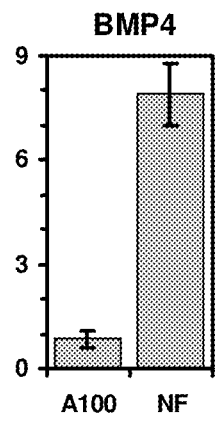
Figure 8E:
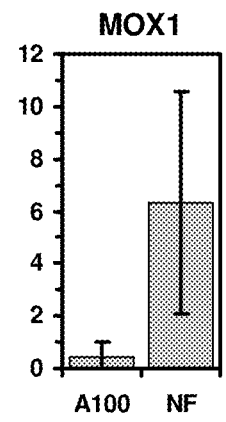
Figure 8F:
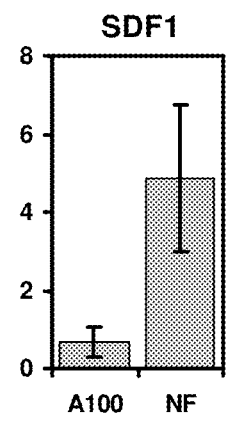

As described previously, activin exposed preprimitive streak cells in culture differentiated to primitive streak (mesendoderm) cells after about 24 hours of activin exposure (Example 4 and FIG. 7). A comparison of FIG. 4A with 4C shows that both brachyury and SNAI1mRNA levels peaked at about 24 hours. A similar peak in expression was seen for FGF4 mRNA (FIG. 3C). In relation to brachyury expression during this time period, the expression of E-cadherin mRNA was decreasing and continued to decrease more than 3-fold by 48 hours after the initiation of activin A treatment (FIG. 4B). By 12 hours post activin exposure, when E-Cadherin mRNA levels had dropped by about 33% from their original levels in the differentiating cell culture, there was a simultaneous disappearance of the characteristic apical cell surface immunolocalization of E-cadherin (presumably involved in adherens junctions) in brachyury positive cells at the periphery of colonies. After 24 hours, as the number of brachyury expressing cells increased, the loss of junction-associated E-Cadherin in brachyury positive cells was more robust. In addition, the morphology of the cells appeared less uniform as evidenced by the differences in morphology of DAPI and brachyury-stained nuclei at both 12 and 24 hours, further supporting occurrence of an EMT.

In addition to the foregoing gene expression, the intracellular localization of β-catenin was determined as hESCs differentiated to definitive endoderm. Using an antibody that recognized only the unphosphorylated (Ser37 and Thr41) form of β-catenin, it was found that this protein was localized only at the cytoplasmic surface in undifferentiated hESCs. By 17 hours post activin treatment, both nuclear and membrane bound β-catenin was detected in both brachyury-negative and brachyury-expressing cells. Furthermore, western blot analyses confirmed the presence of β-catenin in the soluble, membrane-excluded protein fractions of differentiating but not undifferentiated cells. These results are consistent with the hypothesis that the nuclear localization□ of β-catenin occurs in advance of brachyury protein expression. Additionally, taken together, the above data suggest that in activin-exposed cell cultures, as the primitive streak-like state develops, a classical EMT occurs in which activated β-catenin translocates to the nucleus in advance of the expression of brachyury protein and coincides with disassembly of adherens junctions at the epithelial borders between cells.

Example 6

Differentiation of Mesendoderm to Definitive Endoderm

This Example demonstrates the competency of mesendoderm precursor cells to differentiate into definitive endoderm.

Figure 5A:
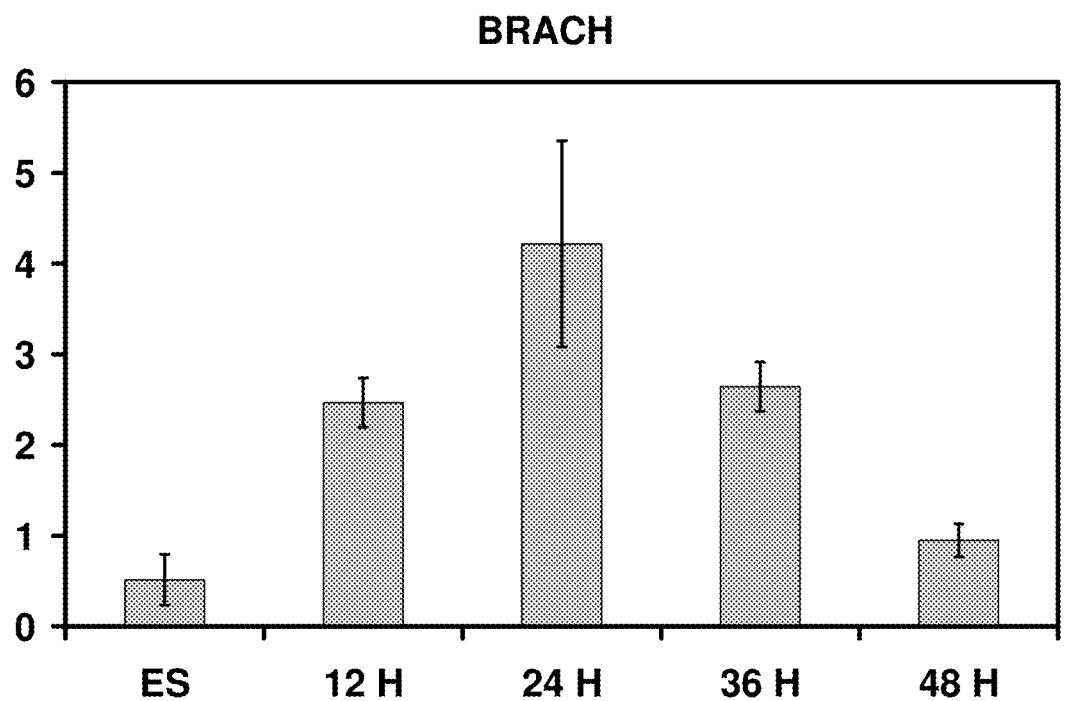
FIGS. 5A-5B are bar charts showing the mRNA expression patterns of the Brachyury marker for mesendoderm (BRACH) and the Sex Determining Region Y-Box 17 (SOX17) marker for definitive endoderm, respectively, during the first 48 hours of differentiation from hESCs (indicated by "ES") in the presence of 100 ng/ml activin A and 0.1% (v/v) FBS.
Figure 5B:
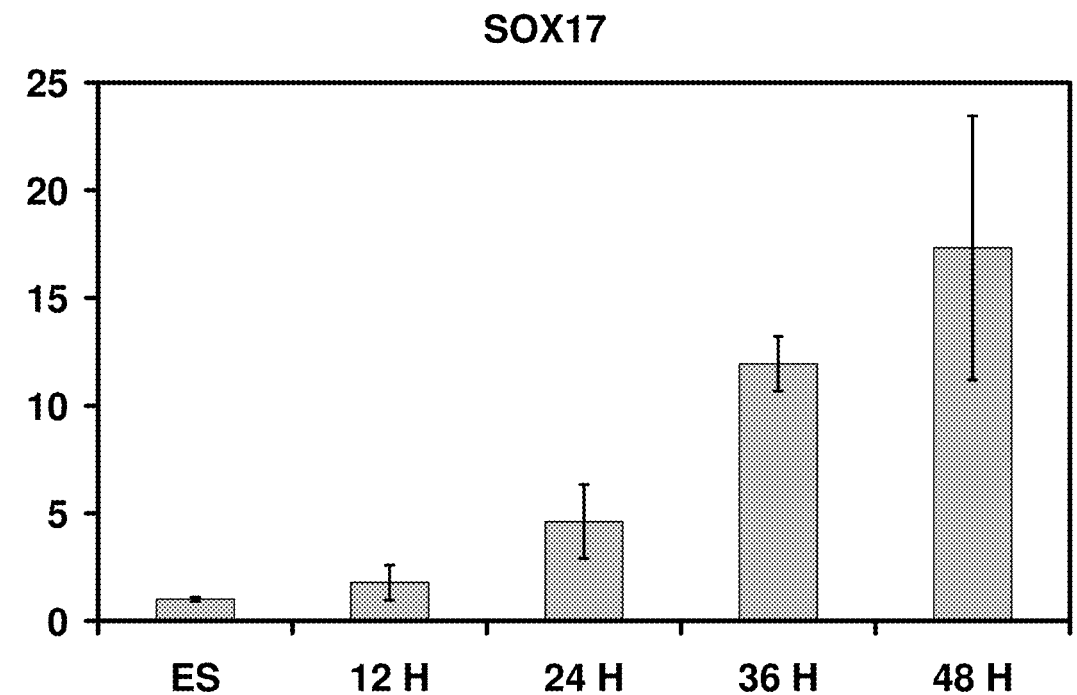
Figure 6A:
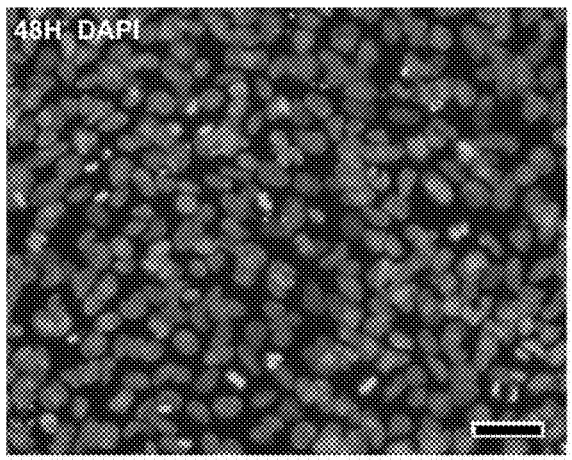
FIGS. 6A-6D are micrographs which show cells 48 hours after differentiation from hESCs in the presence of 100 ng/ml activin A and 0.1% (v/v) FBS. Panel A shows a field of cells stained with DAPI. Panels B-D show the same field of cells stained using a primary antibodies against Brachyury (B), SOX17 (C), or both Brachyury and SOX17 (D).
Figure 6B:
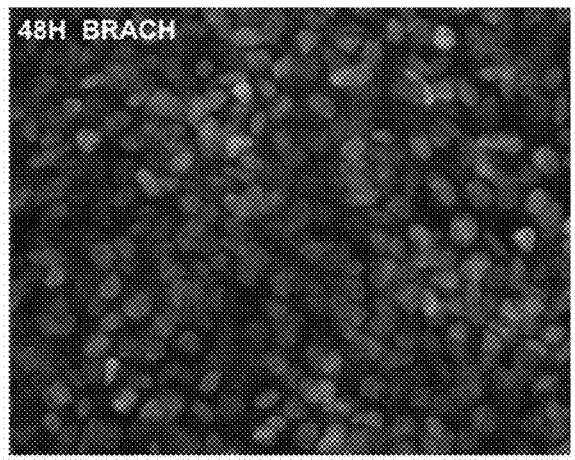
Figure 6C:
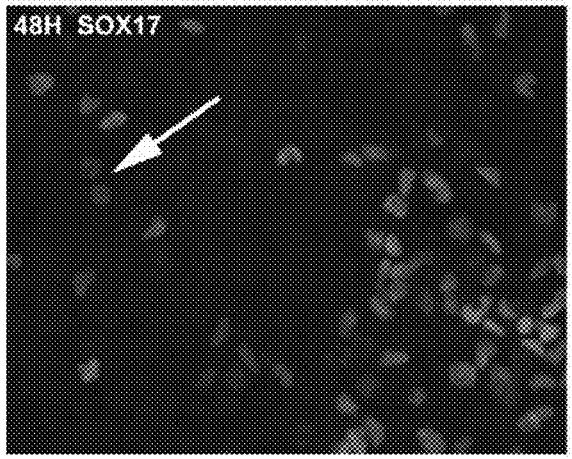
Figure 6D:
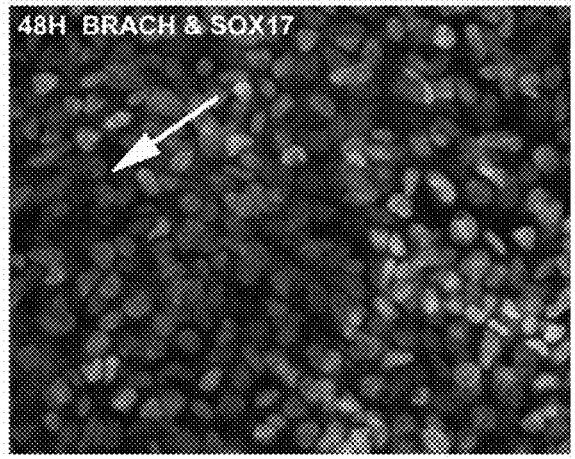

Human embryonic stem cell cultures were incubated for two days in the presence of 100 ng/ml activin A in RPMI medium having a serum concentration of 0.1% (v/v) FSB. As shown in FIG. 5A, brachyury mRNA expression peaked at about 24 hours. At this same time, the expression of the SOX17 gene began to increase (FIG. 5B). By about 48 hours, brachyury mRNA expression had returned to baseline levels (FIG. 5A) and SOX17 was expressed at about 18-fold above baseline (FIG. 5B). These results, which have been verified more than seven independent experiments, are consistent with the hypothesis that brachyury expressing mesendoderm cells begin a conversion to SOX17-expressing definitive endoderm at around 36-48 hours post activin treatment.

To demonstrate the validity of the above hypothesis, immunocytochemistry-based analysis of the brachyury and SOX17 markers was performed. The time course for brachyury protein expression shows the appearance of immunoreactive cells which began at the periphery of most large colonies at 12 hrs and rapidly spread to the interior of the colonies by 36-48 hours. At these later times, the majority of the cells in the culture were positive for brachyury protein. As such, the brachyury protein expression pattern was delayed by 12-24 hours in relation to the peak of brachyury mRNA expression shown in FIG. 5A. After 48 hours of differentiation, when SOX17 mRNA and protein expression were rapidly increasing and brachyury expression was rapidly decreasing, most of the SOX17 positive cells co-expressed brachyury (FIGS. 6A-6D). These data clearly demonstrate that, in the presence of 100 ng/ml activin and low serum, the majority of SOX17 positive cells were derived from brachyury-positive, mesendoderm cells. Furthermore, this finding is highly suggestive of the existence of a mesendoderm intermediate in human development. Additionally, since brachyury expression does not occur in cells of the primitive endoderm lineages at any time during development, these findings conclusively prove the definitive nature of the activin-produced endoderm.

Example 7

Formation of Mesoderm and Definitive Endoderm from Mesendoderm Cells

In addition to the foregoing Example, experiments were conducted to demonstrate that the mesendoderm intermediates described herein can undergo differentiation to either mesoderm or definitive endoderm cells.

FIG. 7 shows the experimental design and culture conditions used in this Example. Specifically, two parallel hESCs were cultured for four days in RPMI medium. As in Example 4, the serum concentration of this medium was adjusted such that it contained 0% (v/v) FBS on the first day, 0.2% (v/v) FBS on the second day and 2% (v/v) FBS on the third and fourth days. In each of the parallel cultures, activin A was supplied in the culture medium at a concentration of 100 ng/ml for the first 24 hours. At the end of this time period, activin A was removed from one of the parallel cultures (NF) and maintained in the other (A100).

Figure 9A:
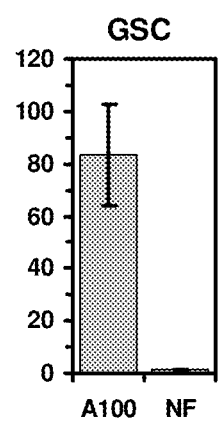
FIGS. 9A-9C are bar charts showing the expression of the definitive endoderm marker genes, (A) GSC, (B) SOX17 and (C) FOXA2, in cell cultures after four days of incubation in the continued presence of 100 ng/ml activin A (A100) or after four days of incubation wherein activin A is withdrawn after the first day (NF). Marker expression was determined by Q-PCR.
Figure 9B:
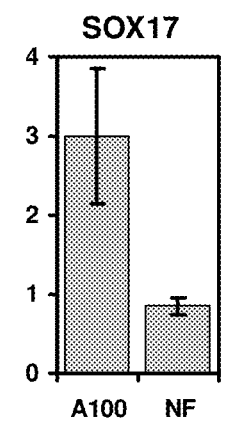
Figure 9C:
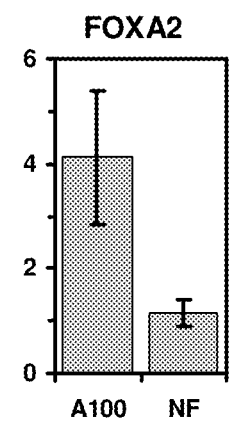
Figure 10A:
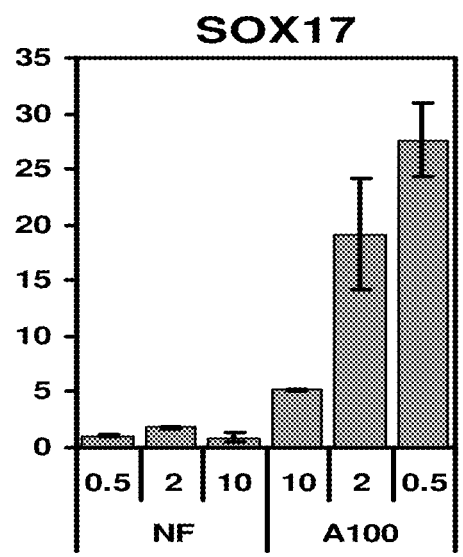
FIGS. 10A-10I are bar charts showing the expression patterns of certain marker genes useful for the identification and/or detection of definitive endoderm cells. Marker expression was determined by Q-PCR from five-day-old cell cultures containing fetal bovine serum (FBS) at a concentration of 0.5%, 2% or 10% and either 100 ng/ml activin A (A100) or no activin A (NF).
Figure 10B:
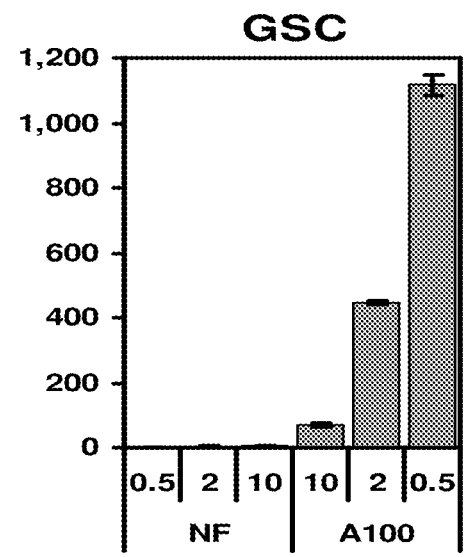
Figure 10C:
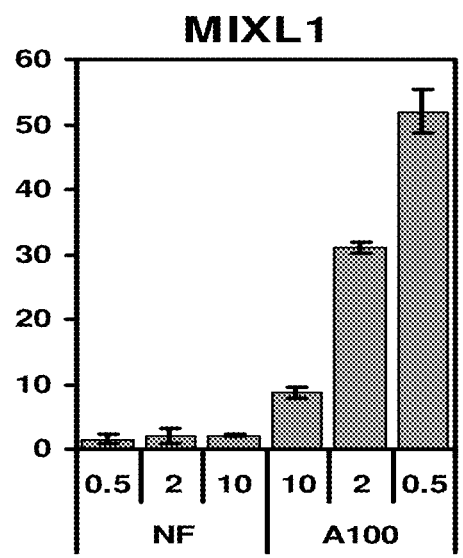
Figure 10D:
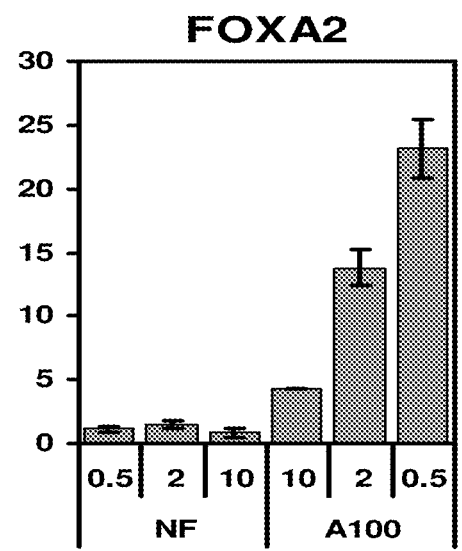
Figure 10E:
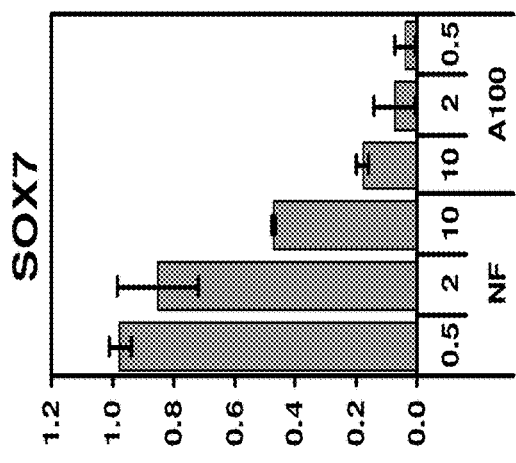
Figure 10F:
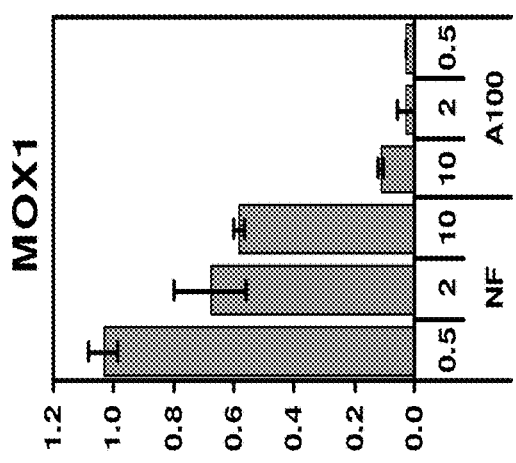
Figure 10H:
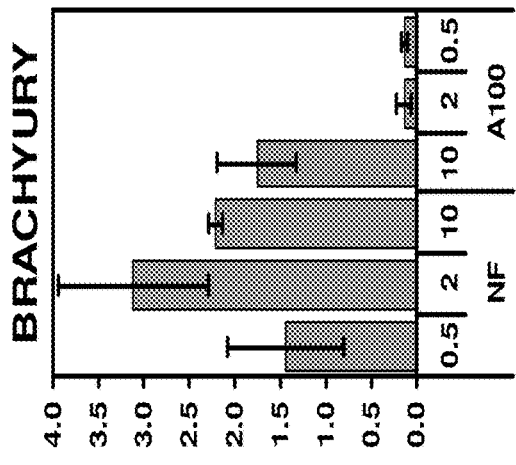
Figure 10G:
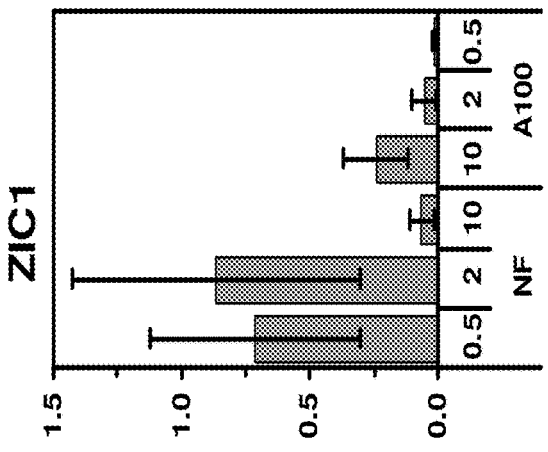
Figure 10I:
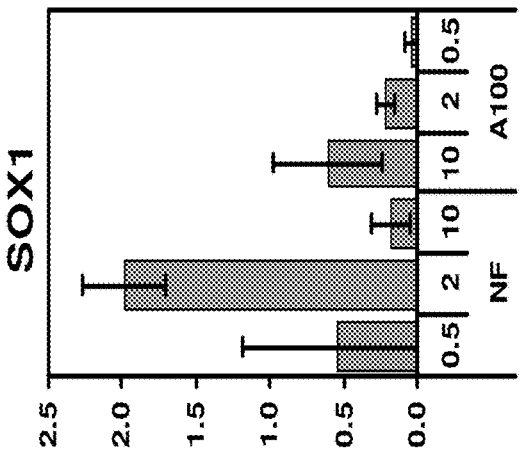

FIGS. 8A-8F show that there was a lack of expression for the mesoderm markers brachyury, MOX1, FOXF1, FLK1, BMP4, and SDF1 under high activin and low PBS conditions. These results demonstrate that the brachyury/FGF4/MIXL1-expressing mesendoderm cells were patterned towards the production of definitive endoderm rather than to mesoderm under high activin A conditions. This was also demonstrated by the robust expression of definitive endoderm markers, GSC, SOX17 and FOXA2 in the culture treated with activin over the entire four day period (FIGS. 9A-9C). In contrast, removal of activin A at 24 hours, which simulates lower nodal/activin signaling, resulted in a dramatic loss of definitive endoderm gene expression (FIGS. 9A-9C) simultaneously with a dramatic gain of mesoderm character (FIGS. 8A-8F).

Example 8

Definitive Endoderm Production in Medium Containing 0.5% Serum

To further demonstrate the effect of serum reduction on the production of definitive endoderm cells, hESCs were differentiated to definitive endoderm cells medium containing various serum concentrations.

Human embryonic stem cells were cultured for five days in RPMI medium containing 100 ng/ml activin A in the presence of 10% (v/v) FBS, 2% (v/v) FBS or 0.5% (v/v) FBS. Control cell cultures containing no activin A were also established at each of the three test serum levels. For each of these cultures, expression of several marker genes was determined by Q-PCR (FIGS. 10A-10I). Additionally, the amount of the SOX17 protein produced by cells in these cultures was determined by immunocytochemistry using the antibody to SOX17 that has been previously described herein.

FIGS. 10A-10I show the expression of certain definitive endoderm marker genes at varying concentrations of FBS. In particular, FIGS. 10A-10D show that decreasing the serum concentration in cell cultures treated with activin A resulted in substantial increases in the production of mRNA corresponding to the definitive endoderm positive markers, SOX17, GSC, MIXL1 and FOXA2. In the case of markers for which mRNA expression was decreased in response to activin A (markers of non-definitive endoderm cell types, including Brachyury, MOX1, SOX7, SOX1 and ZIC1), decreasing the serum concentrations resulted in substantial decreases in the production of mRNA corresponding to these markers (FIGS. 10E-10I).

The relative proportion of hESC converted to definitive endoderm cells at each of the serum concentrations was determined by immunocytochemistry using antibody to SOX17. After 5 days of differentiation in 100 ng/ml activin A in 0.5% FBS, the proportion of SOX17 positive cells was greater than 80% (>3 separate experiments) and there was no detectable immunoreactivity for alpha-fetoprotein (AFP) or thrombomodulin (THBD), markers of VE/PE and trophectoderm (TE), respectively. The correlation between increasing SOX17 mRNA expression and increasing number of SOX17 immunoreactive cells across these conditions indicates that the relative gene expression measurement is also a reasonable measurement of SOX17-positive cell number within the population.

Example 9

Upregulation of SOX17 Expression Precedes the Upregulation of FOXA2 Expression

This Example demonstrates that in activin-mediated differentiation of hESCs to definitive endoderm, SOX17 mRNA expression is upregulated prior to FOXA2 mRNA expression.

Human embryonic stem cells were cultured in RPMI medium for four days in the presence of activin A and low serum as described previously in Example 4. Expression of SOX17 and FOXA2 mRNA was determined by Q-PCR.

Figure 11A:
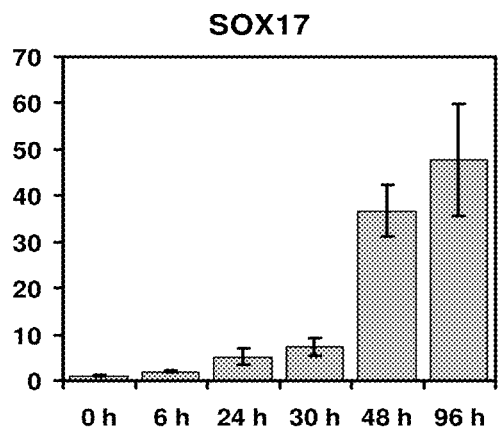
FIGS. 11A-11B are bar charts showing the mRNA expression patterns of definitive endoderm markers (A) SOX17 and (B) FOXA2 in cell cultures differentiated in the presence of 100 ng/ml activin A for four days. Marker expression was determined by Q-PCR during the course of differentiation at 0, 6, 24, 30, 48 and 96 hours after addition of activin A.
Figure 11B:
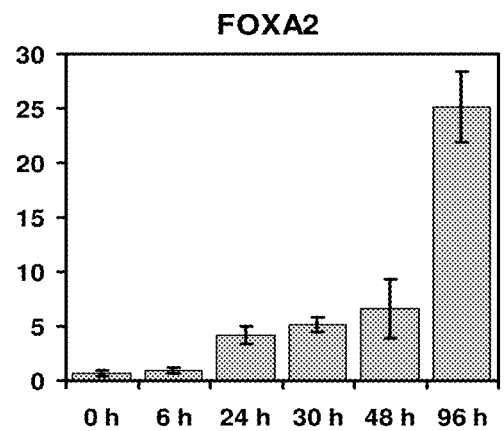

As shown in FIG. 11A, SOX17 mRNA was substantially increased beginning at about 48 hours post activin A addition. A similar substantial increase in expression for FOXA2 mRNA was not observed until about 96 hours post activin A addition. These results are consistent with production of definitive endoderm and not axial mesoderm (see also FIGS. 9A-9C). These results, however, contrast with the temporal expression of SOX17 and FOXA2 in mouse embryoid bodies incubated with activins where FOXA2 expression precedes that of SOX17. As such, it is likely that the mouse embryoid body systems are optimized for the production of axial mesoderm rather than definitive endoderm.

Example 10

Production of Definitive Endoderm in Eight Different hESC Lines

This Example shows that definitive endoderm cells can be produced from eight independently derived hESC lines using the methods described herein.

Eight different hESC lines (CyT25, CyT-DM3, BG01, BG02, BG03, H7, H9 and HUES7) were cultured separately for five days in the presence of 100 ng/ml activin A in low serum RPMI medium. Specifically, the RPMI medium contained 0% (v/v) FBS on day 1, 0.2% (v/v) FBS on day 2 and 2% (v/v) FBS on days 3-5.

Each of the eight cell lines differentiated to SOX17/CXCR4-positive definitive endoderm cells.

Example 11

Transplantation of Human Definitive Endoderm Cells under Mouse Kidney Capsule

To demonstrate that the human definitive endoderm cells produced using the methods described herein are capable of responding to differentiation factors so as to produce cells derived from the gut tube, such human definitive endoderm cells were subjected to an in vivo differentiation protocol.

Human definitive endoderm cells were produced as described in the foregoing Examples. Such cells were harvested and transplanted under the kidney capsule of immunocompromised mice using standard procedures. After three weeks, the mice were sacrificed and the transplanted tissue was removed, sectioned and subjected to histological and immunocytochemical analysis.

Figure 12B:
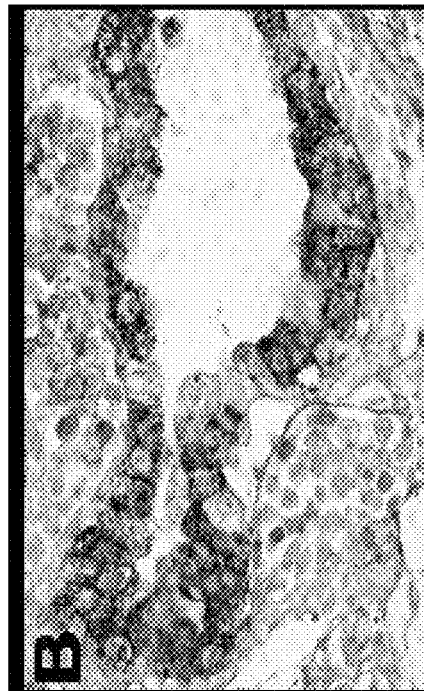
FIGS. 12A-12D show the in vivo differentiation of definitive endoderm cells that are transplanted under the kidney capsule of immunocompromised mice. Panels: A—hetatoxylin-eosin staining showing gut-tube-like structures; B—antibody immunoreactivity against hepatocyte specific antigen (liver); C—antibody immunoreactivity against villin (intestine); and D—antibody immunoreactivity against CDX2 (intestine).
Figure 12D:
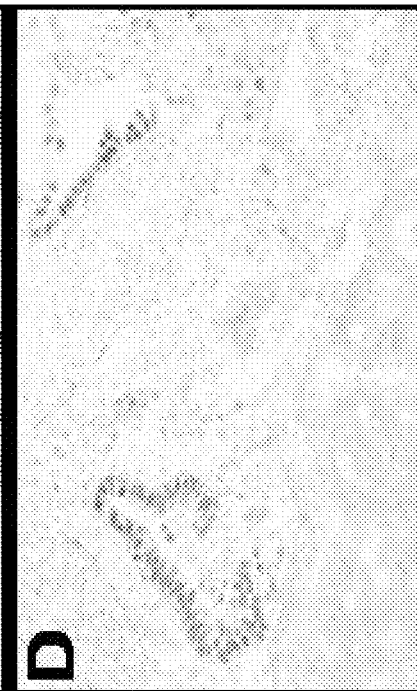
Figure 12A:
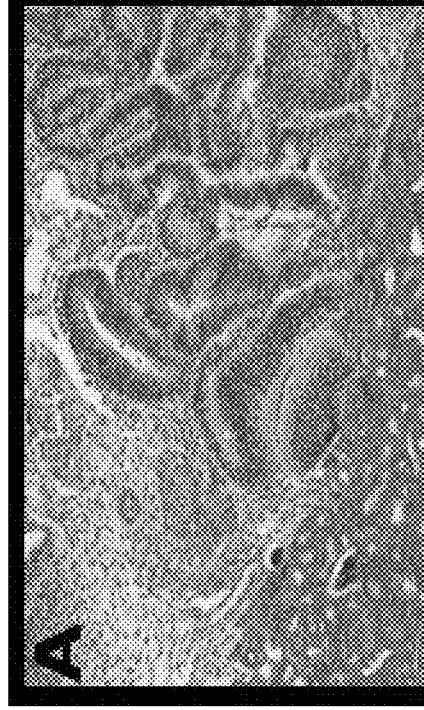
Figure 12C:
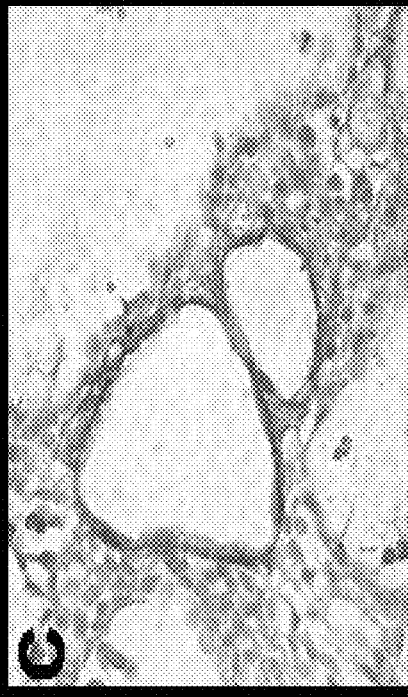

FIGS. 12A-12D show that after three weeks post-transplantation, the human definitive endoderm cells differentiated into cells and cellular structures derived from the gut tube. In particular, FIG. 12A shows hematoxylin and eosin stained sections of transplanted human definitive endoderm tissue that has differentiated into gut-tube-like structures. FIG. 12B shows a transplanted human definitive endoderm section immunostained with antibody to hepatocyte specific antigen (HSA). This result indicates that the human definitive endoderm cells are capable of differentiating into liver or liver precursor cells. FIGS. 12C and 12D show a transplanted human definitive endoderm section immunostained with antibody to villin and antibody to caudal type homeobox transcription factor 2 (CDX2), respectively. These results indicate that the human definitive endoderm cells are capable of differentiating into intestinal cells or intestinal cell precursors.

Example 12

Generation of FGF8 Promoter-EGFP and Brachyury Promoter-EGFP Transgenic Human Embryonic Stem Cell Lines In order to use the FGF8 and brachyury markers for cell isolation, hESCs having FGF8 or brachyury gene promoters fused with an expressible reporter gene are constructed. In particular, this Example describes the construction of a vector comprising a reporter cassette which comprises a reporter gene under the control of the FGF8 regulatory region. Additionally, the construction of a vector comprising a reporter cassette which comprises a reporter gene under the control of the brachyury regulatory region is described. This Example also describes the preparation of a cell, such as a human embryonic stem cell, transfected with one or more of these vectors as well as a cell having this one or both of these reporter cassettes integrated into its genome.

FGF8-expressing preprimitive streak cell lines and brachyury-expressing mesendoderm cell lines genetically tagged with a reporter gene are constructed by placing a GFP reporter gene under the control of the regulatory region (promoter) of the FGF8 gene or the brachyury gene, respectively. First, a plasmid construct in which EGFP expression is driven by the human FGF8 or brachyury gene promoter is generated by replacing the CMV promoter of vector pEGFP-N1 (Clontech) with the human FGF8 or brachyury control region. These control regions contain the characterized regulatory elements of either the FGF8 or the brachyury gene, and they is sufficient to confer the normal expression pattern of these genes in transgenic mice. In the resulting vector, expression of EFGP is driven by either the FGF8 promoter or the brachyury promoter. In some experiments, this vector can be transfected into hESCs.

The FGF8 promoter/EGFP cassette or the brachyury promoter/EGFP cassette is excised from the above vector, and then subcloned into a selection vector containing the neomycin phosphotransferase gene under control of the phosphoglycerate kinase-1 promoter. The selection cassette is flanked by flp recombinase recognition sites to allow removal of the cassette. This selection vector is linearized, and then introduced into hESCs using standard lipofection methods. Following 10-14 days of selection in G418, undifferentiated transgenic hESC clones are isolated and expanded.

It will be appreciated that vectors containing GFP or EGFP reporter genes under the control of the FGF4 or SNAI1 promoter can also be constructed. Furthermore, it will be appreciated that reporter genes other than GFP or EGFP can be used in any of the above-described constructs provided that the reporter allows for cell separation by FACS.

Example 13

Production of Cell Populations Enriched in Preprimitive Streak Cells

The following Example demonstrates that hESCs comprising an FGF8 promoter/EGFP cassette can be differentiated into preprimitive streak cells and then subsequently isolated by fluorescence-activated cell sorting (FACS).

FGF8 promoter/EGFP transgenic hESCs are differentiated for approximately 6, 12 and 18 hours in growth medium containing 100 ng/ml activin A and no serum. The differentiated cells are then harvested by trypsin digestion and sorted on a Becton Dickinson FACS Diva directly into RNA lysis buffer or PBS. A sample of single live cells is taken without gating for EGFP and single live cells are gated into EGFP positive and GFP negative populations. In a separate experiment, the EGFP positive fraction is separated into two equally sized populations according to fluorescence intensity (Hi and Lo).

Following sorting, cell populations are analyzed by both Q-PCR and immunocytochemistry. For Q-PCR analysis, RNA is prepared using Qiagen RNeasy columns and then converted to cDNA. Q-PCR is conducted as described previously. For immunocytochemistry analysis, cells are sorted into PBS, fixed for 10 minutes in 4% paraformaldehyde, and adhered to glass slides using a Cytospin centrifuge. The primary antibody is to β-catenin. An appropriate secondary antibody conjugated to FITC (green) or Rhodamine (Red) is used to detect binding of the primary antibody.

Sorted cells are further subjected to Q-PCR analysis. Differentiated cells show a correlation of EGFP fluorescence with endogenous FGF8 gene expression.

Compared to non-fluorescing cells, the EGFP positive cells show a greater than 2-fold increase in FGF8 expression levels. The separation of high and low EGFP intensity cells indicates that EGFP expression level correlates with FGF8 expression level. In addition to FGF8 marker analysis, sorted cells are subjected to immunocytochemistry analysis of nuclear-localized β-catenin (nuclear β-catenin). Nuclear localization of this marker is enriched in the EGFP positive fraction. In contrast, little nuclear localization of β-catenin is seen in the EGFP negative fraction.

Given these results, at least about 5% of the cells present in the differentiated cell cultures prior to sorting are FGF8/nuclear β-catenin-positive cells. At least about 90% of the cells in the sorted cell populations are FGF8/nuclear β-catenin-positive preprimitive streak cells.

Example 14

Production of Cell Populations Enriched in Mesendoderm Cells

The following Example demonstrates that hESCs comprising a brachyury promoter/EGFP cassette can be differentiated into primitive streak (mesendoderm) cells and then subsequently isolated by fluorescence-activated cell sorting (FACS).

Brachyury promoter/EGFP transgenic hESCs are differentiated for approximately 24 hours in growth medium containing 100 ng/ml activin A and no serum or 100 ng./ml activin A and 0.1% (v/v) FBS. The differentiated cells are then harvested by trypsin digestion and sorted on a Becton Dickinson FACS Diva directly into RNA lysis buffer or PBS. A sample of single live cells is taken without gating for EGFP and single live cells are gated into EGFP positive and GFP negative populations. In a separate experiment, the EGFP positive fraction is separated into two equally sized populations according to fluorescence intensity (Hi and Lo).

Following sorting, cell populations are analyzed by both Q-PCR and immunocytochemistry. For Q-PCR analysis, RNA is prepared using Qiagen RNeasy columns and then converted to cDNA. Q-PCR is conducted as described previously. For immunocytochemistry analysis, cells are sorted into PBS, fixed for 10 minutes in 4% paraformaldehyde, and adhered to glass slides using a Cytospin centrifuge. The primary antibodies are to FGF4 and SNAI1. Appropriate secondary antibodies conjugated to FITC (green) or Rhodamine (Red) are used to detect binding of the primary antibodies.

Sorted cells are further subjected to Q-PCR analysis. Differentiated cells show a correlation of EGFP fluorescence with endogenous brachyury gene expression. Compared to non-fluorescing cells, the EGFP positive cells show a greater than 2-fold increase in brachyury expression levels. The separation of high and low EGFP intensity cells indicates that EGFP expression level correlates with brachyury expression level. In addition to brachyury marker analysis, sorted cells are subjected to immunocytochemistry analysis of FGF4 and SNAI1. Each of these markers are enriched in the EGFP positive fraction. In contrast, little FGF4 and/or SNAI1 is seen in the EGFP negative fraction.

Given these results, at least about 5% of the cells present in the differentiated cell cultures prior to sorting are brachyury/FGF4/SNAI1-positive cells. At least about 90% of the cells in the sorted cell populations are brachyury/FGF4/SNAI1-positive mesendoderm cells.

It will be appreciated that, as an alternative to vectors comprising an EGFP/brachyury construct, vectors comprising a GFP or EGFP reporter gene under the control of the FGF4 or SNAI1 promoter can be used in the mesendoderm enrichment methods described in this Example.

Example 15

Identification of Differentiation Factors Capable of Promoting the Differentiation of Human Preprimitive Steak and/or Mesendoderm Cells In Vitro To exemplify the differentiation factor screening methods described herein, populations of human preprimitive streak and mesendoderm cells produced using the methods described herein are separately provided with several candidate differentiation factors while determining the normalized expression levels of certain marker gene products at various time points.

Human preprimitive streak and mesendoderm cell cultures are produced as described in the foregoing Examples. In brief, hESCs cells are grown in the presence of 100 ng/ml activin A in RPMI medium without serum for 12 hours (preprimitive streak) or 24 hours (mesendoderm). After formation of preprimitive streak cells and mesendoderm cells, the cell populations are maintained in individual plates in RPMI containing 0.2% FBS and are treated with one of: Wnt3B at 20 ng/ml, FGF2 at 5 ng/ml or FGF2 at 100 ng/ml. The expression of marker gene products for albumin, PROX1 and TITF1 are quantitated using Q-PCR.

Incubation of the preprimitive streak cells and the mesendoderm cells with the above-mentioned molecules is expected to cause the preprimitive streak cells and the mesendoderm cells to differentiate to cells derived from the definitive endoderm lineage.

Example 16

Summary of Marker Expression in Early Embryonic Cell Types

This Example provides a Table which summarizes the expression of marker genes useful in the identification and/or detection of cell types obtained during the early differentiation of hESCs. In Table 1 below the full name and abbreviation for each marker is provided in the first two columns. Each of the next columns describes whether the gene is expressed in a specific tissue type. The following abbreviations for cell type are used: ICM/ESC refers to hESCs; PS refers to primitive streak (mesendoderm) cells; Ecto refers to ectoderm cells; Meso refers to mesoderm cells; DE refers to definitive endoderm cells; PrE refers to primitive endoderm; VE refers visceral endoderm; and PE refers to parietal endoderm.

TABLE 1

| Gene Name | Gene Abb. | Expression domains - gastrulation stage | | | | | | |
|---|---|---|---|---|---|---|---|---|
| | | ICM/ESC | PS | Ecto | Meso | DE | PrE/VE/PE | TE |
| fibroblast growth factor 8 | FGF8 | − | + | − | + | + | + | − |
| brachyury | BRACH | − | + | − | + | − | − | − |
| fibroblast growth factor 4 | FGF4 | + | + | − | + | − | − | − |
| snail homolog 1 (Drosophila) | SNAI1 | − | + | − | + | + | + | + |
| Mix1 homeobox (Xenopus laevis)-like 1 | MIXL1 | − | + | − | + | + | + | − |
| goosecoid | GSC | − | + | − | + | + | + | − |
| SRY (sex determining region Y)-box 17 | SOX17 | − | − | − | − | + | + | − |
| chemokine (C—X—C motif) receptor 4 | CXCR4 | − | − | − | + | + | − | − |
| hepatocyte nuclear factor 3, beta | FOXA2 | − | + | − | + | + | + | − |
| disabled homolog 2 | DAB2 | − | − | − | − | − | + | − |
| SRY (sex determining region Y)-box 7 | SOX7 | − | − | − | − | − | + | − |
| chordin | CHRD | − | + | − | + | + | + | − |
| E-cadherin (epithelial) | ECAD | + | − | + | − | +/− | + | + |
| SRY (sex determining region Y)-box 1 | SOX1 | − | − | + | − | − | − | − |
| zinc finger protein of the cerebellum 1 | ZIC1 | − | − | +/− | +/− | − | − | − |
| POU domain, class 5, transcription factor 1 | OCT4 | + | − | − | − | − | + | − |
| forkhead box F1 | FOXF1 | − | − | − | + | − | − | − |
| mesenchyme homeo box 1 | MOX1 | − | − | − | + | − | − | − |
| VEGFR, kinase insert domain receptor | FLK1 | − | − | − | + | − | − | − |
| bone morphogenetic protein 4 | BMP4 | − | − | − | + | − | − | + |
| stromal cell-derived factor 1 | SDF1 | unk | − | − | + | − | + | + |
| chorionic gonadotropin, beta polypeptide 5 | HCG | − | − | − | − | − | − | + |

Example 17

Additional Markers Useful for Identifying and/or Detecting Preprimitive Streak Cells and Mesendoderm Cells This Example describes additional markers that are useful in identifying and/or detecting preprimitive streak and/or mesendoderm cells. It will be appreciated that the preprimitive streak markers described in this Example can be used in place of or in addition to any of the previously-described markers for preprimitive streak cells. It will also be appreciated that the mesendoderm markers described in this Example can be used in place of or in addition to any of the previously-described markers for mesendoderm cells.

In order to investigate the process of hESC differentiation to preprimitive streak, mesendoderm and subsequently to endoderm and mesoderm, we conducted global expression profiling of differentiating hESC cultures at short time increments under low serum (≤2% (v/v) FBS) and high activin A (100 ng/ml), with or without the addition of the FGF receptor inhibitor, SU5402, after the first 24 hours of differentiation. Adding SU5402 to the activin A at 24 hours resulted in a drastic decrease in expression of genes characteristic of definitive endoderm and greatly increases the expression of mesoderm markers.

To mediate cell differentiation, hESCs were grown in low serum RPMI medium in the presence of 100 ng/ml activin A for 4 days. Serum supplementation was 0% (v/v) for the first 24 hours, 0.2% (v/v) for the second 24 hours and 2% (v/v) for days 3 and 4 of differentiation. After the first 24 hours of differentiation, mesoderm was induced in one set of cultures by the application of SU5402 at 5 µM in addition to the activin A. The other set of cultures remained in activin A alone and thus produced definitive endoderm at high efficiency. Samples were taken in duplicate at 0, 2, 6, 24, 30, 48 and 96 hour time points. The 48 and 96 hour points were either definitive endoderm (activin A alone) or mesoderm (activin A with SU5402). Total RNA was extracted and submitted to Expression Analysis (Durham, N.C.) for global expression profiling using the Affymetrix high-density oligonucleotide arrays (U133 plus 2.0).

Gene expression patterns over the time course of hESC differentiation were studied using hierarchical clustering analyses as well as comparative analyses between groups of paired samples at the various time points. Genes that displayed an expression pattern characterized by a robust increase in expression over the first 6 hours followed by either maintenance or decreases in expression at the later time points were identified as genes involved in differentiation of hESCs to preprimitive streak cells. Genes that displayed peaks in expression at the 24-30 hour time points were identified as genes involved in mesendoderm differentiation.

Table 2 below describes marker genes that were expressed at highly elevated levels by 6 hours after contacting the hESCs with activin A. These genes are indicative of preprimitive streak cells. Table 3, below describes marker genes that were expressed at peak levels by about 24 to about 30 hours after contacting the hESCs with activin A. These genes are indicative of mesendoderm cells. In each of these tables, the first column lists the probe set identification number and the second column provides the Unigene Identification Number. The Unigene database is publicly available via the National Center for Biotechnology Information (NCBI) website. The nucleotide and amino acid sequences for any of the marker genes described in these tables can therefore be obtained by a query for the appropriate Unigene Identification Number at the NCBI website. The Unigene database is incorporated herein by reference in its entirety. Column three of the each table provides the commonly known gene symbol for each of the markers. The remainder of the columns provide the relative levels of gene expression at the 0, 2, 6, 24, 30, 48 and 96 hour time points. As used in these tables, "DE" refers to definitive endoderm and "M" refers to mesoderm.

TABLE 2

| Probe Set Id | Unigene Id | Gene Symbol | 0 hr | 2 hr | 6 hr | 24 hr | 30 hr | 48 hr-DE | 48 hr-M | 96 hr-DE | 96 hr-M |
|---|---|---|---|---|---|---|---|---|---|---|---|
| 208449_s_at | Hs.57710 | FGF8 | 47 | 212 | 534 | 741 | 513 | 390 | 939 | 701 | 93 |
| 230916_at | Hs.370414 | NODAL | 2799 | 4147 | 9451 | 9789 | 12388 | 6368 | 8090 | 8202 | 1921 |
| 213069_at | Hs.477420 | HEG | 76 | 160 | 720 | 567 | 915 | 970 | 619 | 719 | 481 |
| 218839_at | Hs.234434 | HEY1 | 30 | 233 | 999 | 202 | 160 | 38 | 98 | 33 | 768 |
| 209710_at | Hs.367725 | GATA2 | 75 | 283 | 903 | 317 | 197 | 94 | 345 | 132 | 930 |
| 205780_at | Hs.475055 | BIK | 418 | 1061 | 2403 | 804 | 367 | 165 | 1157 | 746 | 1003 |
| 208937_s_at | Hs.504609 | ID1 | 5378 | 13769 | 21979 | 8886 | 7177 | 8627 | 15486 | 6468 | 24305 |

TABLE 3

| Probe Set Id | Unigene Id | Gene Symbol | 0 hr | 2 hr | 6 hr | 24 hr | 30 hr | 48 hr-DE | 48 hr-M | 96 hr-DE | 96 hr-M |
|---|---|---|---|---|---|---|---|---|---|---|---|
| 206783_at | Hs.1755 | FGF4 | 1138 | 1401 | 1558 | 4521 | 3291 | 2538 | 3581 | 181 | 932 |
| 229103_at | Hs.445884 | WNT3 | 234 | 240 | 717 | 1415 | 859 | 1123 | 758 | 881 | 77 |
| 231746_at | Hs.282079 | MIXL1 | 286 | 427 | 1252 | 12014 | 12911 | 11598 | 4121 | 5674 | 152 |
| 206619_at | Hs.159311 | DKK4 | 35 | 14 | 16 | 3876 | 3218 | 3877 | 7 | 19 | 22 |
| 219480_at | Hs.48029 | SNAI1 | 78 | 131 | 249 | 525 | 434 | 536 | 338 | 243 | 261 |
| 1562713_a_at | Hs.465407 | NETO1 | 104 | 174 | 192 | 330 | 283 | 165 | 71 | 64 | 19 |
| 206524_at | Hs.389457 | T (brachyury) | 581 | 552 | 722 | 1761 | 1816 | 604 | 344 | 159 | 123 |
| 219179_at | Hs.48950 | DACT1 | 824 | 683 | 702 | 2734 | 2023 | 1016 | 467 | 285 | 680 |
| 218454_at | Hs.131933 | FLJ22662 | 974 | 1318 | 1106 | 3651 | 2532 | 1205 | 1048 | 874 | 1294 |
| 209897_s_at | Hs.29802 | SLIT2 | 223 | 244 | 212 | 547 | 625 | 321 | 173 | 145 | 285 |
| 205278_at | Hs.420036 | GAD1 | 160 | 167 | 212 | 676 | 723 | 292 | 444 | 264 | 18 |
| 210234_at | Hs.429018 | GRM4 | 384 | 359 | 389 | 738 | 823 | 216 | 116 | 139 | 213 |

Example 18

Markers Useful for Identifying and/or Detecting Embryonic Stem Cell Differentiation Prior to the PrePrimitive Streak Stage (Primitive Ectoderm Cells)

This Example describes markers that are useful in identifying and/or detecting stem cell differentiation prior to the preprimitive streak stage. Such cell types are referred to here as primitive ectoderm cells. It will be appreciated that the primitive ectoderm cell markers described in this Example can be associated with primitive ectoderm cell compositions and used in the methods that have already been described for producing and screening preprimitive streak cells and/or mesendoderm cells.

In order to investigate the process of hESC differentiation to primitive ectoderm, we conducted global expression profiling of differentiating hESC cultures as described in Example 17.

Table 4 below describes marker genes that were expressed at increased or decreased elevated levels prior to 6 hours after contacting the hESCs with activin A. These genes are indicative of primitive ectoderm cells. As indicated for Tables 2 and 3 above, in Table 4, the first column lists the probe set identification number and the second column provides the Unigene Identification Number. The Unigene database is publicly available via the National Center for Biotechnology Information (NCBI) website. The nucleotide and amino acid sequences for any of the marker genes described in this table can therefore be obtained by a query for the appropriate Unigene Identification Number at the NCBI website. The Unigene database is incorporated herein by reference in its entirety. Column three of the Table 4 provides the commonly known gene symbol for each of the markers. The remainder of the columns provide the relative levels of gene expression at the 0, 2, 6, 24, 30, 48 and 96 hour time points. As used in this table, "DE" refers to definitive endoderm and "M" refers to mesoderm.

Table 4 shows that the expression of FZD10, FGF5 and OCT4 mRNAs is substantially upregulated by 2 hours after contacting the hESCs with 100 ng/ml activin A. In contrast, the expression of GBX2, ZFP42 and SOX2 mRNA is substantially downregulated by 2 hours after activin A treatment. The expression of Nanog mRNA is expected to be substantially upregulated at a time prior to six hours post activin A treatment.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Ang, S. L. et al. The formation and maintenance of the definitive endoderm lineage in the mouse: involvement of HNF3/forkhead proteins. Development 119, 1301-1315 (1993).

Ang, S. L. & Rossant, J. HNF-3 beta is essential for node and notochord formation in mouse development. Cell 78, 561-574 (1994).

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Arnold, S. J. et al. Brachyury is a target gene of the Wnt/beta-catenin signaling pathway. Mech Dev 91, 249-258 (2000).

TABLE 4

| Probe Set Id | Unigene Id | Gene Symbol | 0 hr | 2 hr | 6 hr | 24 hr | 30 hr | 48 hr-DE | 48 hr-M | 96 hr-DE | 96 hr-M |
|---|---|---|---|---|---|---|---|---|---|---|---|
| 219764_at | Hs.31664 | FZD10 | 141 | 788 | 318 | 314 | 200 | 67 | 134 | 35 | 9 |
| 210311_at | Hs.37055 | FGF5 | 59 | 130 | 98 | 70 | 49 | 221 | 88 | 161 | 92 |
| 220184_at | Hs.329926 | NANOG | 8341 | 8065 | 14341 | 8716 | 7906 | 4436 | 8874 | 3977 | 1291 |
| 214532_x_at | Hs.249184 | OCT4 | 26278 | 33882 | 33953 | 29083 | 25912 | 15736 | 20166 | 7488 | 18338 |
| 210560_at | Hs.184945 | GBX2 | 161 | 80 | 46 | 29 | 10 | 56 | 43 | 10 | 13 |
| 1554776_at | Hs.335787 | ZFP42 | 2727 | 1445 | 2213 | 1723 | 1493 | 1011 | 1489 | 526 | 2329 |
| 213722_at | Hs.518438 | SOX2 | 937 | 643 | 518 | 387 | 354 | 193 | 719 | 108 | 472 |

Bachiller, D. et al. The organizer factors Chordin and Noggin are required for mouse forebrain development. Nature 403, 658-661 (2000).

Batlle, E. et al. The transcription factor snail is a repressor of E-cadherin gene expression in epithelial tumour cells. Nat Cell Biol 2, 84-89 (2000).

Beck, S., Le Good, J. A., Guzman, M., Ben Haim, N., Roy, K., Beermann, F., and Constam, D. B. (2002). Extra-embryonic proteases regulate Nodal signalling during gastrulation. Nat Cell Biol 4, 981-985.

Beddington, R. S., Rashbass, P., and Wilson, V. (1992). Brachyury—a gene affecting mouse gastrulation and early organogenesis. Dev Suppl, 157-165.

Blum, M. et al. Gastrulation in the mouse: the role of the homeobox gene goosecoid. Cell 69, 1097-1106 (1992).

Bongso, A., Fong, C. Y., Ng, S. C., and Ratnam, S. (1994). Isolation and culture of inner cell mass cells from human blastocysts. Hum Reprod 9, 2110-2117.

Brennan, J. et al. Nodal signalling in the epiblast patterns the early mouse embryo. Nature 411, 965-969 (2001).

Candia, A. F. et al. Mox-1 and Mox-2 define a novel homeobox gene subfamily and are differentially expressed during early mesodermal patterning in mouse embryos. Development 116, 1123-1136 (1992).

Candia, A. F. & Wright, C. V. Differential localization of Mox-1 and Mox-2 proteins indicates distinct roles during development. Int J Dev Biol 40, 1179-1184 (1996).

Chang, H., Brown, C. W., and Matzuk, M. M. (2002). Genetic analysis of the mammalian transforming growth factor-beta superfamily Endocr Rev 23, 787-823.

Ciruna, B. G., Schwartz, L., Harpal, K., Yamaguchi, T. P. & Rossant, J. Chimeric analysis of fibroblast growth factor receptor-1 (Fgfr1) function: a role for FGFR1 in morphogenetic movement through the primitive streak. Development 124, 2829-2841 (1997).

Ciruna, B. & Rossant, J. FGF signaling regulates mesoderm cell fate specification and morphogenetic movement at the primitive streak. Dev Cell 1, 37-49 (2001).

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

de Caestecker, M. The transforming growth factor-beta superfamily of receptors. Cytokine Growth Factor Rev 15, 1-11 (2004).

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Elms, P. et al. Overlapping and distinct expression domains of Zic2 and Zic3 during mouse gastrulation. Gene Expr Patterns 4, 505-511 (2004).

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Haegel, H. et al. Lack of beta-catenin affects mouse development at gastrulation. Development 121, 3529-3537 (1995).

Hallonet, M. et al. Maintenance of the specification of the anterior definitive endoderm and forebrain depends on the axial mesendoderm: a study using HNF3beta/Foxa2 conditional mutants. Dev Biol 243, 20-33 (2002).

Harris, T. M., and Childs, G. (2002). Global gene expression patterns during differentiation of F9 embryonal carcinoma cells into parietal endoderm. Funct Integr Genomics 2, 105-119.

Henry, G. L. & Melton, D. A. Mixer, a homeobox gene required for endoderm development. Science 281, 91-96 (1998).

Herrmann, B. G., Labeit, S., Poustka, A., King, T. R. & Lehrach, H. Cloning of the T gene required in mesoderm formation in the mouse. Nature 343, 617-622 (1990).

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in *Xenopus*. Cell 91, 397-405.

Huelsken, J. et al. Requirement for beta-catenin in anterior-posterior axis formation in mice. J Cell Biol 148, 567-578 (2000).

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Kalinichenko, V. V., Gusarova, G. A., Shin, B. & Costa, R. H. The forkhead box F1 transcription factor is expressed in brain and head mesenchyme during mouse embryonic development. Gene Expr Patterns 3, 153-158 (2003).

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C H., and Broxmeyer, H. E. (1999). Chemokines: signal lamps for trafficking of T and B cells for development and effector function. J Leukoc Biol 65, 6-15.

Kimelman, D., and Griffin, K. J. (2000). Vertebrate mesendoderm induction and patterning. Curr Opin Genet Dev 10, 350-356.

Kinder, S. J. et al. The organizer of the mouse gastrula is composed of a dynamic population of progenitor cells for the axial mesoderm. Development 128, 3623-3634 (2001).

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlow, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lacroix, M. C., Guibourdenche, J., Frendo, J. L., Pidoux, G. & Evain-Brion, D. Placental growth hormones. Endocrine 19, 73-79 (2002).

Lawson, K. A. et al. Bmp4 is required for the generation of primordial germ cells in the mouse embryo. Genes Dev 13, 424-436 (1999).

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cella, 171-181.

Liu, P. et al. Requirement for Wnt3 in vertebrate axis formation. Nat Genet 22, 361-365 (1999).

Lowe, L. A., Yamada, S. & Kuehn, M. R. Genetic dissection of nodal function in patterning the mouse embryo. Development 128, 1831-1843 (2001).

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

Maruoka, Y. et al. Comparison of the expression of three highly related genes, Fgf8, Fgf17 and Fgf18, in the mouse embryo. Mech Dev 74, 175-177 (1998).

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H. (2001). Divergence and convergence of TGF-beta/BMP signaling. J Cell Physiol 187, 265-276.

Nagai, T. et al. The expression of the mouse Zic1, Zic2, and Zic3 gene suggests an essential role for Zic genes in body pattern formation. Dev Biol 182, 299-313 (1997).

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Nieto, M. A., Bennett, M. F., Sargent, M. G. & Wilkinson, D. G. Cloning and developmental expression of Sna, a murine homologue of the *Drosophila* snail gene. Development 116, 227-237 (1992).

Nieto, M. A. The snail superfamily of zinc-finger transcription factors. Nat Rev Mol Cell Biol 3, 155-166 (2002).

Niswander, L. & Martin, G. R. Fgf-4 expression during gastrulation, myogenesis, limb and tooth development in the mouse. Development 114, 755-768 (1992).

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Ormestad, M., Astorga, J. & Carlsson, P. Differences in the embryonic expression patterns of mouse Foxf1 and -2 match their distinct mutant phenotypes. Dev Dyn 229, 328-333 (2004).

Pearce, J. J. & Evans, M. J. Mml, a mouse Mix-like gene expressed in the primitive streak. Mech Dev 87, 189-192 (1999).

Pera, M. F. et al. Regulation of human embryonic stem cell differentiation by BMP-2 and its antagonist noggin. J Cell Sci 117, 1269-1280 (2004).

Perea-Gomez, A. et al. Initiation of gastrulation in the mouse embryo is preceded by an apparent shift in the orientation of the anterior-posterior axis. Curr Biol 14, 197-207 (2004).

Pesce, M. & Scholer, H. R. Oct-4: gatekeeper in the beginnings of mammalian development. Stem Cells 19, 271-278 (2001).

Pevny, L. H., Sockanathan, S., Placzek, M. & Lovell-Badge, R. A role for SOX1 in neural determination. Development 125, 1967-1978 (1998).

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Robb, L. & Tam, P. P. Gastrula organiser and embryonic patterning in the mouse. Semin Cell Dev Biol 15, 543-554 (2004).

Rodaway, A., and Patient, R. (2001). Mesendoderm. an ancient germ layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zic1 expression in brain and somites is affected by BMP and hedgehog signalling. Mech Dev 85, 147-159.

Rossant, J. & Tam, P. P. Emerging asymmetry and embryonic patterning in early mouse development. Dev Cell 7, 155-164 (2004).

Sasaki, H. & Hogan, B. L. Differential expression of multiple fork head related genes during gastrulation and axial pattern formation in the mouse embryo. Development 118, 47-59 (1993).

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shalaby, F. et al. Failure of blood-island formation and vasculogenesis in Flk-1-deficient mice. Nature 376, 62-66 (1995).

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of Xenopus laevis xSox7 cDNA. Biochim Biophys Acta 1309, 73-76.

Shook, D. & Keller, R. Mechanisms, mechanics and function of epithelial-mesenchymal transitions in early development. Mech Dev 120, 1351-1383 (2003).

Sinner, D., Rankin, S., Lee, M. & Zorn, A. M. Sox17 and beta-catenin cooperate to regulate the transcription of endodermal genes. Development 131, 3069-3080 (2004).

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Stainier, D. Y. A glimpse into the molecular entrails of endoderm formation. Genes Dev 16, 893-907 (2002).

Stemmler, M. P., Hecht, A., Kinzel, B. & Kemler, R. Analysis of regulatory elements of E-cadherin with reporter gene constructs in transgenic mouse embryos. Dev Dyn 227, 238-245 (2003).

Sun, X., Meyers, E. N., Lewandoski, M. & Martin, G. R. Targeted disruption of Fgf8 causes failure of cell migration in the gastrulating mouse embryo. Genes Dev 13, 1834-1846 (1999).

Sun, X. et al. Conditional inactivation of Fgf4 reveals complexity of signalling during limb bud development. Nat Genet 25, 83-86 (2000).

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Tam, P. P. & Behringer, R. R. Mouse gastrulation: the formation of a mammalian body plan. Mech Dev 68, 3-25 (1997).

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomas, T., Voss, A. K., Petrou, P. & Gruss, P. The murine gene, Traube, is essential for the growth of preimplantation embryos. Dev Biol 227, 324-342 (2000).

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vallier, L., Reynolds, D. & Pedersen, R. A. Nodal inhibits differentiation of human embryonic stem cells along the neuroectodermal default pathway. Dev Biol 275, 403-421 (2004).

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003). Cell fate decisions within the mouse organizer are governed by graded Nodal signals. Genes Dev 17, 1646-1662.

Wei, C. L. et al. Transcriptome profiling of human and murine ESCs identifies divergent paths required to maintain the stem cell state. Stem Cells 23, 166-185 (2005).

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Weinstein, D. C. et al. The winged-helix transcription factor HNF-3 beta is required for notochord development in the mouse embryo. Cell 78, 575-588 (1994).

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Xu, R. H. et al. BMP4 initiates human embryonic stem cell differentiation to trophoblast. Nat Biotechnol 20, 1261-1264 (2002).

Yamaguchi, T. P., Dumont, D. J., Conlon, R. A., Breitman, M. L. & Rossant, J. flk-1, an flt-related receptor tyrosine kinase is an early marker for endothelial cell precursors. Development 118, 489-498 (1993).

Yamaguchi, T. P., Takada, S., Yoshikawa, Y., Wu, N. & McMahon, A. P. T (Brachyury) is a direct target of Wnt3a during paraxial mesoderm specification. Genes Dev 13, 3185-3190 (1999).

Yang, D. H. et al. Disabled-2 is essential for endodermal cell positioning and structure formation during mouse embryogenesis. Dev Biol 251, 27-44 (2002).

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993).
Nodal is a novel TGF-beta-like gene expressed in the mouse node during gastrulation. Nature 361, 543-547.

What is claimed is:

1. An in vitro method of producing mesoderm cells, comprising:
   (a) culturing human pluripotent stem cells in a first medium comprising activin A for about 24 hours;
   (b) removing the activin A from the first medium to form a first cell population; and
   (c) culturing the first cell population of step (b) in a second medium comprising no activin A for a sufficient time to form a second cell population comprising mesoderm cells.

2. The in vitro method of claim 1, wherein the first medium does not comprise serum.

3. The in vitro method of claim 1, wherein the first medium comprises activin A at a concentration of at least 30 ng/ml.

4. The in vitro method of claim 1, wherein the first medium comprises activin A at a concentration of 100 ng/ml.

5. The in vitro method of claim 1, wherein in step (c) the first cell population is cultured in the second medium for about 48 hours.

6. The in vitro method of claim 1, wherein the mesoderm cells express Brachyury, forkhead box protein (FOXF1), vascular endothelial growth factor receptor 2 (FLK1), bone morphogenetic protein 4 (BMP4), homeobox protein MOX1, or stromal cell derived factor 1 (SDF1).

7. The in vitro method of claim 1, wherein the human pluripotent stem cells are human embryonic stem cells.

8. The in vitro method of claim 1, wherein the first cell population comprises mesendoderm cells.

9. The in vitro method of claim 1, wherein the second medium comprises at least 0.2% serum.

10. An in vitro method of producing preprimitive streak cells, comprising:
    culturing human pluripotent stem cells in a medium comprising activin A for about 6 hours to about 24 hours,
    thereby forming preprimitive streak cells; and isolating the preprimitive streak cells.

11. The in vitro method of claim 10, wherein the medium does not comprise serum.

12. An in vitro method of producing preprimitive streak cells, comprising:
    culturing human pluripotent stem cells in a medium comprising activin A at concentration of at least 30 ng/ml for about 6 hours to about 24 hours, thereby forming preprimitive streak cells.

13. The in vitro method of claim 12, wherein the medium comprises activin A at a concentration of 100 ng/ml.

14. The in vitro method of claim 10, wherein the preprimitive streak cells express fibroblast growth factor 8 (FGF8), nuclear localized β-catenin, or both FGF8 and nuclear localized β-catenin.

15. The in vitro method of claim 14, wherein the expression of FGF8 or nuclear localized β-catenin in the preprimitive streak cells is greater than the expression of brachyury, fibroblast growth factor 4 (FGF4), zinc finger protein SNAI1, SRY-related HMG-box 17 (SOX-17), hepatocyte nuclear factor 3-beta (FOXA2), SRY-related HMG-box 7 (SOX7), or SRY-related HMG-box 1 (SOX1) on the preprimitive streak cells.

16. The in vitro method of claim 10, wherein the human pluripotent stem cells are human embryonic stem cells.

17. The in vitro method of claim 10, wherein the medium comprises about 0.2% serum.

18. The in vitro method of claim 10, wherein the medium comprises about 0.2% serum to about 2.0% serum.

* * * * *